US007601501B2

(12) United States Patent
Zhao et al.

(10) Patent No.: US 7,601,501 B2
(45) Date of Patent: Oct. 13, 2009

(54) CONTROLLING OSTEOGENESIS BY INHIBITION OF OSTEOGENIC SUPPRESSORS

(75) Inventors: Yuanxiang Zhao, Pomona, CA (US); Sheng Ding, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 11/836,512

(22) Filed: Aug. 9, 2007

(65) Prior Publication Data

US 2008/0038202 A1 Feb. 14, 2008

Related U.S. Application Data

(60) Provisional application No. 60/822,184, filed on Aug. 11, 2006.

(51) Int. Cl.
*C12Q 1/68* (2006.01)
*C07H 21/02* (2006.01)
*C07H 21/04* (2006.01)
*C12N 15/85* (2006.01)

(52) U.S. Cl. ......................... 435/6; 536/23.1; 536/24.5; 435/325

(58) Field of Classification Search ....................... None
See application file for complete search history.

(56) References Cited

U.S. PATENT DOCUMENTS

| | | | |
|---|---|---|---|
| 2004/0157864 A1 | 8/2004 | Wu et al. | |
| 2005/0176707 A1 | 8/2005 | Chen et al. | |
| 2006/0019907 A1 | 1/2006 | Aggarwal et al. | |
| 2007/0254884 A1 | 11/2007 | Shuibing et al. | |

FOREIGN PATENT DOCUMENTS

WO WO 94/06438 A1 3/1994

OTHER PUBLICATIONS

Wei et al., International Union of Pharmacology. LII. Nomenclature and Molecular Relationships of Calcium-Activated Potassium Channels, 2005, Pharmacol Rev, vol. 57, No. 4, pp. 463-472.*
Campagnoli, C. et al., "Identification of mesenchymal stem/progenitor cells in human first-trimester fetal blood, liver, and bone barrow," 2001, Blood, 98:2396-2402.
Caplen, N. J. et al., "Specific inhibition of gene expression by small double-stranded RNAs in invertebrate and vertebrate systems," Proc Natl Acad Sci U S A, 98:9742-9747 (2001).
Dezawa, M. et al., "Specific induction of neuronal cells from bone marrow stromal cells and application for autologous transplantation," 2004, J Clin Invest., 113:1701-1710.
Dezawa, M. et al., "Bone Marrow Stromal Cells Generate Muscle Cells and Repair Muscle Degeneratio," 2005, Science, 309:314-317.
Horwitz, E. M. et al., "Isolated allogeneic bone marrow-derived mesenchymal cells engraft and stimulate growth in children with osteogenesis imperfecta: Implications for cell therapy of bone," 2002, Proc Natl Acad Sci U S A, 99:8932-8737().
Paddison, P. J. et al., "Short hairpin RNAs (shRNAs) induce sequence-specific silencing in mammalian cells," Genes Dev 16:948-958 (2002).
Paddison, P. J. et al., "A resource for large-scale RNA-interference-based screens in mammals," Nature 428:427-431 (2004).
Patil, et al., "DNA-Based Therapeutics and DNA Delivery Systems: a Comprehensive Review," 2005, AAPS Journal, 7(1), 9, E61-E77.
Pittenger, et al., "Multilineage Potential of Adult Human Mesenchymal Stem Cells," 1999, Science, vol. 284, 143-147.
Pittenger, M. F. et al., "Mesenchymal Stem Cells and Their Potential as Cardiac Therapeutics," Circ Res 95:9-20 (2004).
Prockop, D. J. "Adult stem cells gradually come of age," Nat Biotechnol 20:791-792 (2002).
Prockop, D. J. "Marrow Stromal Cells as Stem Cells for Nonhematopoietic Tissues," Science 276:71-74 (1997).
Ryan, J. M. et al., "Mesenchymal stem cells avoid allogeneic rejection," J Inflamm (Lond) 2:8 (2005).
Sui, G. et al., "A DNA vector-based RNAi technology to suppress gene expression in mammalian cells," Proc Natl Acad Sci U S A 99:5515-5520 (2002).
Woodbury, D. et al., "Adult rat and human bone marrow stromal cells differentiate into neurons," J Neurosci Res 61:364-370 (2000).
Yu, J. Y. et al., "RNA interference by expression of short-interfering RNAs and hairpin RNAs in mammalian cells," Proc Natl Sci U S A 99:6047-6052 (2002).
Zheng, L. et al., "An approach to genomewide screens of expressed small interfering RNAs in mammalian cells," Proc Natl Acad Sci U S A 101:135-140 (2004).
Bertaux, Karine et al.; "Runx2 regulates the expression of GNAS of SaOs-2 cells"; 2006, *Bone*, vol. 38, pp. 943-950.
Riminucci, M. et al.; "Osteoclastogenesis in fibrous dysplasia of bone: in situ and in vitro analysis of IL-6 expression"; 2003, *Bone*, vol. 33, pp. 434-442.
Zamurovic, Natasa et al.; "Coordinated Activation of Notch, Wnt, and Transforming Growth Factor-β Signaling Pathways in Bone Morphogenic Protein 2-induced Osteogenesis"; 2004, *The Journal of Biological Chemistry*, vol. 279, No. 36, pp. 37704-37715.
Zhao, et al., "*A High Throughput siRNA Library Screen Identifies Osteogenic Suppressors in Human Mesenchymal Stem Cells," PNAS*, Jun. 5, 2007, vol. 104, No. 23, pp. 9673-9678.

* cited by examiner

*Primary Examiner*—Amy Bowman
(74) *Attorney, Agent, or Firm*—Townsend and Townsend and Crew LLP

(57) ABSTRACT

The present invention provides methods of screening for agents that inhibit the activity or expression of one or more polypeptides that contribute to the suppression of osteogenesis. The invention also provides methods of inducing osteogenesis in a cell by administering to the cell an agent that inhibits one or more polypeptides that contribute to the suppression of osteogenesis.

10 Claims, 11 Drawing Sheets

CONTROLLING OSTEOGENESIS BY INHIBITION OF OSTEOGENIC SUPPRESSORS

CROSS-REFERENCE TO RELATED APPLICATIONS

The present application claims the benefit of U.S. Application No. 60/822,184, filed Aug. 11, 2006, the entire disclosure of which is hereby incorporated herein by reference.

BACKGROUND OF THE INVENTION

Tissue-specific (or adult) stem cells are regarded as the source for normal tissue homeostasis and tissue repair. They also provide tremendous promise for regenerative medicine due to their capacity to proliferate and differentiate into a variety of mature cell types. Human mesenchymal stem cells (hMSCs) can differentiate into osteocytes, adipocytes, chondrocytes, muscle cells and neurons. However, the molecular mechanisms underlying these differentiating processes are poorly understood.

RNA-mediated interference (RNAi) is a highly conserved gene silencing event functioning through targeted destruction of individual mRNA by a homologous double-stranded small interfering RNA (siRNA) (Fire, A. et al., *Nature* 391:806-811 (1998)). siRNAs generated by both chemical synthesis and in vitro or in vivo transcription through vector-based expression systems have been proven very useful tools in studying gene loss-of-function in mammalian cells (Brummelkamp, T. R. et al., *Science* 296:550-553 (2002); Caplen, N. J. et al., *Proc Natl Acad Sci USA* 98:9742-9747 (2001); Elbashir, S. M. et al., *Nature* 411:494-498 (2001); Lee, N. S. et al., *Nat Biotechnol* 20:500-505 (2002); Miyagishi, P M. et al., *Nat Biotechnol* 20: 497-500 (2002); Paddison, P. J. et al., *Genes Dev* 16:948-958 (2002); Paul, C. P. et al., *Nat Biotechnol* 20:505-508 (2002); Sui, G. et al., *Proc Natl Acad Sci USA* 99:5515-5520 (2002); Yu, J. Y. et al., *Proc Natl Acad Sci USA* 99:6047-6052 (2002)). While high throughput screens using genome-scale siRNA libraries have been successfully carried out in mammalian cells (Berns, K. et al., *Nature* 428:431-437 (2004); Paddison, P. J. et al., *Nature* 428:427-431 (2004); Zheng, L. et al., *Proc Natl Acad Sci USA* 101:135-140 (2004)), effective application of arrayed synthetic siRNA library in stem cells has not been reported. Human mesenchymal stem cells (hMSCs) can be easily isolated from adults and expanded rapidly in vitro. Due to their ability to differentiate into various mature cell types (Prockop, D. J. *Nat Biotechnol* 20:791-792 (2002); Ryan, J. M. et al., *J Inflamm* (*Lond*) 2:8 (2005)) (Campagnoli, C. et al., *Blood* 98:2396-2402 (2001); Dezawa, M. et al., *Science* 309:314-317 (2005); Dezawa, M. et al., *J Clin Invest* 113:1701-1710 (2004); Pittenger, M. F. et al., *Science* 284:143-147 (1999); Pittenger, M. F. et al., *Circ Res* 95:9-20 (2004); Woodbury, D. et al., *J Neurosci Res* 61:364-370 (2000)), they have been of great interests to researchers exploring cell-based therapies for degenerative diseases including bone disorders (Dezawa, M. et al., *Science* 309: 314-317 (2005); Dezawa, M. et al., *J Clin Invest* 113:1701-1710 (2004); Horwitz, E. M. et al., *Proc Natl Acad Sci USA* 99:8932-8937 (2002); Pittenger, M. F. et al., *Circ Res* 95:9-20 (2004); Prockop, D. J. *Science* 276:71-74 (1997)). Cell fate transition from stem cell self-renewal to differentiation involves not only positive regulators but also negative regulators that normally suppress differentiation.

There is a need for methodologies that influence the differentiation path of mesenchymal stem cells, for example, into cells of an osteoblast lineage. The present invention addresses this and other needs.

BRIEF SUMMARY OF THE INVENTION

The present invention provides methods for screening for agents that promote osteogenesis by suppressing the activity or expression of one or more of the polypeptides listed in Table 1. The invention further provides methods for promoting osteogenesis in a cell by suppressing the activity or expression of one or more of the polypeptides listed in Table 1.

Accordingly, in a first aspect, the invention provides methods for identifying agents that promote osteogenesis. In some embodiments, the methods comprise:

(a) contacting a plurality of agents to at least one of the polypeptides or polynucleotides selected from Table 1;

(b) measuring the activity of at least one of the polypeptides or polynucleotides;

(c) selecting at least one of the plurality of agents, wherein the selected agent(s) inhibit the activity of at least one of the polypeptides or polynucleotides; and (d) measuring the ability of the selected agent(s) to promote osteogenesis, thereby identifying agents that promote osteogenesis. In some embodiments, the polypeptides or polynucleotides are expressed in a host cell.

In another embodiment, the methods comprise:

(a) contacting a plurality of agents to cells expressing at least one of the polypeptides or polynucleotides selected from Table 1;

(b) measuring the expression (i.e., transcription or translation) of at least one of the polypeptides or polynucleotides;

(c) selecting at least one of the plurality of agents, wherein the selected agent(s) inhibit the expression of at least one of the polypeptides or polynucleotides; and (d) measuring the ability of the selected agent(s) to promote osteogenesis, thereby identifying agents that promote osteogenesis.

In some embodiments of the screening methods, the measuring step (b) comprises measuring the level of transcription.

In some embodiments of the screening methods, the measuring step (d) is carried out in vitro. In some embodiments, the measuring step (d) is carried out in vivo.

The cells used in the contacting and measuring steps can be prokaryotic or eukaryotic. In some embodiments, the cells are mammalian cells, for example, stem cells or mesenchymal stem cells.

In a further aspect, the invention provides methods for promoting osteogenesis in a cell. In some embodiments, the methods comprise contacting the cell with an siRNA that inhibits expression of at least one of the gene products selected from Table 1.

In a related aspect, the invention provides methods for promoting osteogenesis in a cell. In some embodiments, the methods comprise contacting a cell with an agent that inhibits the activity of a polypeptide selected from Table 1.

With regard to the embodiments for promoting osteogenesis in a mammalian cell, in some embodiments, the methods are performed in vivo. In some embodiments, the methods are performed in vitro. In some embodiments, the methods are performed ex vivo.

In some embodiments of the screening and treatment methods, the cell is a mammalian cell. In some embodiments, the cell is a stem cell. In some embodiments, the stem cell is a mesenchymal stem cell.

DETAILED DESCRIPTION OF THE INVENTION

I. Introduction

Figure 1:
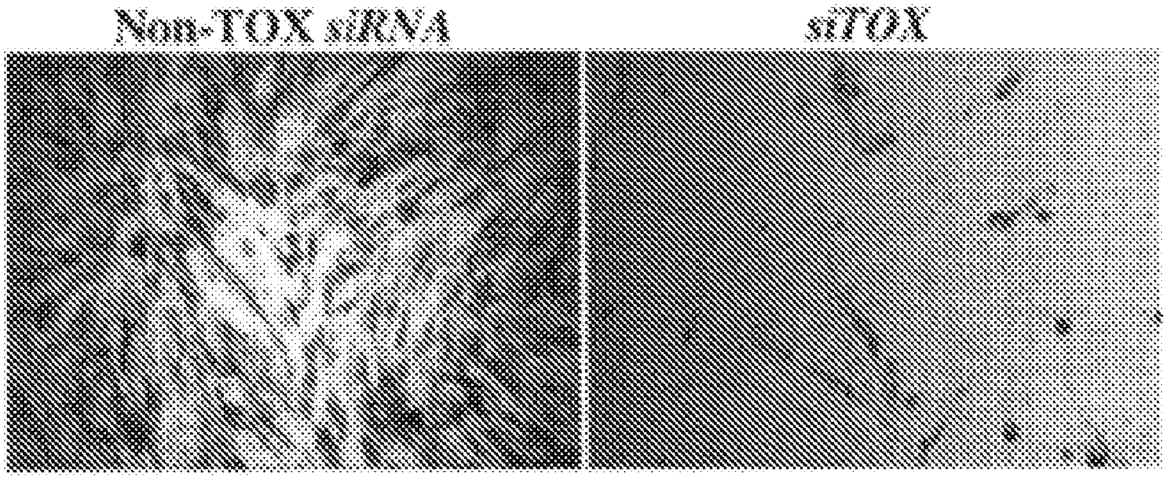
FIG. 1 illustrates siRNA transfection efficiency in hMSCs was above 90%. Cells successfully transfected with siTOX underwent apoptosis, while cells transfected with non-TOX siRNA remained alive.

A synthetic siRNA library targeting 5,000 human genes was screened to identify the endogenous repressors of osteogenic specification, which upon silencing initiate differentiation of hMSCs into osteoblasts. This screen yielded 53 suppressors of osteogenic specification in hMSCs. See, Table 1. Furthermore, cAMP was identified to play reverse roles in osteogenesis vs. adipogenesis. The present invention finds use in modulating the genetic network controlling osteogenesis and in treating bone diseases.

II. Definitions

"Osteogenesis," as used herein, refers to proliferation of bone cells and growth of bone tissue (i.e., synthesis and deposit of new bone matrix) from undifferentiated stem cells and cells of osteoblast lineage. Osteogenesis also refers to differentiation or transdifferentiation of progenitor or precursor cells into bone cells (i.e., osteoblasts). Progenitor or precursor cells can be pluripotent stem cells including, e.g., mesenchymal stem cells. Progenitor or precursor cells can be cells pre-committed to an osteoblast lineage (e.g., pre-osteoblast cells) or cells that are not pre-committed to an osteoblast lineage (e.g., pre-adipocytes or myoblasts).

The term "agent" refers to any compound useful in the screening assays described herein. An agent can be, for example, an organic compound, a polypeptide (e.g., a peptide or an antibody), a nucleic acid (e.g., DNA, RNA, double-stranded, single-stranded, an oligonucleotide, antisense RNA, small inhibitory RNA, micro RNA, a ribozyme, etc.), an oligosaccharide, a lipid. Usually, the agents used in the present screening methods have a molecular weight of less than 10,000 daltons, for example, less than 8000, 6000, 4000, 2000 daltons.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, RNAi or siRNA, asRNA, oligonucleotide, etc. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

The terms "short-inhibitory RNA" and "siRNA" interchangeably refer to short double-stranded RNA oligonucleotides that mediate RNA interference (also referred to as "RNA-mediated interference," or RNAi). RNAi is a highly conserved gene silencing event functioning through targeted destruction of individual mRNA by a homologous double-stranded small interfering RNA (siRNA) (Fire, A. et al., *Nature* 391:806-811 (1998)). Mechanisms for RNAi are reviewed, for example, in Bayne and Allshire, *Trends in Genetics* (2005) 21:370-73; Morris, *Cell Mol Life Sci* (2005) 62:3057-66; Filipowicz, et al., *Current Opinion in Structural Biology* (2005) 15:331-41.

The term "activity" refers to the commonly recognized functioning of a polypeptide known in the art. For example, the polypeptides listed in Table 1 have commonly recognized activities as enzymes, receptors, cell adhesion molecules, intracellular signaling mediators, etc. Assays for measuring the activities of the listed proteins, including enzymatic activity assays, receptor signaling assays, receptor-ligand binding assays, cell migration assays, are known in the art. The activity of a protein can also be correlated with its expression, for example, the transcription or translation of the polypeptide.

The term "promote" refers to the increase in a measured parameter (e.g., activity, expression, osteogenesis) in a treated cell (tissue or subject) in comparison to an untreated cell (tissue or subject). A comparison can also be made of the same cell or tissue or subject between before and after treatment. The increase is sufficient to be detectable. In some embodiments, the increase in the treated cell is at least about 50%, 60%, 70%, 80%, 90%, 1-fold, 2-fold, 3-fold, 4-fold or more in comparison to an untreated cell.

The term "inhibit" refers to the decrease in a measured parameter (e.g. activity, expression, osteogenesis) in a treated cell (tissue or subject) in comparison to an untreated cell (tissue or subject). A comparison can also be made of the same cell or tissue or subject between before and after treatment. The decrease is sufficient to be detectable. In some embodiments, the decrease in the treated cell is at least about 50%, 60%, 70%, 80%, 90%, or completely inhibited in comparison to an untreated cell. In some embodiments the measured parameter is undetectable (i.e., completely inhibited) in the treated cell in comparison to the untreated cell.

A "stem cell," as used herein, refers to any mammalian pluripotent cell or multipotent cell or progenitor cell or precursor cell that is capable of differentiating into multiple cell types. Stem cells suitable for use in the methods of the present invention include those that are capable of differentiating into cells of osteoblast lineage, e.g., osteoblasts. Suitable multipotent cells or precursor cells for use in the methods of the present invention include, for example, mesenchymal stem cells, pre-osteoblast cells, pre-adipocyte cells, and myoblast cells.

"Differentiate" or "differentiation," as used herein, refers to the process by which precursor or progenitor cells (i.e., stem cells) differentiate into specific cell types, e.g., osteoblasts. Differentiated cells can be identified by their patterns of gene expression and cell surface protein expression. Typically, cells of an osteoblast lineage express genes including, for example, alkaline phosphatase, collagen type I, osteocalcin, and osteoponin. Typically, cells of an osteoblast lineage express bone specific transcription factors including, for example, Cbfa1/Runx2 and Osx (see, e.g., Olsen, et al, 2000 supra and Nakashima et al., Cell 108(1): 17-29 (2002). Additional transcription factors that are involved in osteoblast differentiation include, e.g., gsc, D1x1, D1x5, Msx1, Cart1, Hoxa1, Hoxa2, Hoxa3, Hoxb1, rae28, Twist, AP-2, Mf1, Pax1, Pax3, Pax9, TBX3, TBX4, TBX5, and Brachyury (see, e.g., Olsen et al, 2000 supra).

"Transdifferentiation" refers to the process by which precursor or progenitor cells (i.e., stem cells) pre-committed to cell types of one lineage differentiate into specific cell types of another lineage, e.g., pre-adipocytes transdifferentiate into osteoblasts or myoblasts transdifferentiate into osteoblasts. Transdifferentiated cells can be identified by their patterns of gene expression and cell surface protein expression. Typically, cells of an osteoblast lineage express genes including, for example, alkaline phosphatase, collagen type I, osteocalcin, and osteoponin. Typically, cells of an osteoblast lineage express bone specific transcription factors including, for example, Cbfa1/Runx2 and Osx (see, e.g., Olsen et al, 2000 supra and Nakashima et al., supra). Additional transcription factors that are involved in osteoblast differentiation include, e.g., gsc, D1x1, D1x5, Msx1, Cart1, Hoxa1, Hoxa2, Hoxa3, Hoxb1, rae28, Twist, AP-2, Mf1, Pax1, Pax3, Pax9, TBX3, TBX4, TBX5, and Brachyury (see, e.g., Olsen et al, 2000 supra).

A "solid support," as used herein in connection with inducing osteogenesis, refers to a three-dimensional matrix or a planar surface on which the stem cells can be cultured. The solid support can be derived from naturally occurring substances (i.e., protein based) or synthetic substances. For example, matrices based on naturally occurring substances may be composed of autologous bone fragments or commercially available bone substitutes as described in e.g., Clokie et al., *J. Craniofac. Surg.* 13(1): 111-21 (2002) and Isaksson, *Swed. Dent. J Suppl.* 84:1-46 (1992). Suitable synthetic matrices are described in, e.g., U.S. Pat. Nos. 5,041,138; 5,512,474, and 6,425,222. For example, biodegradable artificial polymers, such as polyglycolic acid, polyorthoester, or polyanhydride can be used for the solid support. Calcium carbonate, aragonite, and porous ceramics (e.g., dense hydroxyapatite ceramic) are also suitable for use in the solid support. Polymers such as polypropylene, polyethylene glycol, and polystyrene can also be used in the solid support. Cells cultured and differentiated on a solid support that is a three-dimensional matrix typically grow on all of the surfaces of the matrix, e.g., internal and external. Cells cultured and differentiated on a solid support that is planar typically grow in a monolayer.

The term "plurality" refers to two or more.

III. Methods of Screening for Agents that Promote Osteogenesis

Contacting One or More Polypeptides with One or More Agents

The present invention provides for methods of screening comprising contacting at least one of the polypeptides listed in Table 1 with one or more agents that are candidates to inhibit one or more of the polypeptides listed in Table 1. In some embodiments, a plurality of different agents are screened, for example, 50, 100, 250, 500, 1000, 10,000 or more different agents. The polypeptides can be in a host cell, in a cell extract, or purified (e.g., partially, substantially or completely), as desired.

Screening assays for inhibitory agents of the polypeptides of Table 1 wherein the polypeptides are not in a host cell can be used when measuring, for example, binding activity or enzymatic activity. For example, the ability of a candidate agent to inhibit the binding of a natural substrate or ligand can be measured. In other embodiments, the ability of a candidate agent to inhibit enzymatic consumption of substrate or accumulation of product can be measured.

In some embodiments, the assays are designed to screen large combinatorial libraries by automating the assay steps and providing compounds from any convenient source to assays, which are typically run in parallel (e.g., in microtiter formats or in microwell plates in robotic assays). The combinatorial libraries can be completely random, or comprise members that contain a core structure based on one or more promising lead compounds. The combinatorial libraries can be completely synthetic or can include some or all members that are derived from naturally occurring sources, including, for example, bacteria, fungi, plants, insects and vertebrate (e.g., *Xenopus* (frog) or *Anguilla* (eel)) and non-vertebrate animals (e.g., *Strongylocentrotus* (sea urchin) or mollusks). See also, Boldi, *Combinatorial Synthesis of Natural Product Based Libraries,* 2006, CRC Press.

In one embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. See, for example, U.S. Pat. Nos. 5,663,046; 5,958,792; 6,185,506; 6,541,211; 6,721,665, the disclosures of which are hereby incorporated herein by reference. Such combinatorial chemical libraries include, but are not limited to, peptide libraries (see, e.g., U.S. Pat. No. 5,010,175; Furka, *Int. J. Pept. Prot. Res.* 37:487-493 (1991); Houghton, et al., *Nature* 354:84-88 (1991); and Combinatorial Peptide Library Protocols, Cabilly, ed., 1997, Humana Press. Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al, J. Amer. Chem. Soc. 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994); *Combinatorial Libraries Synthesis, Screening and Application Potential*, Cortese, ed., 1995, Walter De Gruyter Inc; and Obrecht and Villalgordo, *Solid-Supported Combinatorial and Parallel Synthesis of Small-Molecular-Weight Compound Libraries,* 1998, Elsevier Science Ltd), oligocarbamates (Cho et al., *Science* 261:1303 (1993)), and/or peptidyl phosphonates (Campbell et al., *J. Org. Chem.* 59:658 (1994)), nucleic acid libraries (see Ausubel, infra, Sambrook and Russell, infra and U.S. Pat. Nos. 6,955,879; 6,841,347; 6,830,890; 6,828,098; 6,573,098; and 6,399,334), peptide nucleic acid libraries (see, e.g., U.S. Pat. Nos. 5,539,083; 5,864,010 and 6,756,199), antibody libraries (see, e.g., Vaughn et al., *Nature Biotechnology,* 14(3):309-314 (1996) and PCT/US96/10287), carbohydrate libraries (see, e.g., Liang et al., Science, 274:1520-1522 (1996); U.S. Pat. No. 5,593,853; and *Solid Support Oligosaccharide Synthesis and Combinatorial Carbohydrate Libraries*, Seeberger, ed., 2004, John Wiley & Sons (E-book)), small organic molecule libraries (see, e.g., benzodiazepines, Baum C&EN, January 18, page 33 (1993) and U.S. Pat. No. 5,288,514; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337, and the like). See also, *Combinatorial Library Design and Evaluation: Principles, Software Tools, and Applications in Drug Discovery*, Ghose, et al., eds., 2001, Marcel Dekker; *Molecular Diversity and Combinatorial Chemistry: Libraries and Drug Discovery*, Chaiken and Janda, eds., 1996, Oxford Univ Pr.; and *Combinatorial Library Methods and Protocols*, English, ed., 2002, Humana Press.

Devices for the preparation of combinatorial libraries are commercially available (see, e.g., Advanced Chem Tech, Louisville Ky., Symphony, Rainin, Woburn, Mass., Applied Biosystems, Foster City, Calif., Millipore, Bedford, Mass. and Caliper Life Sciences, Hopkinton, Mass.).

In some embodiments, the screening assays can be conveniently carried out in multiwell plates (e.g., 96-well, 384-well, etc.) wherein each agent to be screened is individually tested in a single well. In some embodiments, two or more candidate agents are tested in a single reaction mixture.

Agents

The agents used in the screening methods can be, for example, small organic compounds (e.g., molecular weight less than 10,000 daltons, for example, less than 8000, 6000, 4000, 2000 daltons), lipids, sugars, polypeptides, nucleic acids (e.g., oligonucleotides, DNA, RNA, ribozymes, short inhibitory RNA (siRNA), micro RNA (miRNA), etc.). Typically, the amount of inhibitory agent contacted with the cells is from about 0.05 nM to about 50 μM, for example, about 1 nM to about 1 μM, about 0.1 μM to about 50 μM, or about 0.05 nM, 0.1 nM, 0.5 nM, 1.0 nM, 1.5 nM, 25 nM, 100 nM, 1.0 μM, 10 μM, or 50 μM.

Organic Compounds

In some embodiments, the one or more agents are small organic compounds. Essentially any chemical compound can be screened as a potential inhibitor of one or more of the polypeptides of Table 1 in the assays of the invention. Most preferred are generally compounds that can be dissolved in aqueous or organic (especially DMSO-based) solutions and compound which fall within Lipinski's "Rule of 5" criteria. The assays are designed to screen large chemical libraries by automating the assay steps and providing compounds from any convenient source to assays, which are typically run in parallel (e.g., in microtiter formats on multiwell plates in robotic assays). It will be appreciated that there are many suppliers of chemical compounds, including Sigma-Aldrich (St. Louis, Mo.); Fluka Chemika-Biochemica Analytika (Buchs Switzerland), as well as numerous providers of small organic molecule libraries ready for screening, including Chembridge Corp. (San Diego, Calif.), Discovery Partners International (San Diego, Calif.), Triad Therapeutics (San Diego, Calif.), Nanosyn (Menlo Park, Calif.), Affymax (Palo Alto, Calif.), ComGenex (South San Francisco, Calif.), Tripos, Inc. (St. Louis, Mo.), Reaction Biology Corp. (Malvern, Pa.), Biomol Intl. (Plymouth Meeting, Pa.), TimTec (Newark, Del.), and AnalytiCon (Potsdam, Germany), among others.

Polypeptides and Antibodies

In some embodiments, the one or more agents are polypeptides (including but not limited to peptides having 8-30 amino acids, antibodies, etc.). Polypeptide libraries useful for screening are commercially available from numerous sources, for example, from Cambridge Peptides, Cambridge, United Kingdom; JPT Peptide Technologies, Berlin, Germany; Bio-Synthesis, Lewisville, Tex.; and Prestwick Chemical, Washington, D.C. Methods for producing peptide libraries are also well known in the art. See, for example, *Synthetic Peptides: A User's Guide*, Grant, ed., 2002, Oxford University Press; Benoiton, *Chemistry of Peptide Synthesis,* 2005, CRC Press; Jones, *Amino Acid and Peptide Synthesis,* 2002, Oxford University Press. Peptide synthesizers are commercially available, for example, from TechniKrom, Inc., Evanston, Ill.; Applied Biosystems, Foster City, Calif.; and Advanced Automated Peptide Protein Technologies (AAPPT), Louisville, Ky.

In some embodiments, the one or more agents are antibodies, including polyclonal or monoclonal antibodies, Fab fragments, single chain antibodies (scFv), complementary regions from combinatorial libraries, etc. A combinatorial antibody library useful for screening purposes is available from MorphoSys, Martinsried/Planegg, Germany. Methods for producing antibody libraries are known in the art.

Inhibitory Oligonucleotides

In some embodiments, the one or more agents are inhibitory oligonucleotides, including antisense oligonucleotides, ribozymes, short inhibitory RNA (siRNA), micro RNA (miRNA). Libraries of randomized oligonucleotides are commercially available from, for example, Integrated DNA Technologies (IDT), Coralville, Iowa; Ambion, Austin, Tex. and Qiagen, Valencia, Calif. In one embodiment, the inhibitory oligonucleotides inhibit the activity or expression level of one or more of the polypeptides listed in Table 1.

Antisense Oligonucleotides

An "antisense" oligonucleotide corresponds to an RNA sequence as well as a DNA sequence coding therefor, which is sufficiently complementary to a particular mRNA molecule, for which the antisense RNA is specific, to cause molecular hybridization between the antisense RNA and the mRNA such that translation of the mRNA is inhibited. Such hybridization can occur under in vitro and in vivo conditions. The antisense molecule must have sufficient complementarity to the target gene so that the antisense RNA can hybridize to the target gene (or mRNA) and inhibit target gene expression regardless of whether the action is at the level of splicing, transcription, or translation. In some embodiments, the complementary antisense sequence is about 15-30 nucleotides in length, for example, 15, 16, 17, 18, 19, 20, 21, 22, 23, 24, 25, 26, 27, 28, 29 or 30 nucleotides, or longer or shorter, as desired. The antisense components of the present invention may be hybridizable to any of several portions of the target cDNA, including the coding sequence, 3' or 5' untranslated regions, or other intronic sequences, or to target mRNA.

Antisense oligonucleotides can include sequences hybridizable to any of several portions of the target DNA, including the coding sequence, 3' or 5' untranslated regions, or other intronic sequences, or to target mRNA.

Small Inhibitory RNA Oligonucleotides siRNA technology relates to a process of sequence-specific post-transcriptional gene repression which can occur in eukaryotic cells. In general, this process involves degradation of an mRNA of a particular sequence induced by double-stranded RNA (dsRNA) that is homologous to that sequence. siRNA can be effected by introduction or expression of relatively short homologous dsRNAs. For screening purposes, the double stranded oligonucleotides used to effect inhibition of expression, at either the transcriptional or translational level, can be of any convenient length. siRNA molecules are typically from about 15 to about 30 nucleic acids in length, for example, about 19-25 nucleic acids in length, for example, about 15, 16, 17, 18, 19, 20, 21, 22, 23, 24, 25, 26, 27, 28, 29, 30 nucleic acids in length. Optionally the dsRNA oligonucleotides can include 3' overhang ends. Exemplary 2-nucleotide 3' overhangs can be composed of ribonucleotide residues of any type and can be composed of 2'-deoxythymidine resides, which lowers the cost of RNA synthesis and can enhance nuclease resistance of siRNAs in the cell culture medium and within transfected cells (see, Elbashi et al., 2001*, Nature* 411:494-8).

Longer dsRNAs of 50, 75, 100 or even 500 base pairs or more can also be utilized in certain embodiments of the invention. Exemplary concentrations of dsRNAs for effecting inhibition are about 0.05 nM, 0.1 nM, 0.5 nM, 1.0 nM, 1.5 nM, 25 nM or 100 nM, although other concentrations can be utilized depending upon the nature of the cells treated, the gene target and other factors readily discernable to the skilled artisan.

Exemplary dsRNAs can be synthesized chemically or produced in vitro or in vivo using appropriate expression vectors. Exemplary synthetic RNAs include 21 nucleotide RNAs chemically synthesized using methods known in the art. Synthetic oligonucleotides are preferably deprotected and gel-purified using methods known in the art (see, e.g., Elbashir, et al., 2001, *Genes Dev.* 15:188-200). Alternatively the dsRNAs can be transcribed from a mammalian expression vector. A single RNA target, placed in both possible orientations downstream of an appropriate promoter for use in mammalian cells, will transcribe both strands of the target to create a dsRNA oligonucleotide of the desired target sequence. Any of the above RNA species will be designed to include a portion of nucleic acid sequence represented in a target nucleic acid.

The specific sequence utilized in design of the siRNA oligonucleotides can be any contiguous sequence of nucleotides contained within the expressed gene message of the target. Programs and algorithms, known in the art, may be used to select appropriate target sequences. See, the Ambion website at ambion.com. In addition, optimal sequences can be selected utilizing programs designed to predict the secondary structure of a specified single stranded nucleic acid sequence and allowing selection of those sequences likely to occur in exposed single stranded regions of a folded mRNA. Methods and compositions for designing appropriate siRNA oligonucleotides may be found, for example, in U.S. Pat. No. 6,251,588, the contents of which are incorporated herein by reference.

Ribozymes

Ribozymes are enzymatic RNA molecules capable of catalyzing specific cleavage of RNA. The composition of ribozyme molecules preferably includes one or more sequences complementary to a target mRNA, and the well known catalytic sequence responsible for mRNA cleavage or a functionally equivalent sequence (see, e.g., U.S. Pat. No. 5,093,246, which is incorporated herein by reference in its entirety). Ribozyme molecules designed to catalytically cleave target mRNA transcripts can also be used to prevent translation of subject target mRNAs.

While ribozymes that cleave mRNA at site-specific recognition sequences can be used to destroy target mRNAs, the use of hammerhead ribozymes is preferred. Hammerhead ribozymes cleave mRNAs at locations dictated by flanking regions that form complementary base pairs with the target mRNA. Preferably, the target mRNA has the following sequence of two bases: 5'-UG-3'. The construction and production of hammerhead ribozymes is well known in the art.

Gene targeting ribozymes necessarily contain a hybridizing region complementary to two regions, each of at least 5 and preferably each 6, 7, 8, 9, 10, 11, 12, 13, 14, 15, 16, 17, 18, 19 or 20 contiguous nucleotides in length of a target mRNA. In addition, ribozymes possess highly specific endoribonuclease activity, which autocatalytically cleaves the target sense mRNA.

With regard to antisense, siRNA or ribozyme oligonucleotides, phosphorothioate oligonucleotides can be used. Modifications of the phosphodiester linkage as well as of the heterocycle or the sugar may provide an increase in efficiency. Phosphorothioate is used to modify the phosphodiester linkage. An N3'-P5' phosphoramidate linkage has been described as stabilizing oligonucleotides to nucleases and increasing the binding to RNA. Peptide nucleic acid (PNA) linkage is a complete replacement of the ribose and phosphodiester backbone and is stable to nucleases, increases the binding affinity to RNA, and does not allow cleavage by RNAse H. Its basic structure is also amenable to modifications that may allow its optimization as an antisense component. With respect to modifications of the heterocycle, certain heterocycle modifications have proven to augment antisense effects without interfering with RNAse H activity. An example of such modification is C-5 thiazole modification. Finally, modification of the sugar may also be considered. 2'-O-propyl and 2'-methoxyethoxy ribose modifications stabilize oligonucleotides to nucleases in cell culture and in vivo.

Inhibitory oligonucleotides can be delivered to a cell by direct transfection or transfection and expression via an expression vector. Appropriate expression vectors include mammalian expression vectors and viral vectors, into which has been cloned an inhibitory oligonucleotide with the appropriate regulatory sequences including a promoter to result in expression of the antisense RNA in a host cell. Suitable promoters can be constitutive or development-specific promoters. Transfection delivery can be achieved by liposomal transfection reagents, known in the art (e.g., Xtreme transfection reagent, Roche, Alameda, Calif.; Lipofectamine formulations, Invitrogen, Carlsbad, Calif.). Delivery mediated by cationic liposomes, by retroviral vectors and direct delivery are efficient. Another possible delivery mode is targeting using antibody to cell surface markers for the target cells.

Cells

In some embodiments, the one or more polypeptides of Table 1 are in a host cell. The activity of one or more of the polypeptides in Table 1 can be measured in any cell capable of expressing the one or more polypeptides, endogenously or recombinantly. The cells can be prokaryotic or eukaryotic. Exemplary cells include bacterial cells (e.g. *E. coli, Bacillus*), plant cells (e.g., *Arabidopsis, Brassica*, tobacco), insect cells, and mammalian cells. Recombinant expression of polypeptides in different host cell systems is known in the art. See, for example, Sambrook and Russell, *Molecular Cloning: A Laboratory Manual,* 3rd Ed., 2001, Cold Spring Harbor Laboratory Press; Ausubel, et al., *Current Protocols in Molecular Cloning,* 1987-2006, John Wiley Interscience. Appropriate host cells and expression vectors for recombinant expression of one or more of the polypeptides of Table 1 are commercially available, for example, from Invitrogen, Carlsbad, Calif.; Promega, Madison, Wis.; and Qiagen, Valencia, Calif.

In some embodiments, the mammalian cells can be stem cells, typically mesenchymal stem cells (MSCs), pre-osteoblasts, or cells of other lineages such as, for example, pre-adipocytes or myoblasts. Methods for isolation and differentiation of human and animal MSCs have been described (see, e.g., U.S. Pat. Nos. 5,942,225 and 5,486,359; and Pittenger et al., *Science* 284:143 (1999)).

Mesenchymal stem cells ("MSC") are capable of differentiating into the mesenchymal cell lineages, including bone, cartilage, adipose, muscle, stroma, including hematopoietic supportive stroma, and tendon, and play important roles in repair and regeneration (see, e.g., Olsen, 2000, *Ann. Rev. Cell Dev. Biol.* 16:191). MSCs are identified by specific cell surface markers which are identified with unique monoclonal antibodies as described in e.g., U.S. Pat. No. 5,643,736.

Human mesenchymal stem cells (MSC) can be obtained by isolating pluripotent mesenchymal stem cells from other cells in the bone marrow or other MSC source. Bone marrow cells can be obtained from iliac crest, femora, tibiae, spine, rib or other medullary spaces. Other sources of human mesenchymal stem cells include embryonic yolk sac, placenta, umbilical cord, fetal and adolescent skin, blood, adipose tissue, and muscle satellite cells. Typically, cells from a tissue specimen containing mesenchymal stem cells are cultured in growth medium containing growth factors that (1) stimulate mesenchymal stem cell growth without differentiation, and (2) allow for the selective adherence of only the mesenchymal stem cells to a substrate surface. After culturing the cells for a suitable amount of time, non-adherent matter can be removed from the substrate surface, thus providing an expanded population of mesenchymal stem cells. Thus, homogeneous MSC populations can be obtained by positive selection of adherent marrow or periosteal cells which are free of markers associated with either hematopoietic cell or differentiated mesenchymal cells.

The cells to be differentiated into cells of an osteoblast lineage can be derived from any suitable mammal. For example, the cells can be obtained from rodents including, for example, mice, rats, guinea pigs, and rabbits; non-rodent mammals such as, for example, cats, dogs, pigs, sheep, horses, cows, and goats; primates including, for example, chimpanzees and humans. The cells to be differentiated can be primary cells or can be cells maintained in culture. If the cells are maintained in culture, they are contacted, for example, with the compounds/compositions of the present invention between, e.g. the 5th and 15th passage in culture. Techniques and methods for establishing a primary culture of cells for use in the methods of the invention are known to those of skill in the art (see, e.g., Humason, *Animal Tissue Techniques,* 4th Edition, W.H. Freeman and Company (1979), and Ricciardelli, et al., (1989) *In Vitro Cell Dev. Biol.* 25: 1016).

General Culturing Methods

Culture of host cells expressing one or more polypeptides of Table 1 utilizes routine techniques in the field of cell culture. Suitable cell culture methods and conditions can be determined by those of skill in the art using known methodology (see, e.g., Freshney et al., *Culture of Animal Cells* ($4^{th}$ Edition, 2000); Ausubel, et al, supra; Sambrook and Russell, supra; *Insect Cell Cultures: Fundamental and Applied Aspects*, Vlak, et al., eds. 1996, Kluwer Academic Pub.; and Evans, et al., *Plant Cell Culture,* 2003, Taylor & Francis. In general, the cell culture environment includes consideration of such factors as the substrate for cell growth, cell density and cell contract, the gas phase, the medium, and temperature.

Plastic dishes, flasks, or roller bottles can be used to culture cells according to the methods of the present invention. Suitable culture vessels include, for example, multi-well plates, petri dishes, tissue culture tubes, flasks, roller bottles, and the like.

Measuring the Activity or Expression Level of the Polypeptide

The activity of any of the polypeptides listed in Table 1 can be measured according to known methods based the polypeptides' known function. For example, for the polypeptides with known enzymatic activity (e.g., adenylate cyclase, adenosine kinase, serine/threonine kinase, phopholipase), the consumption of substrate and/or the accumulation of product in the enzymatic reaction can be measured. For the polypeptides that are known receptors (e.g., olfactory receptors, integrins, potassium channels), downstream intracellular signaling or binding to ligand can be measured. Such assays are known in the art.

The level of expression of the polypeptides listed in Table 1 can be measured according to methods well known in the art, and described herein. Levels of expression can be measured at the transcriptional and/or translational levels. At the translational level, expression of one or more of the proteins listed in Table 1 can be measured using immunoassays including immunohistochemical staining, western blotting, ELISA and the like with an antibody that selectively binds to the particular protein or a fragment thereof. Detection of the protein using protein-specific antibodies in immunoassays is known in the art (see, e.g., Harlow & Lane, *Using Antibodies: A Laboratory Manual* (1998); Coligan, et al., eds., *Current Protocols in Immunology* (1991-2006); Goding, *Monoclonal Antibodies: Principles and Practice* (3rd ed. 1996); and Kohler & Milstein, *Nature* 256:495-497 (1975). At the transcriptional level, mRNA can be detected by, for example, amplification, e.g., PCR, LCR, or hybridization assays, e.g., northern hybridization, RNAse protection, or dot blotting, all methods known in the art. The level of protein or mRNA is detected, for example, using directly or indirectly labeled detection agents, e.g., fluorescently or radioactively labeled nucleic acids, radioactively or enzymatically labeled antibodies. These assays are well-known to those of skill in the art and described in, e.g., Ausubel, et al., eds., *Current Protocols In Molecular Biology* (1987-2006).

Modulation (e.g., increase or decrease) of transcriptional levels can also be measured using promoter-reporter gene fusion constructs. For example, the promoter region of a gene encoding a polypeptide in Table 1 can be fused (i.e., operably linked) to the coding sequence of a polypeptide that produces a detactable signal. Reporter constructs are well known in the art. Exemplary reporter sequences include, for example, fluorescent proteins (e.g., green, red, yellow), phosphorescent proteins (e.g, luciferase), antibiotic resistance proteins (e.g., β-lactamase), enzymes (e.g., alkaline phosphatase).

Selecting the agent that inhibits the activity of the polypeptide

Inhibition of polypeptide activity of one or more of the polypeptides listed in Table 1 can be measured by comparison to polypeptide activity of the same polypeptide that has not been contacted with one or more candidate agents (inside or outside of a cell). Polypeptide activity that is inhibited will be, e.g., at least about 10%, 25% or 50% less in a treated sample (or reaction mixture) in comparison to an untreated sample. In some embodiments, polypeptide activity can be inhibited at least about 60%, 70%, 80%, 90%, or even completely inhibited, in comparison to polypeptide activity in an untreated sample.

Similarly, inhibition of polypeptide expression of one or more of the polypeptides listed in Table 1, at the transcriptional or translational level, can be measured by comparison to polypeptide expression levels of the same polypeptide in a cell that has not been contacted with one or more candidate agents. In some embodiments, polypeptide expression levels that are inhibited will be, e.g. at least about 10%, 25% or 50% less in a treated cell in comparison to an untreated cell. In some embodiments, polypeptide expression levels can be inhibited at least about 60%, 70%, 80%, 90%, or even completely inhibited, in comparison to polypeptide expression levels in an untreated cell.

In other embodiments, the inhibition of polypeptide activity or expression in the presence of one or more test agents is compared to polypeptide activity or expression level in the presence of a known inhibitor. In this case, same or similar polypeptide activity or expression levels indicates that the one or more test agents are inhibitors.

In some embodiments, selectivity or specificity of the inhibitory agents can be measured by administering the agent to a cell that does not recombinantly or endogenously express any of the polypeptides of Table 1. Agents that specifically inhibit a polypeptide of Table 1 will generally not elicit any detectable response in a cell that does not express the polypeptide.

Detecting Osteogenesis

Induction of osteogenesis, in vitro or in vivo, can be detected using any method known in the art. For example, by detecting expression of osteoblast-specific proteins, detecting expression of bone-specific transcription factors, and detecting changes in bone density. Osteoblast-specific proteins include, for example, alkaline phosphatase (ALP), collagen type I, osteocalcin, and osteoponin (see, e.g., Olsen et al., *Annu. Rev. Cell. Dev. Biol.* 16:191 (2000)). In some embodiments, expression of alkaline phosphatase is detected as an indicator of osteogenesis. Bone specific transcription factors include, for example, Cbfa1/Runx2, gsc, D1x1, D1x5, Msx1, Cart1, Hoxa1, Hoxa2, Hoxa3, Hoxb1, rae28, Twist, AP-2, Mf1, Pax1, Pax3, Pax9, TBX3, TBX4, TBX5, and Brachyury (see, e.g., Olsen et al, 2000, supra). Typically, expression of Cbfa1/Runx2 is detected as an indicator of osteogenesis.

Detection of Osteoblast-Specific Proteins

Expression of osteoblast-specific proteins can be detected by measuring the level of the osteoblast-specific protein or mRNA. The level of particular osteoblast-specific proteins can conveniently be measured using immunoassays including immunohistochemical staining, western blotting, ELISA and the like with an antibody that selectively binds to the particular osteoblast specific proteins or a fragment thereof. Detection of the protein using protein-specific antibodies in immunoassays is known to those of skill in the art (see, e.g., Harlow & Lane, *Using Antibodies: A Laboratory Manual* (1998); Coligan, et al., eds., *Current Protocols in Immunology* (1991-2006); Goding, *Monoclonal Antibodies: Principles and Practice* (3rd ed. 1996); and Kohler & Milstein, *Nature* 256:495-497 (1975). For measurement of mRNA, amplification, e.g., PCR, LCR, or hybridization assays, e.g., northern hybridization, RNAse protection, dot blotting, are preferred. The level of protein or mRNA is detected, for example, using directly or indirectly labeled detection agents, e.g., fluorescently or radioactively labeled nucleic acids, radioactively or enzymatically labeled antibodies. These assays are well-known to those of skill in the art and described in, e.g., Ausubel, et al., eds., *Current Protocols In Molecular Biology* (1987-2006).

Typically, expression of the osteoblast specific-protein, alkaline phosphatase, is used to detect differentiated osteoblasts. Expression of alkaline phosphatase (ALP) is correlated with osteogenesis. ALP hydrolyzes inorganic pyrophosphates to phosphates and promotes the formation of hydroxyapatite crystals in bone matrix. Deactivating mutations of ALP cause osteomalacia, characterized by poorly mineralized bones and frequent bone factures, indicating that ALP plays a significant role in bone formation (see, e.g., Hessle, et al., *Proc. Natl. Acad. Sci. USA* 99:9445(2002)). ALP is a highly active and stable enzyme, making direct assays of its enzymatic activity convenient. In addition, direct histochemical staining of cells can conveniently be used to detect ALP.

Osteogenesis can also be detected by detecting extracellular matrix (ECM) mineralization. Calcium phosphate deposits associated with ECM mineralization can be detected by staining cells with alizarin red solution, as described herein. The extent and intensity of red staining can then be evaluated.

Enzymatic Activity

For direct assays of ALP activity, cells can be plated in multiwell plates (e.g., 96-well, 384-well, 1536-well) and treated with an appropriate amount of one or more candidate agents, either alone or with other growth factors (e.g., BMP-4) and then incubated at 37° C. in 5% $CO_2$. After an appropriate incubation time, the media is removed and lysis buffer is added into each well. After an appropriate incubation time in lysis buffer, alkaline phosphatase substrate solution (e.g., 2'-[2'-benzothiazoyl]-6'-hydroxybenzothiazole phosphate (BBTP)) is added to each well. After an appropriate incubation time at room temperature, the plates are read on a plate reader using methods known in the art.

Immunohistochemical Detection

For direct immunohistochemical staining of cells to detect ALP, cells are seeded in multiwell assay plates at a suitable density and treated with an appropriate amount of a candidate agent, either alone or with other growth factors (e.g., BMP-4) for an appropriate time. Cells are then and fixed in a 10% formalin solution. The fixed cells are washed again and stained with a reagent specific for ALP (e.g., an antibody specific for ALP or a calorimetric ALP substrate) using methods known to those of skill in the art (see, e.g., Harlow & Lane, supra; Coligan, supra; Goding, supra; and Kohler & Milstein, supra). Photographic images of the cells are taken and ALP positive cells are counted manually from the images.

Detection of Bone-Specific Transcription Factors

Expression of bone-specific transcription factors can be detected using reporter gene assays. These assays are well known to those of skill in the art and are described in, e.g., Ausubel, et al., supra. Detecting levels of expression of the bone specific transcription factor Cbfa1/Runx2 can be used to detect osteogenesis. Cbfa1/Runx2 plays an essential role in osteoblast differentiation transgenic mice lacking the Cbfa1/Runx2 gene die shortly after birth due to loss in bone formation (see, e.g., Ducy et al., *Cell* 89:747 (1997) and Komori et al., *Cell* 89:755 (1997)).

Reporter genes including, for example, chloramphenicol acetyltransferase, firefly luciferase, bacterial luciferase, fluorescent proteins (e.g., green, yellow, purple), or β-galactosidase can be used in the reporter gene assays. The reporter construct is typically transiently or stably transfected into a cell. The promoter region of the relevant gene (e.g., Cbfa1/Runx2) is typically amplified by PCR appropriate primers. The resulting PCR product is inserted into a suitable cloning vector, amplified and sequenced. The resulting plasmid is digested with appropriate restriction enzymes and the resulting fragment is inserted into a vector comprising a reporter gene.

Transiently Transfected Cells

For reporter gene assays with transiently transfected cells, the cells can be seeded in a multiwell plate at an appropriate density (e.g., about 30,000 cells/well) in growth medium and incubated for a suitable time. Plasmid DNA is transfected into the cells using a suitable transfection reagent. After a suitable time (e.g., about 8 hours), the transfected cells are plated into multiwell assay plates (e.g., Corning) and treated with an appropriate amount of a candidate agent. The cells are incubated for an appropriate period of time (e.g., several days, e.g. 2, 3 or 4 days), then the reporter gene activity in the cells is assayed using methods known to those of skill in the art.

Stably Transfected Cells

For reporter gene assays with stably transfected cells, the cells can be seeded in a multiwell plate at an appropriate density (e.g., about 30,000 cells/well) in growth medium and incubated for a suitable time. An appropriate amount of reporter plasmid and a vector comprising a selectable marker (e.g., an antibiotic resistance gene) are co-transfected into the cells using an appropriate transfection reagent. After an appropriate incubation time, cells are seeded in culture dishes and an appropriate amount of antibiotic is added to the culture medium. Fresh antibiotic is added at appropriate intervals. The antibiotic resistant colonies are pooled to yield the stably transfected cells. The transfected cells are plated into multiwell assay plates (e.g., Corning) and treated with an appropriate amount of a candidate agent. The cells are incubated for an appropriate period of time (e.g., several days, e.g., 2, 3 or 4 days), then the reporter gene activity in the cells is assayed using methods known to those of skill in the art.

The screening methods of the present invention are well-suited to high throughput screening. Numerous agents can be concurrently screened using multiwell plates (e.g., 96-well, 192-well, 384-well, 768-well, 1536-well, etc.) and automated systems. Automated systems of use in the present screening methods are purchasable from, for example, Thermo LabSystems, Waltham, Mass.; Caliper Life Science, Hopkinton, Mass.; Beckman Coulter, Inc., Fullerton, Calif.; and Invitrogen Corp., Carlsbad, Calif.

IV. Methods of Delivering siRNA Oligonucleotides to a Cell

Compositions comprising one or more siRNA oligonucleotides that inhibit one or more of the polypeptides listed in Table 1 can be delivered to a mammalian cell to promote osteogenesis. The cell can be contacted with one or more siRNA oligonucleotides, in vitro, ex vivo, or in vivo, using methods well known in the art and described herein.

In some embodiments, the mammalian cell is contacted with a composition comprising one or more of the siRNA sequences that inhibit the expression of one or more of the polypeptides listed in Table 1. In one embodiment, the mammalian cell is contacted with a composition comprising one or more siRNA oligonucleotides that inhibit the expression of one or more polypeptides selected from the group consisting of GNAS (Human GNAS complex locus, transcript variant 3 (as of Aug. 9, 2007), isoform b of the alpha subunit of Gs, NM_080426), ADCY8 (adenylate cyclase 8, NM_001115), ADK (adenosine kinase, NM_001123), P2RY11 (purinergic receptor P2Y, G-protein coupled, 11, NM_002566), TBX3 (T-box 3 or ulnar mammary syndrome, NM_005996), BIRC4 (baculoviral IAP repeat-containing 4, NM_001167), BCL2L2 (BCL2-like 2, NM_004050), SLC12A2 (solute carrier family 12, member 2, NM_001046), KCNT1 (potassium channel, subfamily T, member 1, XM_029962.2), GBDR1 (putative glial blastoma cell differentiation-related, NM_016172), DUSP6 (dual specificity phosphatase 6, NM_001946) and MJD (Machado-Joseph disease or ataxin 3, NM_004993). In some embodiments, the mammalian cell is contacted with a composition comprising one or more siRNA oligonucleotide sequences listed in Table 1.

For in vitro of in vivo delivery to a cell, compositions can comprise one or more siRNA molecules for direct transfection, for example, in double-stranded or hairpin configurations. Alternatively, compositions can comprise one or more vectors, for example, plasmid mammalian expression vectors or viral expression vectors, which express one or more siRNA sequences, for example, in double-stranded or hairpin configurations.

For transfection, a composition comprising one or more siRNA molecules (within or without vectors) can comprise a delivery vehicle, including liposomes, for administration to a subject, carriers and diluents and their salts, and/or can be present in pharmaceutically acceptable formulations. Methods for the delivery of nucleic acid molecules are described, for example, in Gilmore, et al., *Curr Drug Delivery* (2006) 3:147-5 and Patil, et al., *AAPS Journal* (2005) 7:E61-E77, each of which are incorporated herein by reference. Delivery of siRNA molecules is also described in several U.S. patent Publications, including for example, 2006/0019912; 2006/0014289; 2005/0239687; 2005/0222064; and 2004/0204377, the disclosures of each of which are hereby incorporated herein by reference. Nucleic acid molecules can be administered to cells by a variety of methods known to those of skill in the art, including, but not restricted to, encapsulation in liposomes, by iontophoresis, by electroporation, or by incorporation into other vehicles, including biodegradable polymers, hydrogels, cyclodextrins (see, for example Gonzalez et al., 1999*, Bioconjugate Chem.,* 10, 1068-1074; Wang et al., International PCT publication Nos. WO 03/47518 and WO 03/46185), poly(lactic-co-glycolic)acid (PLGA) and PLCA microspheres (see for example U.S. Pat. No. 6,447,796 and US Patent Application Publication No. 2002/130430), biodegradable nanocapsules, and bioadhesive microspheres, or by proteinaceous vectors (O'Hare and Normand, International PCT Publication No. WO 00/53722). In another embodiment, the nucleic acid molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives.

Examples of liposomal transfection reagents of us with this invention include, for example: CellFectin, 1:1.5 (M/M) liposome formulation of the cationic lipid N,NI,NII,NIII-tetramethyl-N,NI,NII,NIII-tetrapalmit-y-spermine and dioleoyl phosphatidylethanolamine (DOPE) (GIBCO BRL); Cytofectin GSV, 2:1 (M/M) liposome formulation of a cationic lipid and DOPE (Glen Research); DOTAP (N-[1-(2,3-dioleoyloxy)-N,N,N-tri-methyl-ammoniummethylsulfate) (Boehringer Manheim); Lipofectamine, 3:1 (M/M) liposome formulation of the polycationic lipid DOSPA and the neutral lipid DOPE (GIBCO BRL); and (5) siPORT (Ambion); HiPerfect (Qiagen); X-treme GENE (Roche); RNAicarrier (Epoch Biolabs) and TransPass (New England Biolabs).

In some embodiments, the siRNA sequence is delivered into the cell cloned into a mammalian expression vector. Mammalian expression vectors suitable for siRNA expression are commercially available, for example, from Ambion (e.g. pSilencer vectors), Austin, Tex.; Promega (e.g., GeneClip, siSTRIKE, SiLentGene), Madison, Wis.; Invitrogen, Carlsbad, Calif.; InvivoGen, San Diego, Calif.; and Imgenex, San Diego, Calif. Typically, expression vectors for transcribing siRNA molecules will have a U6 promoter.

In some embodiments, the siRNA sequence is delivered into the cell cloned into a viral expression vector. Viral vectors suitable for delivering siRNA molecules to a cell include adenoviral vectors, adeno-associated vectors, and retroviral vectors (including lentiviral vectors). Viral vectors developed for delivering and expressing siRNA oligonucleotides are commercially available from, for example, GeneDetect, Bradenton, Fla.; Ambion, Austin, Tex.; Invitrogen, Carlsbad, Calif.; Open BioSystems, Huntsville, Ala.; and Imgenex, San Diego, Calif.

V. Administration and Formulation

Agents (e.g., siRNA, organic compounds, polypeptides) that inhibit the activity and/or expression of one or more of the polypeptides listed in Table 1 can be used to induce osteogenesis in mammalian cells. A mammalian cell is contacted with an inhibitory agent, whereupon the mammalian cell differentiates into a cell of an osteoblast lineage. The mammalian cell can be contacted with an inhibitory agent (or a composition thereof) either in vivo, ex vivo (both described below) or in vitro (described above).

In Vivo Induction of Osteogenesis

The inhibitory agents as well as compositions thereof can conveniently be used to induce osteogenesis in vivo. The compounds and compositions of the present invention are administered to an individual, e.g., a mammal such as a human, in an amount effective to induce differentiation of mammalian cells into cells of an osteoblast lineage. In view of their ability to induce osteogenesis, the inhibitory agents are useful for treating bone disorders and diseases, including osteoporosis, rickets, osteomalacia, McCune-Albright syndrome, and Paget's disease. In one embodiment, the compounds and compositions of the present invention are used to treat osteoporosis. In one embodiment, the compounds and compositions of the present invention are used to increase bone density. In one embodiment, the compounds and compositions of the present invention are used to increase bone density and reduce bone loss. In some embodiments, the pharmaceutical composition comprises one or more siRNA oligonucleotides selected from those listed in Table 1.

One of skill in the art will appreciate that the compositions of the present invention can be used alone or in combination with other compounds and therapeutic regimens to induce osteogenesis. For example, the inhibitory agents can be administered in conjunction with bone morphogenetic proteins ("BMPs") or other anti-resorptive medications that affect the bone remodeling cycle. Suitable bone morphogenetic proteins include, for example, BMP-2, BMP-4, and BMP-7. Suitable anti-resorptive medications include, for example, bisphosphonates such as, for example, alendronate sodium and risedronate sodium; hormones, including, for example, calcitonin and estrogens, and selective estrogen receptor modulators, including, for example, raloxifene.

An effective amount of the composition will be determined by the existence, nature, and extent of any adverse side-effects that accompany the administration of the composition; the LD50 of the composition; and the side-effects of the composition at various concentrations. Typically, the amount of the composition administered will range from about 0.01 to about 20 mg per kg, for example about 0.05 to about 15 mg per kg, for example about 0.1 to about 10 mg per kg body weight. Generally, lower doses are initially administered and incrementally increased until an appropriately efficacious dose is reached.

The compositions can be administered, for example, orally or parenterally, for example, intravenously, intramuscularly, intraperitoneally, subcutaneously, or directly into bone tissue. Oral administration is the preferred method of administration. The formulations of compounds can be presented in unit-dose or multi-dose sealed containers, such as ampoules and vials. In some embodiments, the compositions are delivered by an implantable pump.

The compositions of the present invention are typically formulated with a pharmaceutically acceptable carrier before administration to an individual or subject. Pharmaceutically acceptable carriers are determined, in part, by the particular composition being administered, as well as by the particular method used to administer the composition. Accordingly, there are a wide variety of suitable formulations of pharmaceutical compositions of the present invention (see, e.g., *Remington: The Science and Practice of Pharmacy*, University of the Sciences in Philadelphia, $21^{st}$ Edition, 2005, Lippincott, Williams & Wilkins).

Formulations suitable for oral administration can consist of (a) liquid solutions, such as an effective amount of the compound or composition suspended in diluents, including water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of the following: lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compositions of the present invention can be in formulations suitable for other routes of administration, such as, for example, intravenous infusion, intraperitoneally, subcutaneously, intramuscularly, directly into bone. The formulations include, for example, aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can be prepared from sterile powders, granules, and tablets.

The dose administered to a patient, in the context of the present invention should be sufficient to effect a beneficial therapeutic response in the patient over time. For example, if the compositions of the present invention are administered to treat or prevent osteoporosis, the dose administered to the patient should be sufficient to prevent, retard, or reverse decreases in bone density. The dose will be determined by the efficacy of the particular composition employed and the condition of the patient, as well as the body weight or surface area of the patient to be treated. The size of the dose also will be determined by the existence, nature, and extent of any adverse side-effects that accompany the administration of a particular composition in a particular patient.

The inhibiting agents, including siRNA compositions, can be administered once or repeatedly, as needed. For example, the inhibitory agents can be administered at regular intervals (e.g., twice daily, daily, twice weekly, weekly, monthly) for an extended period of time (e.g., 7 days, 14 days, 21 days, 1 month, 2 months, 3 months, 6 months, 9 months, 12 months, or more). Administration of the inhibitory agents can be more or less often over time, as needed.

Ex Vivo Induction of Osteogenesis

Differentiated osteoblast cells can be administered to a subject by any means known to those of skill in the art. In one embodiment of the invention, differentiated osteoblast cells on an intact solid support (e.g., a three-dimensional matrix or a planar surface) can be administered to the subject, e.g., via surgical implantation. Alternatively, the differentiated osteoblast cells can be detached from the matrix, i.e., by treatment with a protease, before administration to the subject, e.g., intravenously, subcutaneously, intramuscularly, intraperitoneally or directly into bone.

In some embodiments of the present invention, mesenchymal stem cells are extracted from a human and subsequently contacted with an agent that inhibits one or more of the polypeptides of Table 1 for proliferation and differentiation into cells of an osteoblastic cell lineage. Cells can be extracted from the subject to be treated, i.e., autologous (thereby avoiding immune-based rejection of the implant), or can be from a second subject, i.e., heterologous. In either case, administration of cells can be combined with an appropriate immunosuppressive treatment.

Osteoblast cells differentiated according to the methods of the present invention may be administered to a subject by any means known in the art. Suitable means of administration include, for example, intravenous, subcutaneous, intramuscular, intraperitoneal, into bone and surgical implantation.

The cells may be in formulations suitable for administration, such as, for example, aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can be prepared from sterile powders, granules, and tablets.

For surgical implantation, differentiated cells can be left on an intact solid support, e.g., a three-dimensional matrix or planar surface. The matrix or planar surface is surgically implanted into the appropriate site in a subject. For example, a patient needing a bone graft can have differentiated cells on an intact solid support surgically implanted.

In determining the effective amount of the cells to be administered in the treatment or prophylaxis of conditions owing to diminished or aberrant osteoblasts, the physician evaluates cell toxicity, transplantation reactions, progression of the disease, and the production of anti-cell antibodies. For administration, osteoblast cells differentiated according to the methods of the present invention can be administered in an amount effective to provide osteoblasts to the subject, taking into account the side-effects of the osteoblasts at various concentrations, as applied to the mass and overall health of the patient. Administration can be accomplished via single or divided doses.

Detection of Bone Density

To assess the effect of the compositions of the present invention on bone density, a baseline measurement of bone density in an individual who will receive treatment may taken. Bone density is periodically measured at suitable intervals during and after administration of an inhibitory agent of the invention (e.g., one or more siRNA olignucleotides selected from those listed in Table 1). Methods and devices for measuring bone density are well known in the art and are described in, e.g., U.S. Pat. Nos. 6,436,042; 6,405,068; 6,320,931; 6,302,582; 6,246,745; 6,230,036; 6,213,934; 6,102,567; 6,058,157; 5,898,753; 5,891,033; 5,852,647; 5,817,020; 5,782,763; 5,778,045; 5,749,363; 5,745,544; 5,715,820; 5,712,892; 5,572,998; and 5,480,439.

VI. Therapeutic and Diagnostic Uses

The methods and compositions of the present invention find use in treating bone disorders and diseases resulting from defective or deficient osteoblast formation. Exemplified bone diseases that develop as a result of a deficient or defective osteoblast differentiation include, for example, osteoporosis, rickets, osteomalacia, McCune-Albright syndrome, and Paget's disease. See, for example, Chapters 333-334 of Kasper, et al., *Harrison's Principles of Internal Medicine,* $16^{th}$ Edition, 2004, McGraw-Hill.

The present methods are also useful for, inter alia, in vitro bone culturing and analysis of osteogenesis.

The following examples are intended to illustrate, not limit, the present invention.

EXAMPLES

Example 1

Experimental Procedures

Cell Culture, Transfection and High Throughput Screen

The human mesenchymal stem cells (hMSCs, PT-2501) were purchased from Cambrex Inc. and cultured as instructed by the supplier. Cells were expanded to passage 5 before being used for siRNA library screen. Briefly, diluted Xtreme-siRNA transfection reagent (cat# 4 476 115 00, Roche) (0.12 µl Xtreme in 14 µl DMEM) was mixed with pre-spotted siRNA (14 ng/well) in each well of 384-well plates for one hour. Cells (4000/well) in 60 µl media (no antibiotics) were then added using automated dispenser (Multidrop 384, Thermo LabSystems) (siRNA final concentration at around 15 nM). Transfection was allowed to continue for 8 hours before first media renewal. After 7 days of culture, cells were stained for alkaline phosphatase (ALP) activity (cat# 86R-1KT, Sigma). Post-screen assays were done in 96-well plates and siRNA was transfected at the concentration of 30 nM at the cell density of 8000 cells/well. CRE decoy oligonucleotide and control oligonucleotide (phosphorothioate bond modification on all nucleotides) (Park, Y. G. et al., *J Biol Chem* 274:1573-1580 (1999)) were transfected into cells similarly as siRNA using Xtreme-siRNA transfection reagent, except that the final DNA concentration was 90 nM. Control siRNA (siCon) used in the screen contains a pool of 50 scrambled sequences that have at least 4 mismatches to known human transcripts and ESTs, and at least 2-3 mismatches to the whole human genome. siCon used in target characterization after primary screen was purchased from Dharmacon (D-001210-01-05), which was bioinformatically designed to have >=4 mismatches with known human and mouse genes. siTOX was also purchased from Dharmacon (D-001500-01-05).

```
siCBFA1:
                                        (SEQ ID NO:1)
UAGUAGAGAUAUGGAGUGCtg (antisense);
                                        (SEQ ID NO:2)
GCACUCCAUAUCUCUACUAtt (sense).

CRE decoy 24-mer palindrome:
                                        (SEQ ID NO:3)
5'-TGACGTCATGACGTCATGACGTCA-3'.

CRE mismatch control:
                                        (SEQ ID NO:4)
5'-TGTGGTCATGTGGTCATGTGGTCA-3'.
```

Calcium Phosphate Staining

Cells were rinsed with PBS twice, stained in alizarin red solution (cat# vw3611-2, VWR) for 8 minutes at room temperature, washed with PBS again, fixed in 10% formalin solution (cat# HT-5014, Sigma) for 20 minutes, then rinsed with water and air dried.

Oil Red O staining

Cells were rinsed with PBS twice, fixed in 10% formalin solution for 20 minutes, rinsed with PBS twice and $dH_2O$ once, washed with propylene glycol for 5 minutes, and stained with Oil red in propylene glycol (I2722A, Newcomer Supply) for 30 minutes. Cells were then washed with 85% propylene glycol for 5 minutes, rinsed with dH2O 3 times and preserved in 50% glycerol.

Compound Treatment

8-CPT-cAMP, Na (cat# 116812), 5-Iodotubercidin (cat# 407900), Prostaglandin E2 (PGE2, cat# 538904), SB 202190 (cat# 559388) and U0126 (cat# 662005) were purchased from Calbiochem; N6,2'-O-Dibutyryl-cAMP (cat# D0260-5MG), forskolin (cat# F6886), ascorbic acid 2-phosphate (cat# 49752-10G), β-glycerophosphate (G-6251), dexamethasone (D8893), 3-isobutyl-1-methylxanthine (IBMX, I5879) and Insulin (I 9278) were purchased from Sigma/Aldrich/Fluka.

RNA preparation and RT-PCR

Total RNA from each sample was prepared from around 5×10(4) cells using RNAeasy mini kit from Qiagen and further treated with Turbo DNA-Free (cat# 1907, Ambion) to prevent DNA contamination. Reverse transcription was carried out using SuperScript First-Strand Synthesis System for RT-PCR (cat# 11904-018, Invitrogen) or Qiagen OneStep RT-PCR kit (cat# 210210) as instructed. PCR primers used were as follows:

```
GAPDH:
Forward
                                        (SEQ ID NO:5)
5'-GAA GGT GAA GGT CGG AGT C-3';
```

-continued

Reverse
(SEQ ID NO:6)
5'-GAA GAT GGT GAT GGG ATT TC-3'.

ALPL:
Forward
(SEQ ID NO:7)
5'-TGG AGC TTC AGA AGC TCA ACA CCA-3';

Reverse
(SEQ ID NO:8)
5'-ATC TCG TTG TCT GAG TAC CAG TCC-3'.

RUNX2:
Forward
(SEQ ID NO:9)
5'-TCT TCA CAA ATC CTC CCC-3';

Reverse
(SEQ ID NO:10)
5'-TGG ATT AAA AGG ACT TGG TG-3'.

OSX:
Forward
(SEQ ID NO:11)
5'-CCT ATG TAC CAG GAG TAA TGA ATA G-3';

Reverse
(SEQ ID NO:12)
5'-CTC CTA GCT CTT TAA GTT CTT TCT C-3'.

DLX5:
Forward
(SEQ ID NO:13)
5'-GAG AAG GTT TCA GAA GAC TCA GTA-3';

Reverse
(SEQ ID NO:14)
5'-CTA GAA CAG CAA AAC ACA GTA GTC-3'.

BSP:
Forward
(SEQ ID NO:15)
5'-GAG AAT ACC ACA CTT TCT GCT AC-3';

Reverse
(SEQ ID NO:16)
5'-AAG TAG CTG TAC TCA TCT TCA TAG G-3'.

MJD:
Forward
(SEQ ID NO:17)
5'-AGC ACA ACT AAA AGA GCA AAG AGT C-3';

Reverse
(SEQ ID NO:18)
5'-CTC ATA GCA TCA CCT AGA TCA CTC C-3'.

BIRC4:
Forward
(SEQ ID NO:19)
5'-GTT TCA GCA TCA ACA CTG GC-3';

Reverse
(SEQ ID NO:20)
5'-TCC GTG CTT CAT AAT CTG CC-3'.

P2RY11:
Forward
(SEQ ID NO:21)
5'-GTG TCC ACC CTC TAC TCT ACA T-3';

Reverse
(SEQ ID NO:22)
5'-CTC CAC TCT CTC TAC TTG GTT CT-3'.

-continued

SLC12A2:
Forward
(SEQ ID NO:23)
5'-GGT GTC TAT CTC TTG ACC TTG T-3';

Reverse
(SEQ ID NO:24)
5'-GAC CTG GTG TCT AGT GTT AAG TG-3'.

TBX3:
Forward
(SEQ ID NO:25)
5'-ATA ACT GAG ATT GCT GTG GG-3';

Reverse
(SEQ ID NO:26)
5'-AGA GAG GGG GAA AAA TAC AG-3'.

BCL212:
Forward
(SEQ ID NO:27)
5'-GCT GAG GCA GAA GGG TTA TG-3';

Reverse
(SEQ ID NO:28)
5'-ATA GAG CTG TGA ACT CCG CC-3'.

KCNT1:
Forward
(SEQ ID NO:29)
5'-TTC TGG AAG TTA GAA GCA GC-3';

Reverse
(SEQ ID NO:30)
5'-ACC GTA CAA ACC AGT AAG GA-3'.

ADK:
Forward
(SEQ ID NO:31)
5'-CCA GAG TCA GTA TTA AAG GTG G-3';

Reverse
(SEQ ID NO:32)
5'-GAG ACC AGT TGA GAC AGA AAA CAD CY-3'.

$G_s\alpha$:
Forward
(SEQ ID NO:33)
5'-ATC TCT GTG ATC CTG TTC CTC-3';

Reverse
(SEQ ID NO:34)
5'-GTG AAA TGA GGG TAG CAG TAG T-3'.

DUSP6:
Forward
(SEQ ID NO:35)
5'-TAG ATA CAG GCA GTA GGT TTG C-3';

Reverse
(SEQ ID NO:36)
5'-CTC TCT TTG GCT CCT CTA TAT G-3'.

GBDR1:
Forward
(SEQ ID NO:37)
5'-GAG AGA CTT CCA GAC AGA ACT C-3';

Reverse
(SEQ ID NO:38)
5'-CAT CTA TCA CCT CTT TCT CGT C-3'.

PLZF:
Forward
(SEQ ID NO:39)
5'-TCT CAA ACG CCA CCT GCG CTC ACA T-3';

Reverse
(SEQ ID NO:40)
5'-CAC TGG CAG GGC GAG GCG CCG TTG T-3'.

Western Blot

Cell lyses buffer contains 20 mM Tris pH8.0, 1 mM EDTA, 150 mM NaCl and 0.5% NP-40, and before usage, protease inhibitor cocktail (Cat# p8340, Sigma, 1:100 dilution) and phosphatase inhibitor cocktail 2 (Cat# p5726, sigma, 1:100 dilution) were added. Proteins (60 μg/well) were separated in 12% Novex Tris-Glycine gel (Cat# EC6008 box, Invitrogen) and transferred to Nitrocellulose membrane (Cat# LC2001, Invitrogen) using the XCell II blot module system (Cat# EI9051, Invitrogen). The membrane was blocked in 5% milk/PBST for 1 hour at room temperature, incubated over night at 4 degree with primary antibody, washed 3 times with PBST (0.05% Tween 20 in PBS), followed by one hour incubation with secondary antibody in 5% milk/PBST and 3 times wash with PBST at room temperature. For antibody against pCREB however, PBST was substituted with PBS in all steps except for the last one. Antibody-bound proteins were detected utilizing ECL Western blotting detection reagent (Amersham Biosciences).

Anti-phospho-CREB was purchased from Upstate Biotechnology (cat# 06-519); Anti-phospho-p38 was purchased from Cell signaling technology (cat# 9910).

Results

Figure 2:
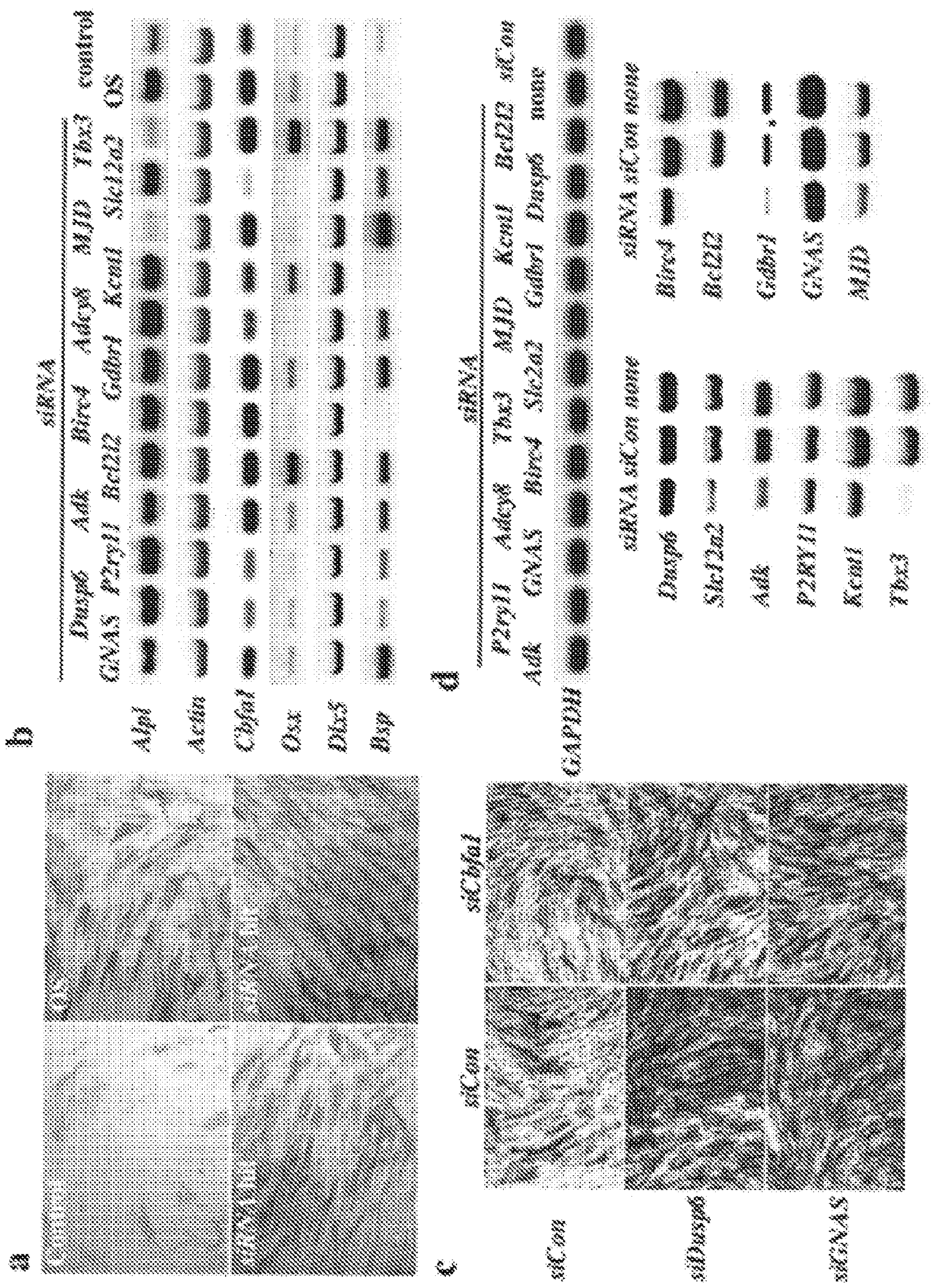
FIG. 2 illustrates the identification and confirmation of siRNA hits that induced osteogenic differentiation of hMSCs: a. Alkaline phosphatase activity, as indicated by the staining, was up regulated in the hit siRNA transfected or OS treated cells as compared to the control siRNA transfected cells. b. Expression of the early (Cbfa 1 and Osx but not D1x5) and late (Bsp) osteogenic markers was differentially induced in different hit siRNA or OS treated samples prepared 3 days after transfection or OS treatment. c. ALP activity was reduced in the hit siRNA and siCbfa 1 co-transfected cells as compared to the hit siRNA and siCon co-transfected cells. d. Expression knockdown of targeted genes was observed at 36 hours after siRNA transfection. OS, osteogenic differentiation media; Osx, osterix.

After testing of various commercially available lipofection reagents, we found that Xtreme siRNA transfection reagent from Roche was the most effective in hMSCs, providing over 90% transfection efficiency and minimum cellular toxicity (FIG. 1). This highly effective siRNA transfection method was then implemented into a high throughput screen that was based on an enzymatic assay of alkaline phosphatase (ALP), an early marker for osteogenic differentiation (Rodan, G. A. et al., *Cell* 89:677-680 (1997)). Fifty five hits that gave rise to a significant increase of ALP activity on day 7 after siRNA transfection in hMSCs were identified and confirmed (FIG. 2*a* & Table 1).

TABLE 1

| Target ID SEQ ID NOS: (nucleic acid/ amino acid | Symbol | 5pDNA | siRNA sequence | 3pDNA | SEQ ID NO: (siRNA, siRNA/DNA) | Definition |
|---|---|---|---|---|---|---|
| NM_000516 (SEQ ID NOS: 151 and 152) | GNAS | AA | UCGAAGAUUGAGGACUACU | TT | 41, 42 | GNAS complex locus |
| NM_001115 (SEQ ID NOS: 153 and 154) | ADCY8 | CA | GGAGAUCAACAAGCAUUCA | TT | 43, 44 | adenylate cyclase 8 |
| NM_001123 (SEQ ID NOS: 155 and 156) | ADK | CA | GCCACACAAAGCAGCAACA | TT | 45, 46 | adenosine kinase |
| NM_002566 (SEQ ID NOS: 157 and 158) | P2RY11 | CA | UGCGGGUGCUCAACGUGGA | TG | 47, 48 | purinergic receptor P2Y, G-protein coupled, 11 |
| NM_030959 (SEQ ID NOS: 159 and 160) | OR12D3 | AA | UUGGCCUGUAGUGACACAU | TA | 49, 50 | olfactory receptor, family 12, subfamily D, member 3 |
| NM_001005170 (SEQ ID NOS: 161 and 162) | OR52I2 | TA | UGGCAUGAGGACCAAACAA | TT | 51, 52 | Olfactory receptor |
| NM_001005238 (SEQ ID NOS: 163 and 164) | OR51G2 | CA | UCCCGGGCAACUGCACAAU | TC | 53, 54 | Olfactory receptor |
| XM_291440.1 (SEQ ID NOS: 165 and 166) | OR2M4 | CA | UGAGACCAGCUUCUAAACA | TA | 55, 56 | olfactory receptor |
| NM_001005221 (SEQ ID NOS: 167 and 168) | OR4F29 | TA | CUGGCCAGUCUCUCCUUCA | TT | 57, 58 | Olfactory receptor |
| NM_002209 (SEQ ID NOS: 169 and 170) | ITGAL | CA | GACCUGCAGGAUGACACAU | TT | 59, 60 | integrin, alpha L |
| NM_002203 (SEQ ID NOS: 171 and 172) | ITGA2 | GC | UGCUGGUGUUAGCGCUCAG | TC | 61, 62 | integrin, alpha 2 (CD49B, alpha 2 sub-unit of VLA-2 receptor) |

TABLE 1-continued

| Target ID SEQ ID NOS: (nucleic acid/ amino acid | Symbol | 5pDNA | siRNA sequence | 3pDNA | SEQ ID NO: (siRNA, siRNA/DNA) | Definition |
|---|---|---|---|---|---|---|
| NM_002203 (SEQ ID NOS: 171 and 172) | ITGA2 | TG | CUGCUGGUGUUAGCGCUCA | GT | 63, 64 | integrin, alpha 2 (CD49B, alpha 2 sub-unit of VLA-2 receptor) |
| NM_021146 (SEQ ID NOS: 173 and 174) | CDT6 | CA | GCACCAAGGACAAGGACAA | TG | 65, 66 | angiopoietin-like factor |
| NM_012098 (SEQ ID NOS: 175 and 176) | ANGPTL2 | AA | UGCGGGUGACUCCUUUACA | TG | 67, 68 | angiopoietin-like 2 |
| XM_029962.2 (SEQ ID NOS: 177 and 178) | KCNT1 | CA | UGCGAGCCAAGAUGGACAA | TG | 69, 70 | potassium channel, subfamily T, member 1 |
| NM_001046 (SEQ ID NOS: 179 and 180) | SLC12A2 | AA | CCUCUUCGUGGCUACAUCU | TA | 71, 72 | solute carrier family 12 (sodium/potassium/ chloride transporters), member 2 |
| NM_018843 (SEQ ID NOS: 181 and 182) | MCFP | AA | UGGACUCAUGGAUCAUCUA | TG | 73, 74 | mitochondrial carrier family protein |
| NM_000633 (SEQ ID NOS: 183 and 184) | BCL2 | CA | UGUGUGUGGAGAGCGUCAA | CC | 75, 76 | B-cell CLL/lymphoma 2 |
| NM_004050 (SEQ ID NOS: 185 and 186) | BCL2L2 | CA | CCCAGGUCUCCGAUGAACU | TT | 77, 78 | BCL2-like 2 |
| NM_016346 (SEQ ID NOS: 187 and 188) | NR2E3 | CA | GCAGCAGCGGGAAGCACUA | TG | 79, 80 | nuclear receptor sub-family 2, group E, member 3 |
| NM_016346 (SEQ ID NOS: 187 and 188) | NR2E3 | CA | GAGGAUGCUGAUGAGAAUA | TT | 81, 82 | nuclear receptor sub-family 2, group E, member 3 |
| NM_022571 (SEQ ID NOS: 189 and 190) | HUMNPIIY20 | CA | CGCUCAGCGUGGCGCUCAU | CT | 83, 84 | putative leukocyte platelet-activating factor receptor |
| NM_002985 (SEQ ID NOS: 191 and 192) | CCL5 | AA | UGGGUUCGGGAGUACAUCA | AC | 85, 86 | chemokine (C-C motif) ligand 5 |
| NM_001946 (SEQ ID NOS: 193 and 194) | DUSP6 | AA | CUGUGGUGUCUUGGUACAU | TG | 87, 88 | dual specificity phosphatase 6 |
| NM_005990 (SEQ ID NOS: 195 and 196) | STK10 | TA | GAGCACGAAACCCAGAAAC | TG | 89, 90 | serine/threonine kinase 10 |
| NM_022355 (SEQ ID NOS: 197 and 198) | LOC64174 | CA | UCGGGAUUGGUGGAGAUUA | TG | 91, 92 | putative dipeptidase |
| NM_012400 (SEQ ID NOS: 199 and 200) | PLA2G2D | TA | CCAGAAGCGACUGCGUUUC | TA | 93, 94 | phospholipase A2, group IID |
| NM_178134 (SEQ ID NOS: 201 and 202) | CYP4Z1 | CA | UCCCUAUGCCUUCAUACCA | TT | 95, 96 | Cytochrome P450 |
| NM_001354 (SEQ ID NOS: 203 and 204) | AKR1C2 | CA | AGCCAGGGCUCAAGUACAA | GC | 97, 98 | aldo-keto reductase family 1, member C2 |

TABLE 1-continued

| Target ID SEQ ID NOS: (nucleic acid/ amino acid | Symbol | 5pDNA | siRNA sequence | 3pDNA | SEQ ID NO: (siRNA, siRNA/DNA) | Definition |
|---|---|---|---|---|---|---|
| NM_000255 (SEQ ID NOS: 205 and 206) | MUT | TA | GCUGAGGGAAUACCUAAAC | TT | 99, 100 | methylmalonyl Coenzyme A mutase |
| NM_000787 (SEQ ID NOS: 207 and 208) | DBH | GA | CCACGUACUGGUGCUACAU | TA | 101, 102 | dopamine beta-hydroxy-lase (dopamine beta-monooxygenase) |
| NM_012253 (SEQ ID NOS: 209 and 210) | TKTL1 | TA | UCCGUGUCAUCGACCUGUU | TA | 103, 104 | transketolase-like 1 |
| NM_000137 (SEQ ID NOS: 211 and 212) | FAH | AA | CUUCGGAAGUGUGCAUUCA | TC | 105, 106 | fumarylacetoacetate hydrolase (fumarylacetoacetase) |
| NM_006502 (SEQ ID NOS: 213 and 214) | POLH | TA | UGCCAGAACACAUGGACUA | TC | 107, 108 | polymerase (DNA directed), eta |
| NM_078487 (SEQ ID NOS: 215 and 216) | CDKN2B | AA | GGUGCGACAGCUCCUGGAA | GC | 109, 110 | cyclin-dependent kinase inhibitor 2B (p15, inhibits CDK4) |
| NM_003671 (SEQ ID NOS: 217 and 218) | CDC14B | CA | GAGCAGCCUUCUCCAAACU | TC | 111, 112 | CDC14 cell division cycle 14 homolog B (*S. cerevisiae*) |
| NM_004993 (SEQ ID NOS: 219 and 220) | MJD | AA | CAGAUGCAUCGACCAAAAC | TT | 113, 114 | Machado-Joseph disease (ataxin 3) |
| NM_001167 (SEQ ID NOS: 221 and 222) | BIRC4 | CA | UGUGCUACACAGUCAUUAC | TT | 115, 116 | baculoviral IAP repeat-containing 4 |
| NM_004403 (SEQ ID NOS: 223 and 224) | DFNA5 | AA | AGUCUUCCCACUGCUUCUU | TG | 117, 118 | deafness, autosomal dominant 5 |
| NM_002636 (SEQ ID NOS: 225 and 226) | PHF1 | CA | UGCUGGGUAUGAAGCUUUC | TC | 119, 120 | PHD finger protein 1 |
| NM_005996 (SEQ ID NOS: 227 and 228) | TBX3 | AA | UGCCAAAGAGGAUGUACAU | TC | 121, 122 | T-box 3 (ulnar mammary syndrome) |
| NM_014819 (SEQ ID NOS: 229 and 230) | PJA2 | AA | CAGGUAGUGAGGCCAAAAG | TT | 123, 124 | praja 2, RING-H2 motif containing |
| AF447582 (SEQ ID NOS: 231 and 232) See also, NM_001025105 (SEQ ID NOS: 233 and 234) and NM_001892 (SEQ ID NOS: 235 and 236) | HLCDGP1 | TA | UGCUAGCAUCAUGCACAUC | TT | 125, 126 | down-regulated in lung cancer (PRO2975, casein kinase 1, alpha 1 (CSNK1A1)) |
| NM_016172 (SEQ ID NOS: 237 and 238) | GBDR1 | AA | CCCGAAAACAUUGCUAGCA | TT | 127, 128 | putative glialblastoma cell differentiation-related |
| XM_292126.2 (SEQ ID NOS: 239 and 240) | LOC341549 | CA | GAGCAGAUGGCCUGGAGAU | TC | 129, 130 | similar to semaphorin cytoplasmic domain-associated protein 3B |

TABLE 1-continued

| Target ID SEQ ID NOS: (nucleic acid/ amino acid | Symbol | 5pDNA | siRNA sequence | 3pDNA | SEQ ID NO: (siRNA, siRNA/DNA) | Definition |
|---|---|---|---|---|---|---|
| NM_080873 (SEQ ID NOS: 241 and 242) | ASB11 | CA | UGGAGAUCCUGCUGGCAAA | TA | 131, 132 | ankyrin repeat and SOCS box-containing 11 |
| XM_497244 (SEQ ID NOS: 243 and 244) | IFIT-1 | AA | AUCCAAAAGAUGCACACAU | TA | 133, 134 | similar to Interferon-induced protein with tetratricopeptide repeats 1 (IFIT-1) |
| NM_000095 (SEQ ID NOS: 245 and 246) | COMP | CA | CGGUCACGGAUGACGACUA | TG | 135, 136 | cartilage oligomeric matrix protein (pseudo-achondroplasia) |
| NM_178833 (SEQ ID NOS: 247 and 248) | LOC133308 | AA | CCAACAGAAGGAAGUAUUC | TT | 137, 138 | hypothetical protein BC009732 |
| NM_153361 (SEQ ID NOS: 249 and 250) | MGC42105 | AA | CGGAUAGGCUUCUACCGAA | TT | 139, 140 | hypothetical protein MGC42105 |
| NM_032921 (SEQ ID NOS: 251 and 252) | MGC15875 | AA | UGUGCUUCAGCCUGGACAA | TG | 141, 142 | hypothetical protein MGC15875 |
| NM_152267 (SEQ ID NOS: 253 and 254) | FLJ38628 | CA | GCACUUUCGAGUGCAACAU | CT | 143, 144 | hypothetical protein FLJ38628 |
| BF591642 (SEQ ID NO: 255) gi:11683966 See also, AK096500 (SEQ ID NO: 256) and DA771261. (SEQ ID NO: 257) | IMAGE: 3568335 | CA | UGGGCUCACUCUGCAACCA | GG | 145, 146 | clone IMAGE:3568335 3' See also, cDNA FLJ39181 fis, clone OCBBF2004235. |
| XM_054936.7 (SEQ ID NOS: 258 and 259) | LOC114971 | TA | CCUGAUUCAGGUGCACAAA | TG | 147, 148 | hypothetical protein LOC114971 |
| XM_045308.6 (SEQ ID NOS: 260 and 261) | DKFZP727G051 G051 | AA | GGCAUUGACAGCCACACAU | TT | 149, 150 | DKFZP727G051 protein |

Figure 3:
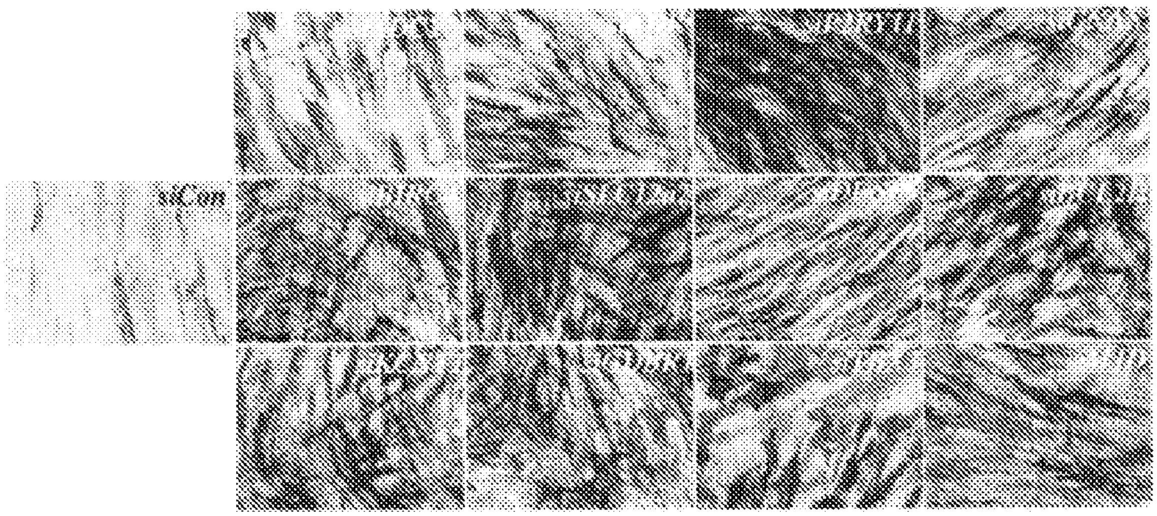
FIG. 3 illustrates enhanced alkaline phosphatase activity staining in hMSCs transfected with the picked hit siRNAs as compared to cells transfected with siCon.

Among the primary siRNA hits, the corresponding genes encode proteases, kinases, ion channels, protein receptors, ligands, transcription factors, extracellular matrix proteins and hypothetical proteins etc., some of which are members of the same gene family (integrin family, angiopoietin family, adenylate cyclase family and olfactory receptor family) (Table 1). While the majority of the identified genes have not been implicated in bone development, two genes, TBX3 (T-box 3) and GNAS, have been found to cause skeletal abnormalities when mutated in mouse and human, respectively (Bianco, P. et al., *J Bone Miner Res* 15:120-128 (2000); Davenport, T. G. et al., *Development* 130:2263-2273 (2003); Eddy, M. C. et al., *J Bone Miner Res* 15:2074-2083 (2000); Shore, E. M. et al., *N Engl J Med* 346:99-106 (2002); Weinstein, L. S. et al., *N Engl J Med* 325:1688-1695 (1991)). To verify the screen, we picked twelve targeted genes (FIG. 3), including GNAS (Human GNAS complex locus, transcript variant 2, isoform b of the alpha subunit of Gs, NM__080426), ADCY8 (adenylate cyclase 8, NM__001115), ADK (adenosine kinase, NM__001 123), P2RY11 (purinergic receptor P2R, G-protein coupled, 11, NM__002566), TBX3 (T-box 3 or ulnar mammary syndrome, NM__005996), BIRC4 (baculoviral IAP repeat-containing 4, NM__001167), BCL212 (BCL2-like 2, NM__004050), SLC12A2 (solute carrier family 12, member 2, NM001046), KCNT1 (potassium channel, subfamily T, member 1, XM__029962.2), GBDR1 (putative glial blastoma cell differentiation-related, NM__016172), DUSP6 (dual specificity phosphatase 6, NM__001946) and MJD (Machado-Joseph disease or ataxin 3, NM__004993), to further characterize their function in osteogenic differentiation of hMSCs.

To confirm that the induced ALP activity was derived from the bone-specific isozyme ALPL (Weiss, M. J. et al., *Proc Natl Acad Sci USA* 83:7182-7186 (1986)), RT-PCR analysis using the ALPL specific primers was carried out on hMSC samples collected on day 4 after siRNA transfection. As shown in FIG. 2*b*, similar to samples treated with the optimal osteogenic inducing media (OS, a mix of 0.05 mM Ascorbic acid 2-phosphate, 10 mM glycophosphate and 0.1 μM Dexamethasone in cell culture media) (Pittenger, M. F. et al., *Science* 284:143-147 (1999)), samples transfected with the hit siRNAs, except for siTBX3 and siMJD, generated increased ALPL transcripts as compared to the control samples transfected with nonspecific siRNAs (siCon). To further confirm the osteogenic identity of the transfected hMSCs, we also examined the expression of several additional early (CBFA1, DLX5, Osterix/OSX) and one late (Bone-specific Sialoprotein or BSP) stage osteogenic markers (Acampora, D. et al., *Development* 126:3795-3809 (1999); Ducy, P. et al., *Cell* 89:747-754 (1997); Nakashima, K. et al., *Cell* 108:17-29 (2002); Wang, D. et al., *J Bone Miner Res* 14:893-903 (1999)). Except for DLX5, which appeared unchanged among all tested samples, CBFA1, OSX and BSP were differentially up regulated in the hit siRNA and OS treated samples as compared to the siCon treated sample (FIG. 2*b*), suggesting that the osteogenic specification of hMSCs induced by the different hit siRNAs has progressed to different stages. CBFA1/RUNX2, a master transcription factor required for bone cell fate determination and maturation in mouse (Ducy, P. et al., *Cell* 89:747-754 (1997)), is normally expressed in hMSCs (FIG. 2*b*).

To examine whether the hit siRNA induced osteogenic cell fate commitment requires the function of CBFA 1, each hit siRNA was co-transfected with either the CBFA 1-specific siRNA or the siCon in hMSCs, and ALP activity was examined. While the co-treatment with the siCon did not cause any noticeable change in ALP activity as compared to the single hit siRNA treatment, the co-treatment with the CBFA1 siRNA reduced the level of ALP activity induced by the hit siRNAs or osteogenic inducing media (OS) (FIG. 2*c*), suggesting that the hit siRNA induced osteogenic cell fate commitment in hMSCs also requires the function of CBFA 1. To confirm that the induced ALPL expression was not caused by off-target effect from the transfected hit siRNAs, RT-PCR was performed on corresponding siRNA targeted genes with the RNA samples prepared at 36 hours after siRNA transfection. As compared to the control samples, the reduced transcript level of the targeted gene in the corresponding hit siRNA transfected hMSCs affirmed the specificity (FIG. 2*d*). In addition, the knockdown of the targeted genes was also observed at 72 hours after siRNA transfection.

Figure 4:
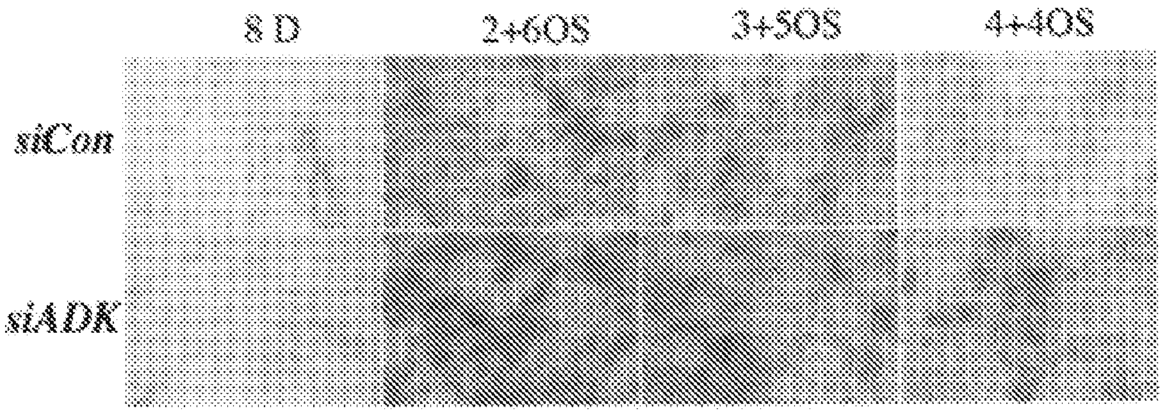
FIG. 4 illustrates sequential treatment of hMSCs with siADK or siCon followed by the OS demonstrated the enhancing effect of siADK vs. siCon on bone cell maturation. 2+6OS, OS treatment was started 2 days after siRNA transfection and continued for 6 days. Similar abbreviation applies to 3+5OS and 4+4OS. Cells were stained with alizarin red solution for calcium phosphate deposition.
Figure 5:
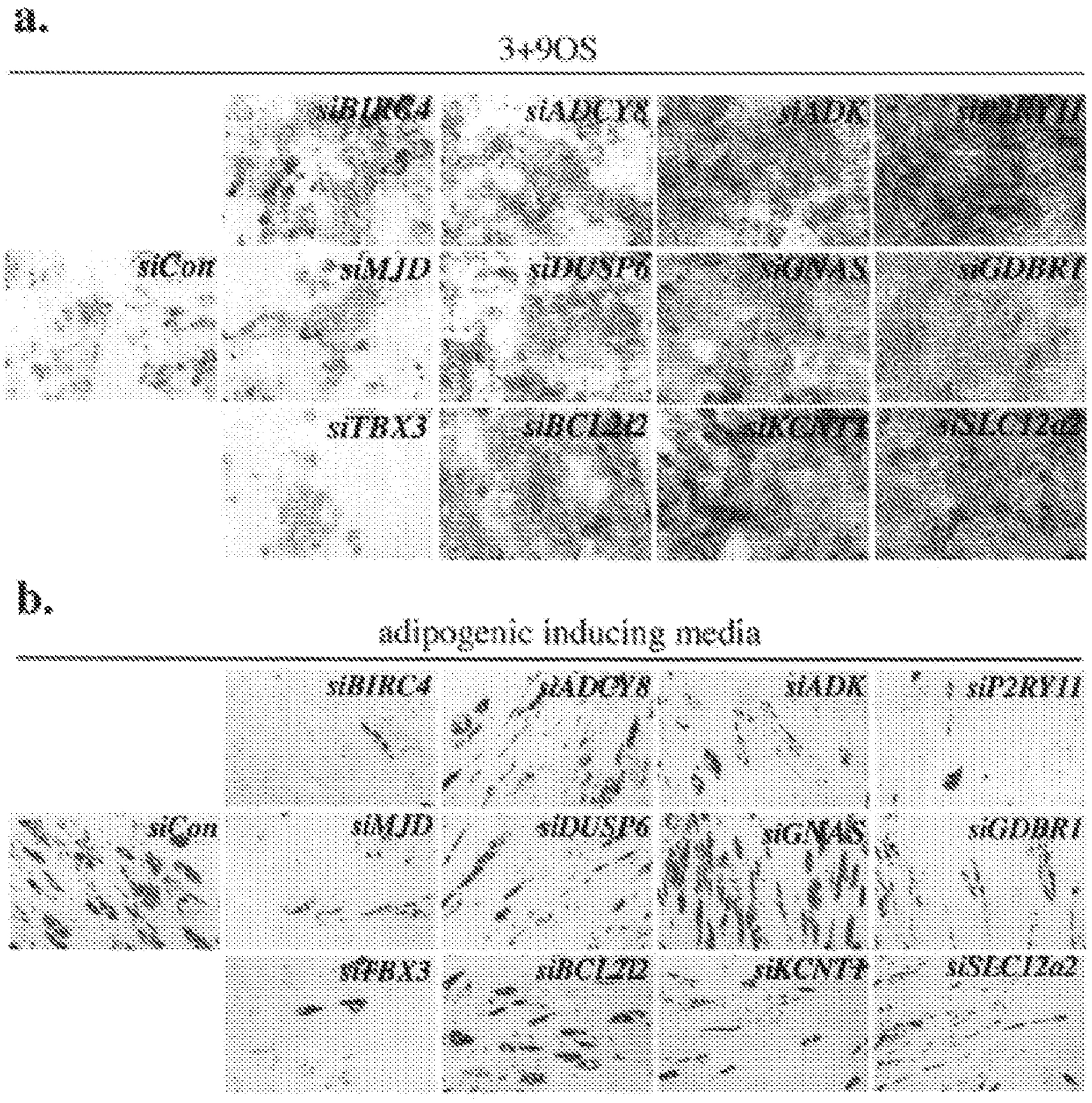
FIG. 5 illustrates that the majority of the osteogenic hit siRNAs enhanced bone cell maturation, but inhibited the adipogenic differentiation of hMSCs. a. All 12 selected hit siRNAs, except for siMJD and siTBX3, enhanced bone cell maturation when combined with the OS treatment, as demonstrated by alizarin red staining. b. All 12 selected hit siRNAs, except for siGNAS, inhibited adipogenic differentiation of hMSCs treated with the adipogenic inducing media on the second day after siRNA transfection, based on Oil Red O staining. siCon, control siRNA; OS, osteogenic inducing media; 3+9OS, OS treatment was started 3 days after siRNA transfection and continued for 9 days.
Figure 6:
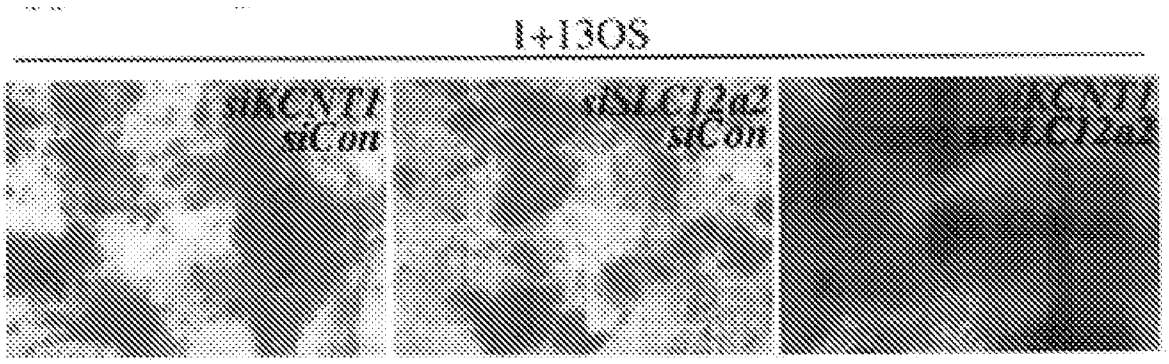
FIG. 6 illustrates that combined siKCNT1 and siSLC12a2 transfection has synergistic effect on enhancing the bone cell maturation process induced by the OS (alizarin red staining). 1+13OS, cells were treated with OS one day after siRNA transfection and treatment was continued for 13 days. OS, osteogenic inducing media.

Bone cell maturation is accompanied by extracellular matrix (ECM) mineralization (John Bilezikian et al., *Principles of bone biology*, Vol 1, 2nd edn: Academic Press) (2002)). To examine whether the osteogenic differentiation of hMSCs induced by the hit siRNAs can further proceed to the maturation stage, hit siRNA treated cells were cultured for 20 days. No ECM mineralization was detected based on alizarin red staining that detects calcium phosphate deposits, a major component of mineralized ECM, indicating that the expression knockdown by the hit siRNAs primarily functions to induce early osteogenic specification of hMSCs and the late stage osteoblast maturation may require additional factors. Since OS treated hMSCs undergo osteoblast maturation within two weeks, we tested whether sequential treatments by the hit siRNAs (initial 2-4 days) followed by the OS (additional 5-9 days) could facilitate this process. As demonstrated in FIG. 4, such sequential treatments of hMSCs with siADK and OS media clearly enhanced the intensity of alizarin red staining as compared to the control treatment. When the OS treatment was started three days after siRNA transfection and continued for 9 days, among the 12 hits tested, six (siADK, siGNAS, siP2RY11, siGBDR1, siSLC12a2 and siKCNT1) dramatically enhanced the intensity of alizarin red staining, two (siDUSP6 and siBCL212) provided modest enhancement, two (siBIRC4 and siADCY8) provided weak enhancement, and two (siTBX3 and siMJD) had no significant effect (FIG. 5*a*). These observations are consistent with the conclusion that the targeted genes of the ten effective hit siRNAs not only play inhibitory roles in osteogenic specification of hMSCs, but also in bone cell maturation. Combinatorial treatment of two siRNA hits, such as siSLC12A2 with siKCNT1, further enhances the osteogenic differentiation process (FIG. 6). It has been suggested that the osteogenic differentiation and adipogenic differentiation of hMSCs are two inverse processes, with one process inhibiting the other (Beresford, J. N. et al., *J Cell Sci* 102 (Pt 2):341-351 (1992)). Furthermore, in osteoporotic patients, the number of adipocytes was increased in the marrow, implying a change of cell fate disposition from osteoblast lineage to adipocyte lineage (Justesen, J. et al., *Biogerontology* 2:165-171 (2001); Meunier, P. et al., *Clin Orthop Relat Res* 80:147-154 (1971)). We therefore examined the effect of our hit siRNAs on adipogenic differentiation of hMSCs by combined treatment with an adipogenic inducing cocktail (100 μg/ml IBMX, 1 μM DEX and 10 μg/ml insulin). Consistent with previous studies, our hit siRNAs inhibited adipogenic differentiation of hMSCs at various degrees, except for siGNAS (FIG. 5*b*).

GNAS was identified in our screen as an osteogenic cell fate suppressor in hMSCs. The major GNAS gene product, G protein α-subunit (Gsα), couples transmembrane receptors to adenylyl cyclase and is required for the receptor-stimulated intracellular cAMP production. Inactivating mutations in this gene have been found in two types of disorders (Progressive osseous hetroplasia and Albright's hereditary osteodystrophy) that are characterized with heterotopic ossification (Chan, I. et al., *Clin Exp Dermatol* 29:77-80 (2004); Eddy, M. C. et al., *J Bone Miner Res* 15:2074-2083 (2000); Shore, E. M. et al., *N Engl J Med* 346:99-106 (2002)), whereas activating mutations in this gene were found in patients with McCune-Albright syndrome that is characterized with fibrous dysplasia of bone (Weinstein, L. S. et al., *N Engl J Med* 325:1688-1695 (1991)), suggesting that Gsα is a critical negative regulator of osteogenic commitment. This is consistent with our observation as well as others' that reduced GNAS expression switches on osteogenic cell fate in hMSCs (Lietman, S. A. et al., *Clin Orthop Relat Res,* 231-238 (2005)). Coincidentally, our screen identified not only Gsα but also several proteins that are closely involved in cAMP production, which include ADCY8 (adenylate cyclase 8), ADK (adenosine kinase) and P2RY11 (purinergic receptor P2Y, G-protein coupled, 11), suggesting a close linkage between intracellular cAMP signaling and osteogenic differentiation in hMSCs.

Figure 7:
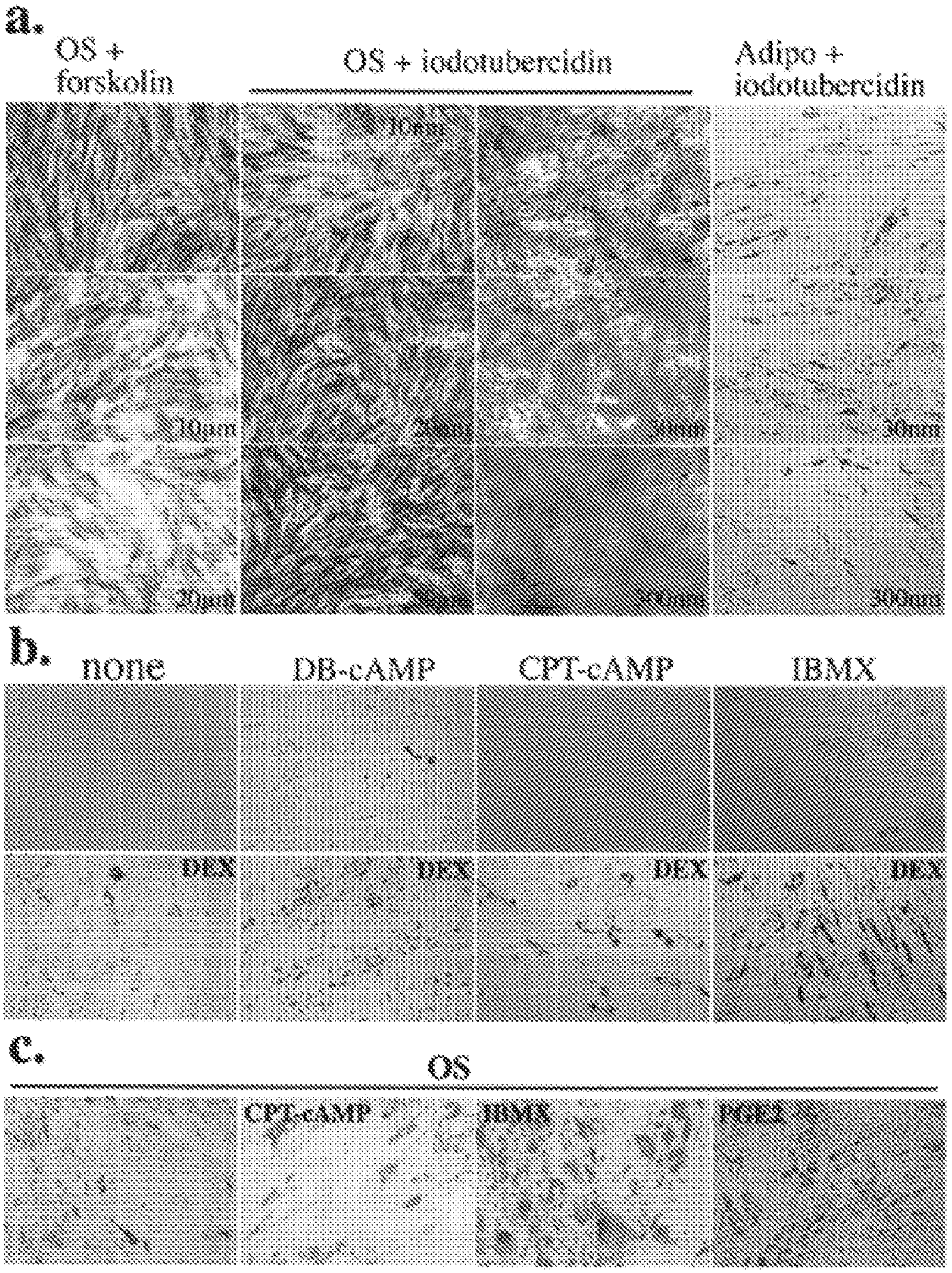
FIG. 7 illustrates that intracellular cAMP signaling plays opposing roles in osteogenic vs. adipogenic differentiation in hMSCs. a. Adenylyl cyclase agonist forskolin inhibited the osteogenic effect of the OS media on hMSCs in a dose dependent manner (a-c), while adenosine kinase inhibitor 5-iodotubercidin enhanced the osteogenic effect of the OS media (d-f, g-i) and inhibited the adipogenic differentiation of hMSCs in a dose dependent manner (j-l). a-f, ALP staining; g-i, alizarin red staining; j-l, oil red o staining. b. Treatment with cAMP analogs (DB-cAMP & CPT-cAMP) or IBMX promoted hMSCs to undergo adipogenic differentiation, especially in the presence of dexamethasone (DEX). c. Enhanced cAMP level by CPT-cAMP, IBMX or PGE2 application could switch cell fate determination from osteogenic to adipogenic differentiation in hMSCs treated with the OS. Adipo, adipogenic inducing media; OS, osteogenic inducing media.

Since the targeted genes are all positively involved in intracellular cAMP signaling, we tested the effect of two compounds of opposing function on cAMP production on osteogenic differentiation of hMSCs, ADK inhibitor 5-iodotubercidin and ADCY activator forskolin (Cottam, H. B. et al., *J Med Chem* 36:3424-3430 (1993); de Souza, N. J. et al., *Med Res Rev* 3:201-219 (1983)). Treatment with 5-iodotubercidin mimicked the effect of the hit siADK and significantly enhanced the osteogenic differentiation of hMSCs when combined with the OS treatment, while treatment with forskolin inhibited this process (FIG. 7*a*). Furthermore, combined treatment of cell permeable cAMP analog such as 8-CPT-cAMP or N6,2'-dibutyryl-cAMP (DB-cAMP) with dexamethasone was sufficient to differentiate hMSCs into mature adipocytes. Moreover, 8-CPT-cAMP could switch cell fate commitment from osteogenic to adipogenic when combined with the OS media (FIGS. 7*b* & 7*c*), consistent with the previous observations that osteogenesis and adipogenesis are mutually exclusive of each other. ATP has been shown as a ligand for P2RY11 receptor (Communi et al., 1997). Treatment of ATP inhibited the OS-induced osteogenesis of hMSCs and slightly increases the number of cells undergoing adipogenic differentiation in a dosage dependent manner, consistent with the notion that P2RY11 acts as an osteogenic suppressor in hMSCs. The present observations are consistent with the conclusion that reducing intracellular cAMP level promotes osteogenic specification but inhibits adipogenic cell fate in hMSCs, and vice versa.

Figure 8:
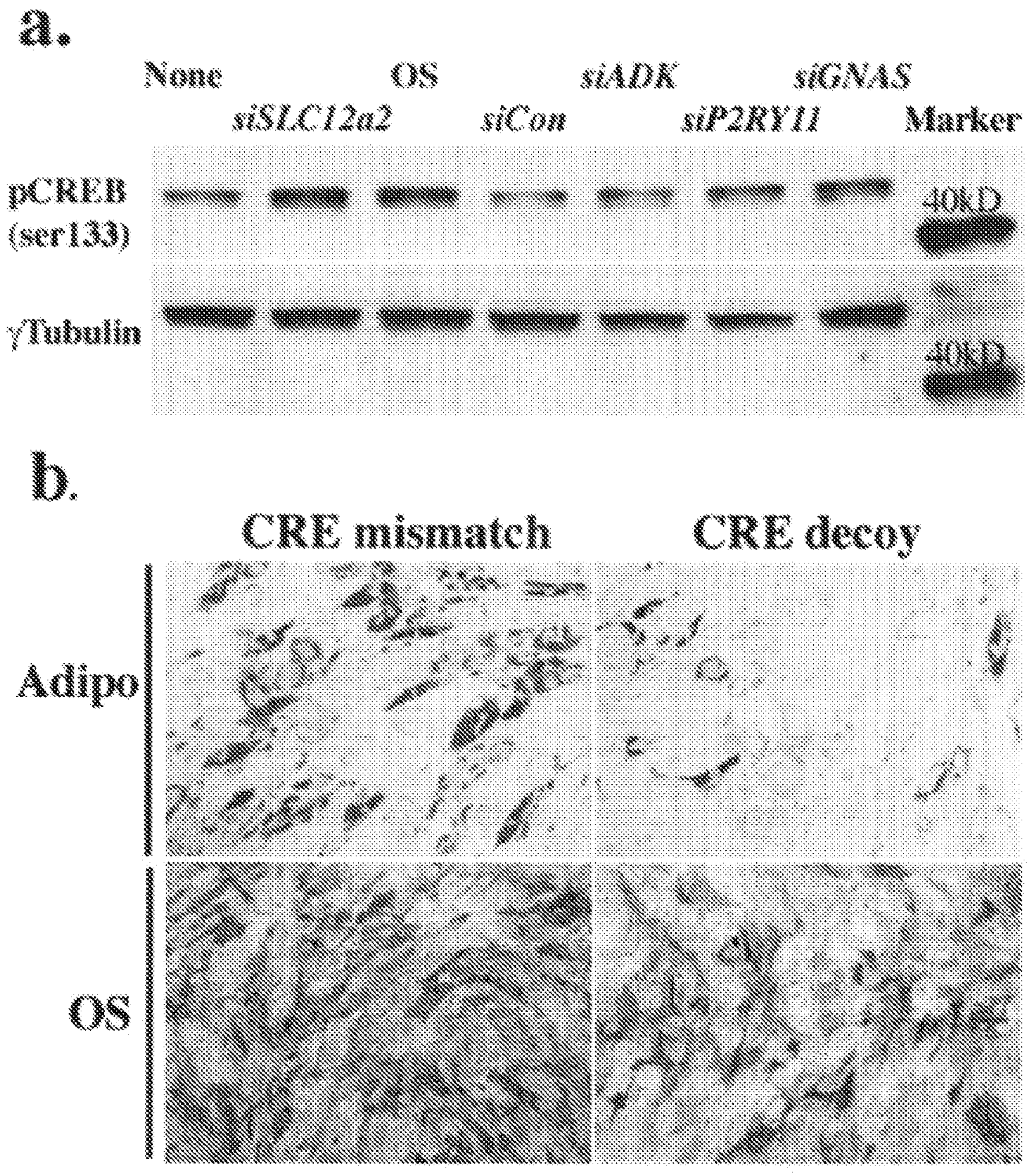
FIG. 8 illustrates that CREB activity is required for both osteogenic and adipogenic differentiation of hMSCs. a. Examination of CREB protein activity by Western blot demonstrated increased pCREB level in cells transfected with hit siRNAs compared to cells transfected with siCon or un-treated cells. b. Cells transfected with CRE (CREB responding element) decoy, which competes with endogenous CRE in target genes, are less responsive to the stimulation of adipogenic inducing media (Adipo) or osteogenic inducing media (OS).

To find out whether CREB (cAMP Responding Element Binding protein), a common downstream effector of cAMP signaling pathway, is involved in mediating cAMP signaling controlled differentiation of hMSCs, we checked the expression level of the active form of CREB proteins in cells 3 days after siP2RY11, siADK, siGNAS, siSLC12a2 or siCon transfection. In these hit siRNAs or OS treated samples, the level of pCREB protein was increased compared to the siCon treated or untreated samples (FIG. 8*a*), suggesting that CREB activity is required for osteogenic differentiation in hMSCs. To further examine the role of CREB in osteogenesis and adipogenesis, a synthetic 24-mer CRE decoy oligonucleotide that can compete with endogenous CRE enhancers for binding proteins was transfected into hMSCs (Park, Y. G. et al., *J Biol Chem* 274:1573-1580 (1999)), which were then subjected to the treatment of osteogenic or adipogenic induction media. Compared to the 24-mer CRE mismatch control oligonucleotide, CRE decoy not only inhibited cells from undergoing adipogenic differentiation, but also osteogenic differentiation (FIG. 8*b*), suggesting that CREB activity is required for both osteogenesis and adipogenesis and the inhibitory effect of cAMP signaling on osteogenic differentiation can be mediated by effectors other than CREB in hMSCs.

While the screen revealed multiple players involved in cAMP signaling pathway that controls osteogenic differentiation of hMSCs, combinatorial siRNA treatment study also suggested that different targeted genes employed different mechanisms to control the same osteogenic process, one of which is to turn on positive regulators of osteogenesis. Several proteins, including BMP-2, PLZF, and TAZ, have been shown to promote osteogenic differentiation in multipotent mesenchymal precursor cells (Hong, J. H. et al., *Science* 309:1074-1078 (2005); Ikeda, R. et al., *J Biol Chem* 280: 8523-8530 (2005); Katagiri, T. et al., *J Cell Biol* 127:1755-1766 (1994)). To test their roles in our siRNA induced osteogenic differentiation, RT-PCR was performed on these genes. While the level of BMP-2 and TAZ expression was not significantly altered among the different samples, expression of PLZF was detected in the siMJD or OS treated samples, but not in the rest hit siRNA treated samples (FIG. 9*a*), suggesting that MJD normally suppresses the expression of PLZF in hMSCs. In addition, MAPK signaling pathways have been shown activated in the OS treated hMSCs, and inhibition of these pathways suppresses OS induced osteogenesis (FIG. 9*b*) (Jaiswal, R. K. et al., *J Biol Chem* 275:9645-9652 (2000)). DUSP6 is a dual specificity phosphotase that has been shown to directly dephosphorylate ERK1/2 or p38 kinase (Muda, M. et al., *J Biol Chem* 273:9323-9329 (1998)).

Figure 9:
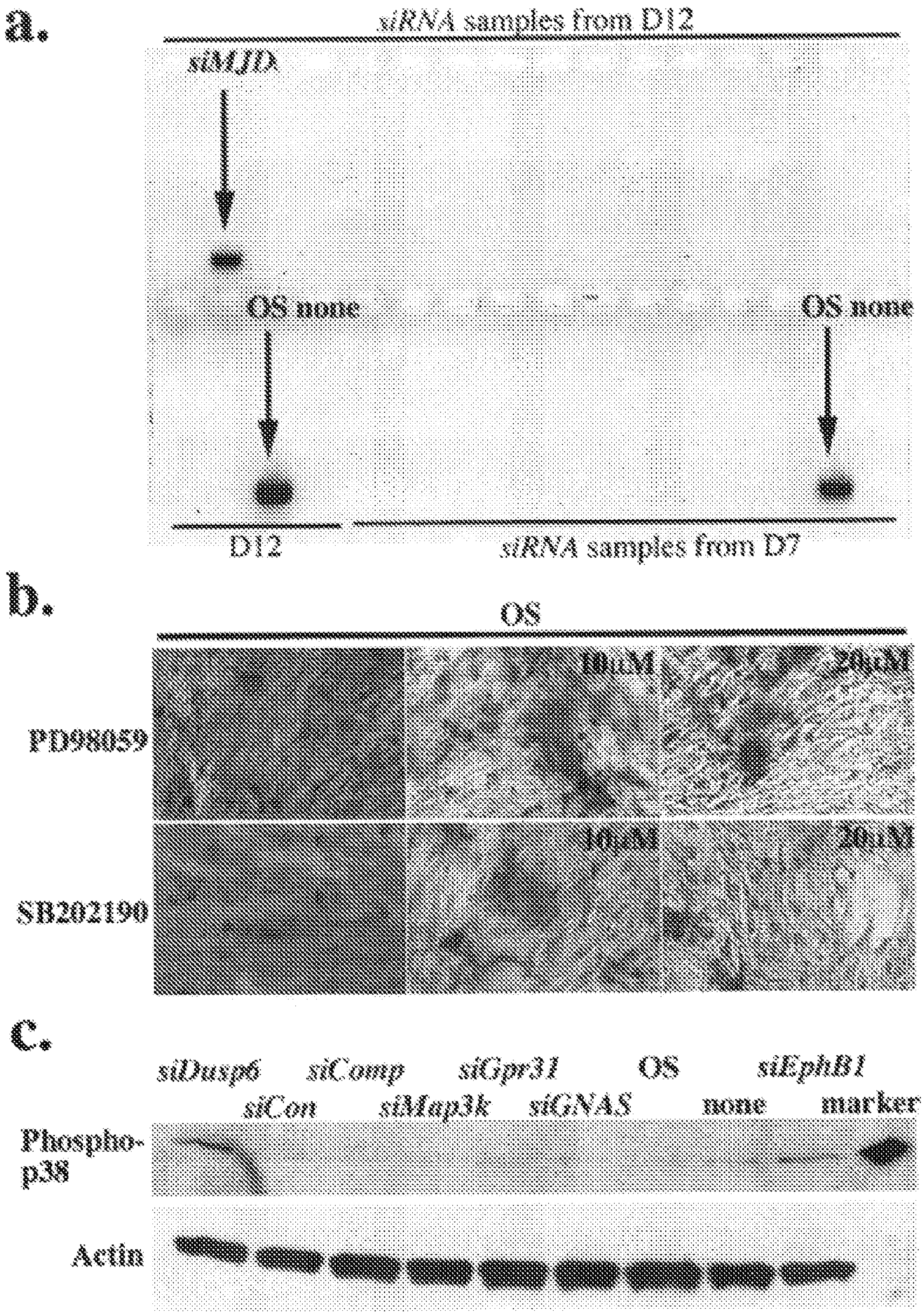
FIG. 9 illustrates additional signaling pathways involved in osteogenic differentiation of hMSCs. a. PLZF1 expression was only induced in siMJD and OS treated but not other hit siRNA treated samples collected on day 7 or day 12 after siRNA transfection. b. Inhibition of ERK1/2 or p38 signaling pathway by PD98059 or SB202190, respectively, inhibited the osteogenic inducing effect of OS on hMSCs. c. Phosphorylated form of p38 was up regulated in cells transfected with siDUSP6. OS, osteogenic inducing media.
Figure 10:
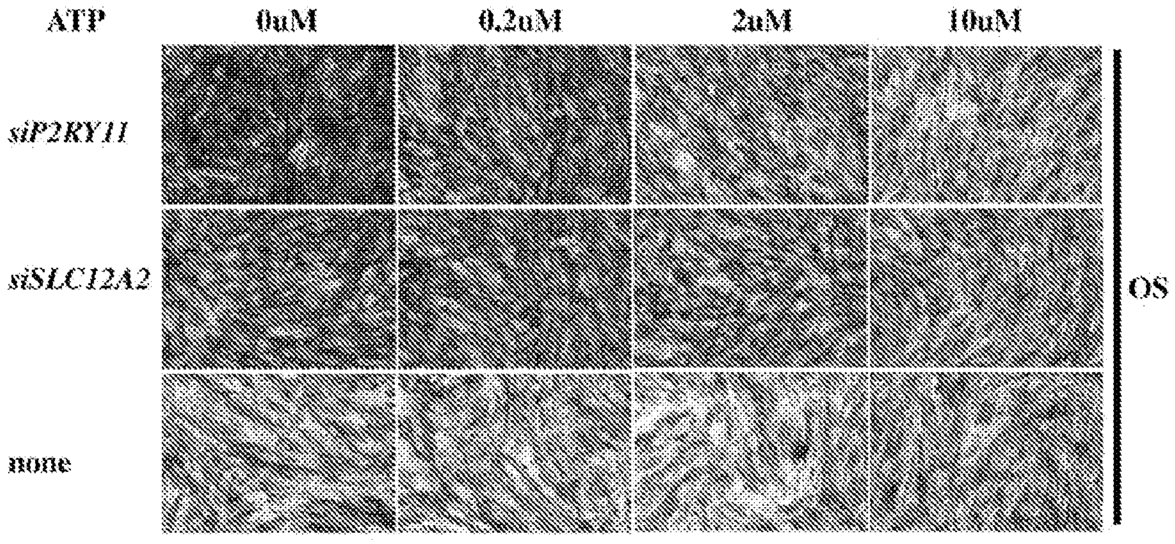
FIG. 10 illustrates that ATP has a dosage-dependent inhibitory effect on OS-induced osteogenesis of hMSCs, as well as on siP2RY11 and siSLC12a2 induced osteogenesis of hMSCs in combination with the OS treatment. OS and ATP were added on the third day after siRNA transfection and continued for a week. Cells were stained for alkaline phosphatase activity. OS, osteogenic inducing media.
Figure 11:
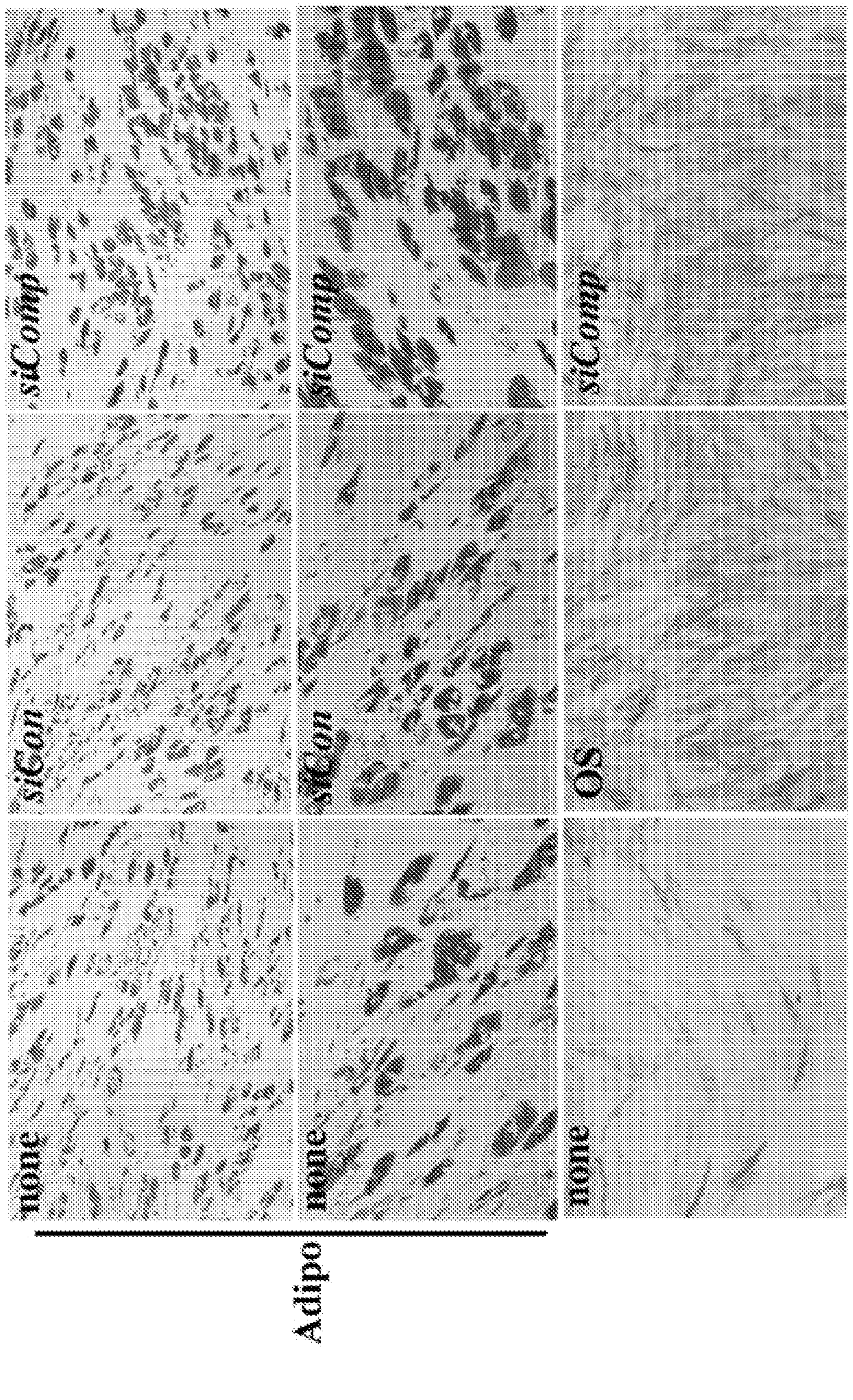
FIG. 11 illustrates that siCOMP promotes both adipogenic and osteogenic differentiation of hMSCs. The top two rows (second row panel are enlarged views of the corresponding upper panels) show that siCOMP treatment enhances adipogenesis of hMSCs induced by the adipogenic inducing media (Adipo). Cells were treated with Adipo on the third day after siRNA transfection and treatment was continued for 12 days before cells were stained with Oil Red O. The bottom row shows siCOMP induces osteogenic differentiation of hMSCs. Cells were assayed for alkaline phosphatase activity 9 days after siRNA transfection. OS, osteogenic inducing media.

We therefore examined the activation status of ERK1/2 and p38 in the siDUSP6 treated hMSCs along with other siRNA treated samples by western blot using antibodies against the phosphorylated form of the protein at 72 hours after transfection (FIG. 9*c*). The increased level of active p38 but not pERK1/2 in the siDUSP6 treated sample suggests that DUSP6 normally inhibits osteogenic differentiation of hMSCs at least partly by inhibiting the activation of p38 signaling pathway.

Our probing of the molecular mechanisms underlying the osteogenic induction effect of identified suppressors is consistent with the conclusion that different suppressors function through discrete pathways to suppress osteogenic differentiation in normal hMSCs.

While the foregoing invention has been described in some detail for purposes of clarity and understanding, it will be clear to one skilled in the art from a reading of this disclosure that various changes in form and detail can be made without departing from the true scope of the invention. For example, all the techniques, methods, compositions, apparatus and systems described above can be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

---

What is claimed is:

1. A method for identifying agents that promote osteogenesis, the methods comprising, (a) contacting a plurality of agents to a potassium channel, subfamily T, member 1 ("KCNT1") polypeptide comprising SEQ ID NO:178;

(b) measuring the activity of the polypeptide;

(c) selecting at least one of the plurality of agents, wherein the selected agent(s) inhibit the activity of the polypeptide; and (d) measuring the ability of the selected agent(s) to promote osteogenesis, thereby identifying agents that promote osteogenesis.

2. The method of claim 1, wherein the polypeptide is expressed in a host cell.

3. The method of claim 2, wherein the measuring step (b) comprises measuring the expression of the polypeptide.

4. The method of claim 3, wherein measuring the expression comprises measuring the level of transcription.

5. The method of claim 2, wherein the cells are mammalian cells.

6. The method of claim 1, wherein the measuring step (d) is carried out in vitro.

7. The method of claim 1, wherein the measuring step (d) is carried out in vivo.

8. The method of claim 1, further comprising contacting the plurality of agents to a solute carrier family 12 (sodium/potassium/chloride transporters), member 2 (SLC12A2) polypeptide comprising SEQ ID NO:180.

9. The method of claim 1, further comprising contacting the plurality of agents to a polypeptide selected from the group consisting of: SEQ ID NO:152 (GNAS complex locus (GNAS)), SEQ ID NO:156 (adenosine kinase (ADK)), SEQ ID NO:158 (purinergic receptor P2Y, G-protein coupled, 11

(P2RY11)), SEQ ID NO:180 (solute carrier family 12 (sodium/potassium/chloride transporters), member 2 (SLC12A2)) and SEQ ID NO:238 (putative glialbiastoma cell differentiation-related (GBDR1)).

10. The method of claim 1, further comprising contacting the plurality of agents to a polypeptide selected from the group consisting of: SEQ ID NO:180 (solute carrier family 12 (sodium/potassium/chloride transporters), member 2 (SLC12A2)), SEQ ID NO:152 (GNAS complex locus (GNAS)), SEQ ID NO:154 (adenylate cyclase 8 (ADCY8)), SEQ ID NO:156 (adenosine kinase (ADK)), SEQ ID NO:158 (purinergic receptor P2Y, G-protein coupled, 11 (P2RY11)), SEQ ID NO:160 (olfactory receptor, family 12, subfamily D, member 3 (OR12D3)), SEQ ID NO:162 (olfactory receptor OR52I2, SEQ ID NO:164 (olfactory receptor OR51G2), SEQ ID NO:166 (olfactory receptor OR2M4), SEQ ID NO:168 (olfactory receptor OR4F29, SEQ ID NO:170 (integrin, alpha L (ITGAL)), SEQ ID NO:172 (integrin, alpha 2 (CD49B, alpha 2 subunit of VLA-2 receptor) (ITGA2)), SEQ ID NO:174 (angiopoietin-like factor (CDT6)), SEQ ID NO:176 (angiopoietin-like 2 (ANGPTL2)), SEQ ID NO:182 (mitochondrial carrier family protein (MCFP)), SEQ ID NO:184 (B-cell CLL/lymphoma 2 (BCL2)), SEQ ID NO:186 (BCL2-like 2 (BCL2L2)), SEQ ID NO:188 (nuclear receptor subfamily 2, group E, member 3 (NR2E3)), SEQ ID NO:190 (putative leukocyte platelet-activating factor receptor (HUMNPIIY20)), SEQ ID NO:192 (chemokine (C- C motif) ligand 5 (CCL5)), SEQ ID NO:194 (dual specificity phosphatase 6 (DUSP6)1, SEQ ID NO:196 (serine/threonine kinase 10 (STK10)), SEQ ID NO:198 (putative dipeptidase (LOC64174)), SEQ ID NO:200 (phospholipase A2, group IID (PLA2G2D)), SEQ ID NO:202 (Cytochrome P450

(CYP4Z1)), SEQ ID NO:204 (aldo-keto reductase family 1, member C2 (AKR1C2)), SEQ ID NO:206 (methylmalonyl Coenzyme A mutase (MUT)), SEQ ID NO:208 (dopamine beta-hydroxylase (dopamine beta-monooxygenase) (DBH)), SEQ ID NO:210 (transketolase-like 1 (TKTL1)), SEQ ID NO:212 (fumarylacetoacetate hydrolase (furmarylacetoacetase) (FAH)), SEQ ID NO:214 (polymerase (DNA directed), eta (POLH)), SEQ ID NO:216 (cyclin-dependent kinase inhibitor 2B (CDKN2B)), SEQ ID NO:218 (CDC14 cell division cycle 14 homolog B (CDC14B)), SEQ ID NO:220 (Machado-Joseph disease (ataxin 3) (MJD)), SEQ ID NO:222 (baculoviral IAP repeat-containing 4 (BIRC4)), SEQ ID NO:224 (deafness, autosomal dominant 5 (DFNA5)), SEQ ID NO:226 (PHD finger protein 1 (PHF1)), SEQ ID NO:228 (T-box 3 (ulnar mammary syndrome) (TBX3)), SEQ ID NO:230 (praja 2, RING-H2 motif containing (PJA2), SEQ ID NO:232 (down regulated in lung cancer (HLCDGP1)), SEQ ID NO:238 (putative glialblastoma cell differentiation-related (GBDR1)), SEQ ID NO:240 (similar to semaphorin cytoplasmic domain-associated protein 3B (LOC341549)), SEQ ID NO:242 (ankyrin repeat and SOCS box-containing 11 (ASB11)), SEQ ID NO:244 (similar to Interferon-induced protein with tetratricopeptide repeats 1 (IFIT-1)), SEQ ID NO:246 (cartilage oligomeric matrix protein (pseudoachondroplasia) (COMP)), SEQ ID NO:248 (hypothetical protein BC009732 (LOC133308)), SEQ ID NO:250 (hypothetical protein MGC42105, SEQ ID NO:252 (hypothetical protein MGC15875, SEQ ID NO:254 (hypothetical protein FLJ386281), SEQ ID NO:259 (hypothetical protein LOC 114971), and SEQ ID NO:261 (DKFZP727G051 protein).

* * * * *

SEQUENCE LISTING

```
<160> NUMBER OF SEQ ID NOS: 150

<210> SEQ ID NO 1
<211> LENGTH: 21
<212> TYPE: DNA
<213> ORGANISM: Artificial Sequence
<220> FEATURE:
<223> OTHER INFORMATION: Description of Combined DNA/RNA Molecule:
      siCBFA1
      antisense
<220> FEATURE:
<223> OTHER INFORMATION: Description of Artificial Sequence:siCBFA1
      antisense
<220> FEATURE:
<223> OTHER INFORMATION: human CBFA1/OSF2 (core-binding factor alpha1
      subunit
      (CBFA1)/osteoblast-specific factor 2 (OSF2)) bone-specific
      transcription factor, early osteogenic marker double-stranded
      small interfering RNA
<220> FEATURE:
```

-continued

<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1
uaguagagau auggagugct g 21

<210> SEQ ID NO 2
<211> LENGTH: 21
<212> TYPE: DNA
<213> ORGANISM: Artificial Sequence
<220> FEATURE:
<223> OTHER INFORMATION: Description of Combined DNA/RNA Molecule:
siCBFA1
sense
<220> FEATURE:
<223> OTHER INFORMATION: Description of Artificial Sequence:siCBFA1
sense
<220> FEATURE:
<223> OTHER INFORMATION: human CBFA1/OSF2 (core-binding factor alpha1
subunit
(CBFA1)/osteoblast-specific factor 2 (OSF2)) bone-specific
transcription factor, early osteogenic marker double-stranded
small interfering RNA
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 2
gcacuccaua ucucuacuat t 21

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:CRE (CREB
(cAMP
responding element binding protein) responding
element) decoy 24-mer palindrome

<400> SEQUENCE: 3
tgacgtcatg acgtcatgac gtca 24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:CRE (CREB
(cAMP
responding element binding protein) responding
element) mismatch control

<400> SEQUENCE: 4
tgtggtcatg tggtcatgtg gtca 24

<210> SEQ ID NO 5
<211> LENGTH: 19
<212> TYPE: DNA
<213> ORGANISM: Artificial Sequence
<220> FEATURE:

-continued

<223> OTHER INFORMATION: Description of Artificial Sequence:
      glyceraldehyde-3-phosphate
      dehydrogenase (GAPDH) RT-PCR forward primer

<400> SEQUENCE: 5
gaaggtgaag gtcggagtc 19

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:
      glyceraldehyde-3-phosphate
      dehydrogenase (GAPDH) RT-PCR reverse primer

<400> SEQUENCE: 6
gaagatggtg atgggatttc 20

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:alkaline-
      phosphatase,
      liver/bone/kidney (ALPL) RT-PCR forward primer

<400> SEQUENCE: 7
tggagcttca gaagctcaac acca 24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence:alkaline-
      phosphatase,
      liver/bone/kidney (ALPL) RT-PCR reverse primer

<400> SEQUENCE: 8
atctcgttgt ctgagtacca gtcc 24

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence:runt-related
      transcription
      factor 2 (RUNX2), core-binding factor, runt domain, alpha1
      subunit (CBFA1), osteoblast-specific factor 2 (OSF2) RT-PCR
      forward primer

<400> SEQUENCE: 9
tcttcacaaa tcctcccc 18

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:runt-related
      transcription
      factor 2 (RUNX2), core-binding factor, runt domain, alpha1
      subunit (CBFA1), osteoblast-specific factor 2 (OSF2) RT-PCR
      reverse primer

<400> SEQUENCE: 10

-continued

```
tggattaaaa ggacttggtg                                                20


<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence:osterix
      (OSX),
      Sp7 transcription factor, C2H2 zinc finger
      transcription factor RT-PCR forward primer

<400> SEQUENCE: 11

cctatgtacc aggagtaatg aatag                                          25


<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:osterix
      (OSX), Sp7 transcription factor, C2H2 zinc finger
      transcription factor RT-PCR reverse primer

<400> SEQUENCE: 12

ctcctagctc tttaagttct ttctc                                          25


<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence:distal-less
      homeobox 5 (DLX5) RT-PCR forward primer

<400> SEQUENCE: 13

gagaaggttt cagaagactc agta                                           24


<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:distal-less
      homeobox 5 (DLX5) RT-PCR reverse primer

<400> SEQUENCE: 14

ctagaacagc aaaacacagt agtc                                           24


<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence:bone-
      specific
      sialoprotein (BSP), bone sialoprotein II (BNSP,
      BSP-II, SP-II), integrin-binding sialoprotein
      (IBSP) RT-PCR forward primer

<400> SEQUENCE: 15

gagaatacca cactttctgc tac                                            23


<210> SEQ ID NO 16
<211> LENGTH: 25
<212> TYPE: DNA
<213> ORGANISM: Artificial Sequence
```

-continued

```
<220> FEATURE:
<223> OTHER INFORMATION: Description of Artificial Sequence:bone-
      specific
      sialoprotein (BSP), bone sialoprotein II (BNSP,
      BSP-II, SP-II), integrin-binding sialoprotein
      (IBSP) RT-PCR reverse primer

<400> SEQUENCE: 16

aagtagctgt actcatcttc atagg                                           25


<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence:Machado-
      Joseph disease
      (MJD, MJD1, josephin), spinocerebellar ataxia 3 (SCA3),
      olivocerebellar ataxia 3, autosomal dominant, ataxin 3
      (ATXN3, AT3, ATX3) RT-PCR forward primer

<400> SEQUENCE: 17

agcacaacta aaagagcaaa gagtc                                           25


<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence:Machado-
      Joseph disease
      (MJD, MJD1, josephin), spinocerebellar ataxia 3 (SCA3),
      olivocerebellar ataxia 3, autosomal dominant, ataxin 3
      (ATXN3, AT3, ATX3) RT-PCR reverse primer

<400> SEQUENCE: 18

ctcatagcat cacctagatc actcc                                           25


<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:baculoviral
      IAP
      repeat-containing 4 (BIRC4), X-linked inhibitor of
      apoptosis (XIAP, XLP2), apoptosis inhibitor 3
      (API3), ILP1, MIHA RT-PCR forward primer

<400> SEQUENCE: 19

gtttcagcat caacactggc                                                 20


<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:baculoviral
      IAP
      repeat-containing 4 (BIRC4), X-linked inhibitor of
      apoptosis (XIAP, XLP2), apoptosis inhibitor 3
      (API3), ILP1, MIHA RT-PCR reverse primer

<400> SEQUENCE: 20

tccgtgcttc ataatctgcc                                                 20


<210> SEQ ID NO 21
<211> LENGTH: 22
<212> TYPE: DNA
```

-continued

<213> ORGANISM: Artificial Sequence
<220> FEATURE:
<223> OTHER INFORMATION: Description of Artificial Sequence:purinergic
receptor P2Y, G-protein coupled, 11, P2Y
purinoceptor 11, purinergic receptor P2Y11
(P2RY11, P2Y11) RT-PCR forward primer

<400> SEQUENCE: 21
gtgtccaccc tctactctac at 22

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence:purinergic
receptor P2Y, G-protein coupled, 11, P2Y
purinoceptor 11, purinergic receptor P2Y11
(P2RY11, P2Y11) RT-PCR reverse primer

<400> SEQUENCE: 22
ctccactctc tctacttggt tct 23

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence:solute
carrier family 12
(sodium/potassium/chloride transporters), member 2 (SLC12A2,
NKCC1), bumetanide-sensitive sodium-(potassium)-chloride
cotransporter 1 (BSC) RT-PCR forward primer

<400> SEQUENCE: 23
ggtgtctatc tcttgacctt gt 22

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence:solute
carrier family 12
(sodium/potassium/chloride transporters), member 2 (SLC12A2,
NKCC1), bumetanide-sensitive sodium-(potassium)-chloride
cotransporter 1 (BSC) RT-PCR reverse primer

<400> SEQUENCE: 24
gacctggtgt ctagtgttaa gtg 23

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence:T-box
transcription
factor (ulnar mammary syndrome) (TBX3, UMS), transcript
variant 1 (TBX3-ISO), bladder cancer related protein XHL
RT-PCR forward primer

<400> SEQUENCE: 25
ataactgaga ttgctgtggg 20

<210> SEQ ID NO 26
<211> LENGTH: 20
<212> TYPE: DNA
<213> ORGANISM: Artificial Sequence -continued
<220> FEATURE:
<223> OTHER INFORMATION: Description of Artificial Sequence:T-box transcription factor (ulnar mammary syndrome) (TBX3, UMS), transcript variant 1 (TBX3-ISO), bladder cancer related protein XHL RT-PCR reverse primer

<400> SEQUENCE: 26
agagaggggg aaaaatacag 20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:B-cell leukemia/lymphoma-like 2 (BCL2-like 2, BCL2L2), apoptosis regulator BCL-W RT-PCR forward primer

<400> SEQUENCE: 27
gctgaggcag aagggttatg 20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence:B-cell leukemia/lymphoma-like 2 (BCL2-like 2, BCL2L2), apoptosis regulator BCL-W RT-PCR reverse primer

<400> SEQUENCE: 28
atagagctgt gaactccgcc 20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:potassium channel, subfamily T, member 1 (KCNT1), KCa4.1, KIAA1422 protein RT-PCR forward primer

<400> SEQUENCE: 29
ttctggaagt tagaagcagc 20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence:potassium channel, subfamily T, member 1 (KCNT1), KCa4.1, KIAA1422 protein RT-PCR reverse primer

<400> SEQUENCE: 30
accgtacaaa ccagtaagga 20

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence:adenosine kinase (ADK, AK), transcript variant ADK-short, adenosine 5'-phosphotransferase RT-PCR forward primer

<400> SEQUENCE: 31

-continued

```
ccagagtcag tattaaaggt gg                                              22


<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence:adenosine
      kinase (ADK, AK), transcript variant ADK-short,
      adenosine 5'-phosphotransferase RT-PCR reverse
      primer

<400> SEQUENCE: 32

gagaccagtt gagacagaaa acadcy                                          26


<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence:guanine
      nucleotide binding
      protein (G protein), alpha stimulating activity polypeptide 1
      (GNAS, GNAS1) complex locus, transcript variant 3, neuroendocrine
      secretory protein 55 (NESP), G-s-alpha RT-PCR forward primer

<400> SEQUENCE: 33

atctctgtga tcctgttcct c                                               21


<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence:guanine
      nucleotide binding
      protein (G protein), alpha stimulating activity polypeptide 1
      (GNAS, GNAS1) complex locus, transcript variant 3, neuroendocrine
      secretory protein 55 (NESP), G-s-alpha RT-PCR reverse primer

<400> SEQUENCE: 34

gtgaaatgag ggtagcagta gt                                              22


<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence:dual
      specificity
      phosphatase 6 (DUSP6), transcript variant 1, serine/threonine
      specific protein phosphatase, MAP kinase phosphatase 3 (MKP3)
      RT-PCR forward primer

<400> SEQUENCE: 35

tagatacagg cagtaggttt gc                                              22


<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence:dual
      specificity
      phosphatase 6 (DUSP6), transcript variant 1, serine/threonine
      specific protein phosphatase, MAP kinase phosphatase 3 (MKP3)
      RT-PCR reverse primer

<400> SEQUENCE: 36
```

-continued

```
ctctctttgg ctcctctata tg                                              22


<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence:putative
      glialblastoma
      cell differentiation-related (GBDR1), ubiquitin associated
      domain containing 1 (UBADC1), UBA domain containing 1
      (UBAC1) RT-PCR forward primer

<400> SEQUENCE: 37

gagagacttc cagacagaac tc                                              22


<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence:putative
      glialblastoma
      cell differentiation-related (GBDR1), ubiquitin associated
      domain containing 1 (UBADC1), UBA domain containing 1
      (UBAC1) RT-PCR reverse primer

<400> SEQUENCE: 38

catctatcac ctctttctcg tc                                              22


<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence:
      promyelocytic leukemia zinc
      finger protein (PLZF), zinc finger protein 145 (ZNF145), zinc
      finger and BTB domain containing 16 (ZBTB16), kruppel-like
      zinc finger protein RT-PCR forward primer

<400> SEQUENCE: 39

tctcaaacgc cacctgcgct cacat                                           25


<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence:
      promyelocytic leukemia zinc
      finger protein (PLZF), zinc finger protein 145 (ZNF145), zinc
      finger and BTB domain containing 16 (ZBTB16), kruppel-like
      zinc finger protein RT-PCR reverse primer

<400> SEQUENCE: 40

cactggcagg gcgaggcgcc gttgt                                           25


<210> SEQ ID NO 41
<211> LENGTH: 19
<212> TYPE: RNA
<213> ORGANISM: Artificial Sequence
<220> FEATURE:
<223> OTHER INFORMATION: Description of Artificial Sequence:GNAS siRNA
<220> FEATURE:
<223> OTHER INFORMATION: guanine nucleotide binding protein (G protein),
      alpha
      stimulating activity polypeptide 1 (GNAS, GNAS1) complex locus,
      transcript variant 3, neuroendocrine secretory protein 55
```

-continued (NESP), G-s-alpha double-stranded small interfering RNA (siRNA)

<400> SEQUENCE: 41
ucgaagauug aggacuacu 19

<210> SEQ ID NO 42
<211> LENGTH: 23
<212> TYPE: DNA
<213> ORGANISM: Artificial Sequence
<220> FEATURE:
<223> OTHER INFORMATION: Description of Combined DNA/RNA Molecule:GNAS siRNA
<220> FEATURE:
<223> OTHER INFORMATION: Description of Artificial Sequence:GNAS siRNA
<220> FEATURE:
<223> OTHER INFORMATION: guanine nucleotide binding protein (G protein), alpha stimulating activity polypeptide 1 (GNAS, GNAS1) complex locus, transcript variant 3, neuroendocrine secretory protein 55 (NESP), G-s-alpha double-stranded small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 42
aaucgaagau ugaggacuac utt 23

<210> SEQ ID NO 43
<211> LENGTH: 19
<212> TYPE: RNA
<213> ORGANISM: Artificial Sequence
<220> FEATURE:
<223> OTHER INFORMATION: Description of Artificial Sequence:ADCY8 siRNA
<220> FEATURE:
<223> OTHER INFORMATION: adenylate cyclase 8 (brain) (ADCY8), adenylyl cyclase-8, brain, ADCY3, HBAC1 double-stranded small interfering RNA (siRNA)

<400> SEQUENCE: 43
ggagaucaac aagcauuca 19

<210> SEQ ID NO 44
<211> LENGTH: 23
<212> TYPE: DNA
<213> ORGANISM: Artificial Sequence
<220> FEATURE:
<223> OTHER INFORMATION: Description of Combined DNA/RNA Molecule:ADCY8 siRNA
<220> FEATURE:
<223> OTHER INFORMATION: Description of Artificial Sequence:ADCY8 siRNA
<220> FEATURE:
<223> OTHER INFORMATION: adenylate cyclase 8 (brain) (ADCY8), adenylyl cyclase-8, brain, ADCY3, HBAC1 double-stranded small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature -continued

```
<222> LOCATION: (22)..(23)
<223> OTHER INFORMATION: DNA

<400> SEQUENCE: 44

caggagauca acaagcauuc att                                              23


<210> SEQ ID NO 45
<211> LENGTH: 19
<212> TYPE: RNA
<213> ORGANISM: Artificial Sequence
<220> FEATURE:
<223> OTHER INFORMATION: Description of Combined DNA/RNA Molecule:ADK
      siRNA
<220> FEATURE:
<223> OTHER INFORMATION: Description of Artificial Sequence:ADK siRNA
<220> FEATURE:
<223> OTHER INFORMATION: adenosine kinase (ADK, AK), transcript variant
      ADK-short, adenosine 5'-phosphotransferase
      double-stranded small interfering RNA (siRNA)

<400> SEQUENCE: 45

gccacacaaa gcagcaaca                                                   19


<210> SEQ ID NO 46
<211> LENGTH: 23
<212> TYPE: DNA
<213> ORGANISM: Artificial Sequence
<220> FEATURE:
<223> OTHER INFORMATION: Description of Combined DNA/RNA Molecule:ADK
      siRNA
<220> FEATURE:
<223> OTHER INFORMATION: Description of Artificial Sequence:ADK siRNA
<220> FEATURE:
<223> OTHER INFORMATION: adenosine kinase (ADK, AK), transcript variant
      ADK-short, adenosine 5'-phosphotransferase
      double-stranded small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 46

cagccacaca aagcagcaac att                                              23


<210> SEQ ID NO 47
<211> LENGTH: 19
<212> TYPE: RNA
<213> ORGANISM: Artificial Sequence
<220> FEATURE:
<223> OTHER INFORMATION: Description of Artificial Sequence:P2RY11 siRNA
<220> FEATURE:
<223> OTHER INFORMATION: purinergic receptor P2Y, G-protein coupled, 11,
      P2Y purinoceptor 11, purinergic receptor P2Y11
      (P2RY11, P2Y11) double-stranded small interfering
      RNA (siRNA)

<400> SEQUENCE: 47

ugcgggugcu caacgugga                                                   19


<210> SEQ ID NO 48
<211> LENGTH: 23
<212> TYPE: DNA
<213> ORGANISM: Artificial Sequence
```

-continued

<220> FEATURE:
<223> OTHER INFORMATION: Description of Combined DNA/RNA Molecule:P2RY11
      siRNA
<220> FEATURE:
<223> OTHER INFORMATION: Description of Artificial Sequence:P2RY11 siRNA
<220> FEATURE:
<223> OTHER INFORMATION: purinergic receptor P2Y, G-protein coupled, 11,
      P2Y purinoceptor 11, purinergic receptor P2Y11
      (P2RY11, P2Y11) double-stranded small interfering
      RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 48
caugcgggug cucaacgugg atg 23

<210> SEQ ID NO 49
<211> LENGTH: 19
<212> TYPE: RNA
<213> ORGANISM: Artificial Sequence
<220> FEATURE:
<223> OTHER INFORMATION: Description of Artificial Sequence:OR12D3 siRNA
<220> FEATURE:
<223> OTHER INFORMATION: olfactory receptor, family 12, subfamily D,
      member
      3 (OR12D3), olfactory receptor OR6-27, hs6M1-27
      double-stranded small interfering RNA (siRNA)

<400> SEQUENCE: 49
uuggccugua gugacacau 19

<210> SEQ ID NO 50
<211> LENGTH: 23
<212> TYPE: DNA
<213> ORGANISM: Artificial Sequence
<220> FEATURE:
<223> OTHER INFORMATION: Description of Combined DNA/RNA Molecule:OR12D3
      siRNA
<220> FEATURE:
<223> OTHER INFORMATION: Description of Artificial Sequence:OR12D3 siRNA
<220> FEATURE:
<223> OTHER INFORMATION: olfactory receptor, family 12, subfamily D,
      member
      3 (OR12D3), olfactory receptor OR6-27, hs6M1-27
      double-stranded small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 50
aauuggccug uagugacaca uta 23

<210> SEQ ID NO 51
<211> LENGTH: 19

-continued

<212> TYPE: RNA
<213> ORGANISM: Artificial Sequence
<220> FEATURE:
<223> OTHER INFORMATION: Description of Artificial Sequence:OR52I2 siRNA
<220> FEATURE:
<223> OTHER INFORMATION: olfactory receptor, family 52, subfamily I,
member
2 (OR52I2), olfactory receptor OR11-12
double-stranded small interfering RNA (siRNA)

<400> SEQUENCE: 51
uggcaugagg accaaacaa 19

<210> SEQ ID NO 52
<211> LENGTH: 23
<212> TYPE: DNA
<213> ORGANISM: Artificial Sequence
<220> FEATURE:
<223> OTHER INFORMATION: Description of Combined DNA/RNA Molecule:OR52I2
siRNA
<220> FEATURE:
<223> OTHER INFORMATION: Description of Artificial Sequence:OR52I2 siRNA
<220> FEATURE:
<223> OTHER INFORMATION: olfactory receptor, family 52, subfamily I,
member
2 (OR52I2), olfactory receptor OR11-12
double-stranded small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 52
tauggcauga ggaccaaaca att 23

<210> SEQ ID NO 53
<211> LENGTH: 19
<212> TYPE: RNA
<213> ORGANISM: Artificial Sequence
<220> FEATURE:
<223> OTHER INFORMATION: Description of Artificial Sequence:OR51G2 siRNA
<220> FEATURE:
<223> OTHER INFORMATION: olfactory receptor, family 51, subfamily G,
member
2 (OR51G2), olfactory receptor OR11-28
double-stranded small interfering RNA (siRNA)

<400> SEQUENCE: 53
ucccgggcaa cugcacaau 19

<210> SEQ ID NO 54
<211> LENGTH: 23
<212> TYPE: DNA
<213> ORGANISM: Artificial Sequence
<220> FEATURE:
<223> OTHER INFORMATION: Description of Combined DNA/RNA Molecule:OR51G2
siRNA
<220> FEATURE:
<223> OTHER INFORMATION: Description of Artificial Sequence:OR51G2 siRNA
<220> FEATURE:
<223> OTHER INFORMATION: olfactory receptor, family 51, subfamily G,
member
2 (OR51G2), olfactory receptor OR11-28
double-stranded small interfering RNA (siRNA)
<220> FEATURE:

```
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 54

caucccgggc aacugcacaa utc                                              23

<210> SEQ ID NO 55
<211> LENGTH: 19
<212> TYPE: RNA
<213> ORGANISM: Artificial Sequence
<220> FEATURE:
<223> OTHER INFORMATION: Description of Artificial Sequence:OR2M4 siRNA
<220> FEATURE:
<223> OTHER INFORMATION: olfactory receptor, family 2, subfamily M,
      member
      4 (OR2M4), similar to seven transmembrane helix
      receptor (rhodopsin family) double-stranded small
      interfering RNA (siRNA)

<400> SEQUENCE: 55

ugagaccagc uucuaaaca                                                   19

<210> SEQ ID NO 56
<211> LENGTH: 23
<212> TYPE: DNA
<213> ORGANISM: Artificial Sequence
<220> FEATURE:
<223> OTHER INFORMATION: Description of Combined DNA/RNA Molecule:OR2M4
      siRNA
<220> FEATURE:
<223> OTHER INFORMATION: Description of Artificial Sequence:OR2M4 siRNA
<220> FEATURE:
<223> OTHER INFORMATION: olfactory receptor, family 2, subfamily M,
      member
      4 (OR2M4), similar to seven transmembrane helix
      receptor (rhodopsin family) double-stranded small
      interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 56

caugagacca gcuucuaaac ata                                              23

<210> SEQ ID NO 57
<211> LENGTH: 19
<212> TYPE: RNA
<213> ORGANISM: Artificial Sequence
<220> FEATURE:
<223> OTHER INFORMATION: Description of Artificial Sequence:OR4F29 siRNA
<220> FEATURE:
<223> OTHER INFORMATION: olfactory receptor, family 4, subfamily F,
      member
      29 (OR4F29), olfactory receptor OR7-21, olfactory
      receptor OR1-1, seven transmembrane helix receptor
```

-continued double-stranded small interfering RNA (siRNA)

<400> SEQUENCE: 57
cuggccaguc ucuccuuca 19

<210> SEQ ID NO 58
<211> LENGTH: 23
<212> TYPE: DNA
<213> ORGANISM: Artificial Sequence
<220> FEATURE:
<223> OTHER INFORMATION: Description of Combined DNA/RNA Molecule:OR4F29 siRNA
<220> FEATURE:
<223> OTHER INFORMATION: Description of Artificial Sequence:OR4F29 siRNA
<220> FEATURE:
<223> OTHER INFORMATION: olfactory receptor, family 4, subfamily F, member 29 (OR4F29), olfactory receptor OR7-21, olfactory receptor OR1-1, seven transmembrane helix receptor double-stranded small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 58
tacuggccag ucucuccuuc att 23

<210> SEQ ID NO 59
<211> LENGTH: 19
<212> TYPE: RNA
<213> ORGANISM: Artificial Sequence
<220> FEATURE:
<223> OTHER INFORMATION: Description of Artificial Sequence:ITGAL siRNA
<220> FEATURE:
<223> OTHER INFORMATION: integrin, alpha L (antigen CD11A (p180), lymphocyte function-associated antigen 1 (LFA-1), alpha polypeptide) (ITGAL), integrin gene promoter double-stranded small interfering RNA (siRNA)

<400> SEQUENCE: 59
gaccugcagg augacacau 19

<210> SEQ ID NO 60
<211> LENGTH: 23
<212> TYPE: DNA
<213> ORGANISM: Artificial Sequence
<220> FEATURE:
<223> OTHER INFORMATION: Description of Combined DNA/RNA Molecule:ITGAL siRNA
<220> FEATURE:
<223> OTHER INFORMATION: Description of Artificial Sequence:ITGAL siRNA
<220> FEATURE:
<223> OTHER INFORMATION: integrin, alpha L (antigen CD11A (p180), lymphocyte function-associated antigen 1 (LFA-1), alpha polypeptide) (ITGAL), integrin gene promoter double-stranded small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA -continued
<220> FEATURE:
<221> NAME/KEY: misc_feature
<222> LOCATION: (22)..(23)
<223> OTHER INFORMATION: DNA

<400> SEQUENCE: 60
cagaccugca ggaugacaca utt 23

<210> SEQ ID NO 61
<211> LENGTH: 19
<212> TYPE: RNA
<213> ORGANISM: Artificial Sequence
<220> FEATURE:
<223> OTHER INFORMATION: Description of Artificial Sequence:ITGA2 siRNA
<220> FEATURE:
<223> OTHER INFORMATION: integrin, alpha 2 (CD49B, very late (activation) antigen 2 (VLA-2) receptor alpha 2 subunit (VLAA2)) (ITGA2), platelet antigen Br (BR), platelet glycoprotein GPIa double-stranded small interfering RNA

<400> SEQUENCE: 61
ugcugguguu agcgcucag 19

<210> SEQ ID NO 62
<211> LENGTH: 23
<212> TYPE: DNA
<213> ORGANISM: Artificial Sequence
<220> FEATURE:
<223> OTHER INFORMATION: Description of Combined DNA/RNA Molecule:ITGA2 siRNA
<220> FEATURE:
<223> OTHER INFORMATION: Description of Artificial Sequence:ITGA2 siRNA
<220> FEATURE:
<223> OTHER INFORMATION: integrin, alpha 2 (CD49B, very late (activation) antigen 2 (VLA-2) receptor alpha 2 subunit (VLAA2)) (ITGA2), platelet antigen Br (BR), platelet glycoprotein GPIa double-stranded small interfering RNA
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 62
gcugcuggug uuagcgcuca gtc 23

<210> SEQ ID NO 63
<211> LENGTH: 19
<212> TYPE: RNA
<213> ORGANISM: Artificial Sequence
<220> FEATURE:
<223> OTHER INFORMATION: Description of Artificial Sequence:ITGA2 siRNA
<220> FEATURE:
<223> OTHER INFORMATION: integrin, alpha 2 (CD49B, very late (activation) antigen 2 (VLA-2) receptor alpha 2 subunit (VLAA2)) (ITGA2), platelet antigen Br (BR), platelet glycoprotein GPIa double-stranded small interfering RNA

<400> SEQUENCE: 63
cugcuggugu uagcgcuca 19

-continued

<210> SEQ ID NO 64
<211> LENGTH: 23
<212> TYPE: DNA
<213> ORGANISM: Artificial Sequence
<220> FEATURE:
<223> OTHER INFORMATION: Description of Combined DNA/RNA Molecule:ITGA2
siRNA
<220> FEATURE:
<223> OTHER INFORMATION: Description of Artificial Sequence:ITGA2 siRNA
<220> FEATURE:
<223> OTHER INFORMATION: integrin, alpha 2 (CD49B, very late
(activation) antigen 2
(VLA-2) receptor alpha 2 subunit (VLAA2)) (ITGA2), platelet
antigen Br (BR), platelet glycoprotein GPIa double-stranded
small interfering RNA
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 64
tgcugcuggu guuagcgcuc agt 23

<210> SEQ ID NO 65
<211> LENGTH: 19
<212> TYPE: RNA
<213> ORGANISM: Artificial Sequence
<220> FEATURE:
<223> OTHER INFORMATION: Description of Artificial Sequence:CDT6 siRNA
<220> FEATURE:
<223> OTHER INFORMATION: angiopoietin-like factor (CDT6), angiopoietin-
like
7 (ANGPTL7), AngX double-stranded small
interfering RNA (siRNA)

<400> SEQUENCE: 65
gcaccaagga caaggacaa 19

<210> SEQ ID NO 66
<211> LENGTH: 23
<212> TYPE: DNA
<213> ORGANISM: Artificial Sequence
<220> FEATURE:
<223> OTHER INFORMATION: Description of Combined DNA/RNA Molecule:CDT6
siRNA
<220> FEATURE:
<223> OTHER INFORMATION: Description of Artificial Sequence:CDT6 siRNA
<220> FEATURE:
<223> OTHER INFORMATION: angiopoietin-like factor (CDT6), angiopoietin-
like
7 (ANGPTL7), AngX double-stranded small
interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 66

-continued

```
cagcaccaag gacaaggaca atg                                          23


<210> SEQ ID NO 67
<211> LENGTH: 19
<212> TYPE: RNA
<213> ORGANISM: Artificial Sequence
<220> FEATURE:
<223> OTHER INFORMATION: Description of Artificial Sequence:ANGPTL2
      siRNA
<220> FEATURE:
<223> OTHER INFORMATION: angiopoietin-like 2 (ANGPTL2),
      angiopoietin-related protein 2, HARP
      double-stranded small interfering RNA (siRNA)

<400> SEQUENCE: 67

ugcgggugac uccuuuaca                                               19


<210> SEQ ID NO 68
<211> LENGTH: 23
<212> TYPE: DNA
<213> ORGANISM: Artificial Sequence
<220> FEATURE:
<223> OTHER INFORMATION: Description of Combined DNA/RNA Molecule:
      ANGPTL2
      siRNA
<220> FEATURE:
<223> OTHER INFORMATION: Description of Artificial Sequence:ANGPTL2
      siRNA
<220> FEATURE:
<223> OTHER INFORMATION: angiopoietin-like 2 (ANGPTL2),
      angiopoietin-related protein 2, HARP
      double-stranded small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 68

aaugcgggug acuccuuuac atg                                          23


<210> SEQ ID NO 69
<211> LENGTH: 19
<212> TYPE: RNA
<213> ORGANISM: Artificial Sequence
<220> FEATURE:
<223> OTHER INFORMATION: Description of Artificial Sequence:KCNT1 siRNA
<220> FEATURE:
<223> OTHER INFORMATION: potassium channel, subfamily T, member 1
      (KCNT1),
      KCa4.1, KIAA1422 protein double-stranded small
      interfering RNA (siRNA)

<400> SEQUENCE: 69

ugcgagccaa gauggacaa                                               19


<210> SEQ ID NO 70
<211> LENGTH: 23
<212> TYPE: DNA
<213> ORGANISM: Artificial Sequence
<220> FEATURE:
<223> OTHER INFORMATION: Description of Combined DNA/RNA Molecule:KCNT1
      siRNA
<220> FEATURE:
<223> OTHER INFORMATION: Description of Artificial Sequence:KCNT1 siRNA
```

-continued

<220> FEATURE:
<223> OTHER INFORMATION: potassium channel, subfamily T, member 1
(KCNT1),
KCa4.1, KIAA1422 protein double-stranded small
interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 70
caugcgagcc aagauggaca atg 23

<210> SEQ ID NO 71
<211> LENGTH: 19
<212> TYPE: RNA
<213> ORGANISM: Artificial Sequence
<220> FEATURE:
<223> OTHER INFORMATION: Description of Artificial Sequence:SLC12A2
siRNA
<220> FEATURE:
<223> OTHER INFORMATION: solute carrier family 12 (sodium/potassium/
chloride
transporters), member 2 (SLC12A2, NKCC1), bumetanide-sensitive
sodium-(potassium)-chloride cotransporter 1 (BSC)
double-stranded small interfering RNA (siRNA)

<400> SEQUENCE: 71
ccucuucgug gcuacaucu 19

<210> SEQ ID NO 72
<211> LENGTH: 23
<212> TYPE: DNA
<213> ORGANISM: Artificial Sequence
<220> FEATURE:
<223> OTHER INFORMATION: Description of Combined DNA/RNA Molecule:
SLC12A2 siRNA
<220> FEATURE:
<223> OTHER INFORMATION: Description of Artificial Sequence:SLC12A2
siRNA
<220> FEATURE:
<223> OTHER INFORMATION: solute carrier family 12 (sodium/potassium/
chloride transporters), member 2 (SLC12A2, NKCC1), bumetanide-
sensitive
sodium-(potassium)-chloride cotransporter 1 (BSC)
double-stranded small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 72
aaccucuucg uggcuacauc uta 23

<210> SEQ ID NO 73
<211> LENGTH: 19
<212> TYPE: RNA

-continued

<213> ORGANISM: Artificial Sequence
<220> FEATURE:
<223> OTHER INFORMATION: Description of Artificial Sequence:MCFP siRNA
<220> FEATURE:
<223> OTHER INFORMATION: mitochondrial carrier family protein (MCFP),
      solute carrier family 25, member 40 (SLC25A40),
      LOC55972 double-stranded small interfering RNA
      (siRNA)

<400> SEQUENCE: 73
uggacucaug gaucaucua 19

<210> SEQ ID NO 74
<211> LENGTH: 23
<212> TYPE: DNA
<213> ORGANISM: Artificial Sequence
<220> FEATURE:
<223> OTHER INFORMATION: Description of Combined DNA/RNA Molecule:MCFP
      siRNA
<220> FEATURE:
<223> OTHER INFORMATION: Description of Artificial Sequence:MCFP siRNA
<220> FEATURE:
<223> OTHER INFORMATION: mitochondrial carrier family protein (MCFP),
      solute carrier family 25, member 40 (SLC25A40),
      LOC55972 double-stranded small interfering RNA
      (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 74
aauggacuca uggaucaucu atg 23

<210> SEQ ID NO 75
<211> LENGTH: 19
<212> TYPE: RNA
<213> ORGANISM: Artificial Sequence
<220> FEATURE:
<223> OTHER INFORMATION: Description of Artificial Sequence:BCL2 siRNA
<220> FEATURE:
<223> OTHER INFORMATION: B-cell CLL/lymphoma 2 (BCL2), nuclear gene
      encoding mitochondrial protein, transcript variant
      alpha, Bcl-2 double-stranded small interfering RNA
      (siRNA)

<400> SEQUENCE: 75
ugugugugga gagcgucaa 19

<210> SEQ ID NO 76
<211> LENGTH: 23
<212> TYPE: DNA
<213> ORGANISM: Artificial Sequence
<220> FEATURE:
<223> OTHER INFORMATION: Description of Combined DNA/RNA Molecule:BCL2
      siRNA
<220> FEATURE:
<223> OTHER INFORMATION: Description of Artificial Sequence:BCL2 siRNA
<220> FEATURE:
<223> OTHER INFORMATION: B-cell CLL/lymphoma 2 (BCL2), nuclear gene
      encoding mitochondrial protein, transcript variant
      alpha, Bcl-2 double-stranded small interfering RNA
      (siRNA)
<220> FEATURE:
<221> NAME/KEY: misc_feature -continued
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 76
caugugugug gagagcguca acc 23

<210> SEQ ID NO 77
<211> LENGTH: 19
<212> TYPE: RNA
<213> ORGANISM: Artificial Sequence
<220> FEATURE:
<223> OTHER INFORMATION: Description of Artificial Sequence:BCL2L2 siRNA
<220> FEATURE:
<223> OTHER INFORMATION: B-cell leukemia/lymphoma-like 2 (BCL2-like 2, BCL2L2), apoptosis regulator BCL-W double-stranded small interfering RNA (siRNA)

<400> SEQUENCE: 77
cccaggucuc cgaugaacu 19

<210> SEQ ID NO 78
<211> LENGTH: 23
<212> TYPE: DNA
<213> ORGANISM: Artificial Sequence
<220> FEATURE:
<223> OTHER INFORMATION: Description of Combined DNA/RNA Molecule:BCL2L2 siRNA
<220> FEATURE:
<223> OTHER INFORMATION: Description of Artificial Sequence:BCL2L2 siRNA
<220> FEATURE:
<223> OTHER INFORMATION: B-cell leukemia/lymphoma-like 2 (BCL2-like 2, BCL2L2), apoptosis regulator BCL-W double-stranded small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 78
cacccagguc uccgaugaac utt 23

<210> SEQ ID NO 79
<211> LENGTH: 19
<212> TYPE: RNA
<213> ORGANISM: Artificial Sequence
<220> FEATURE:
<223> OTHER INFORMATION: Description of Artificial Sequence:NR2E3 siRNA
<220> FEATURE:
<223> OTHER INFORMATION: nuclear receptor subfamily 2, group E, member 3 (NR2E3), transcript variant 1, photoreceptor-specific nuclear receptor isoform a (PNR), retina-specific nuclear receptor (RNR), ESCS, rd7 double-stranded small interfering RNA (siRNA)

<400> SEQUENCE: 79
gcagcagcgg gaagcacua 19

-continued

<210> SEQ ID NO 80
<211> LENGTH: 23
<212> TYPE: DNA
<213> ORGANISM: Artificial Sequence
<220> FEATURE:
<223> OTHER INFORMATION: Description of Combined DNA/RNA Molecule:NR2E3 siRNA
<220> FEATURE:
<223> OTHER INFORMATION: Description of Artificial Sequence:NR2E3 siRNA
<220> FEATURE:
<223> OTHER INFORMATION: nuclear receptor subfamily 2, group E, member 3 (NR2E3), transcript variant 1, photoreceptor-specific nuclear receptor isoform a (PNR), retina-specific nuclear receptor (RNR), ESCS, rd7 double-stranded small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 80
cagcagcagc gggaagcacu atg 23

<210> SEQ ID NO 81
<211> LENGTH: 19
<212> TYPE: RNA
<213> ORGANISM: Artificial Sequence
<220> FEATURE:
<223> OTHER INFORMATION: Description of Artificial Sequence:NR2E3 siRNA
<220> FEATURE:
<223> OTHER INFORMATION: nuclear receptor subfamily 2, group E, member 3 (NR2E3), transcript variant 1, photoreceptor-specific nuclear receptor isoform a (PNR), retina-specific nuclear receptor (RNR), ESCS, rd7 double-stranded small interfering RNA (siRNA)

<400> SEQUENCE: 81
gaggaugcug augagaaua 19

<210> SEQ ID NO 82
<211> LENGTH: 23
<212> TYPE: DNA
<213> ORGANISM: Artificial Sequence
<220> FEATURE:
<223> OTHER INFORMATION: Description of Combined DNA/RNA Molecule:NR2E3 siRNA
<220> FEATURE:
<223> OTHER INFORMATION: Description of Artificial Sequence:NR2E3 siRNA
<220> FEATURE:
<223> OTHER INFORMATION: nuclear receptor subfamily 2, group E, member 3 (NR2E3), transcript variant 1, photoreceptor-specific nuclear receptor isoform a (PNR), retina-specific nuclear receptor (RNR), ESCS, rd7 double-stranded small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 82

-continued

```
cagaggaugc ugaugagaau att                                          23


<210> SEQ ID NO 83
<211> LENGTH: 19
<212> TYPE: RNA
<213> ORGANISM: Artificial Sequence
<220> FEATURE:
<223> OTHER INFORMATION: Description of Artificial Sequence:HUMNPIIY20
      siRNA
<220> FEATURE:
<223> OTHER INFORMATION: putative leukocyte platelet-activating factor
      receptor (HUMNPIIY20, PAFR),  G protein-coupled
      receptor 135 (GPR135) double-stranded small
      interfering RNA (siRNA)

<400> SEQUENCE: 83

cgcucagcgu ggcgcucau                                               19


<210> SEQ ID NO 84
<211> LENGTH: 23
<212> TYPE: DNA
<213> ORGANISM: Artificial Sequence
<220> FEATURE:
<223> OTHER INFORMATION: Description of Combined DNA/RNA
      Molecule:HUMNPIIY20 siRNA
<220> FEATURE:
<223> OTHER INFORMATION: Description of Artificial Sequence:HUMNPIIY20
      siRNA
<220> FEATURE:
<223> OTHER INFORMATION: putative leukocyte platelet-activating factor
      receptor (HUMNPIIY20, PAFR),  G protein-coupled
      receptor 135 (GPR135) double-stranded small
      interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 84

cacgcucagc guggcgcuca uct                                          23


<210> SEQ ID NO 85
<211> LENGTH: 19
<212> TYPE: RNA
<213> ORGANISM: Artificial Sequence
<220> FEATURE:
<223> OTHER INFORMATION: Description of Artificial Sequence:CCL5 siRNA
<220> FEATURE:
<223> OTHER INFORMATION: chemokine (C-C motif) ligand 5 (CCL5), small
      inducible cytokine
      subfamily A (Cys-Cys), member 5 (SCYA5), regulated upon activation,
      normally T-expressed, and presumably secreted (RANTES), T-cell
      specific protein p228 double-stranded small interfering RNA (siRNA)

<400> SEQUENCE: 85

uggguucggg aguacauca                                               19


<210> SEQ ID NO 86
<211> LENGTH: 23
<212> TYPE: DNA
<213> ORGANISM: Artificial Sequence
<220> FEATURE:
<223> OTHER INFORMATION: Description of Combined DNA/RNA Molecule:CCL5
      siRNA
```

```
<220> FEATURE:
<223> OTHER INFORMATION: Description of Artificial Sequence:CCL5 siRNA
<220> FEATURE:
<223> OTHER INFORMATION: chemokine (C-C motif) ligand 5 (CCL5), small
      inducible cytokine
      subfamily A (Cys-Cys), member 5 (SCYA5), regulated upon
      activation,
      normally T-expressed, and presumably secreted (RANTES), T-cell
      specific protein p228 double-stranded small interfering RNA
      (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 86

aauggguucg ggaguacauc aac                                              23

<210> SEQ ID NO 87
<211> LENGTH: 19
<212> TYPE: RNA
<213> ORGANISM: Artificial Sequence
<220> FEATURE:
<223> OTHER INFORMATION: Description of Artificial Sequence:DUSP6 siRNA
<220> FEATURE:
<223> OTHER INFORMATION: dual specificity phosphatase 6 (DUSP6),
      transcript
      variant 1, serine/threonine specific protein
      phosphatase, MAP kinase phosphatase 3 (MKP3)
      double-stranded small interfering RNA (siRNA)

<400> SEQUENCE: 87

cugugguguc uugguacau                                                   19

<210> SEQ ID NO 88
<211> LENGTH: 23
<212> TYPE: DNA
<213> ORGANISM: Artificial Sequence
<220> FEATURE:
<223> OTHER INFORMATION: Description of Combined DNA/RNA Molecule:DUSP6
      siRNA
<220> FEATURE:
<223> OTHER INFORMATION: Description of Artificial Sequence:DUSP6 siRNA
<220> FEATURE:
<223> OTHER INFORMATION: dual specificity phosphatase 6 (DUSP6),
      transcript
      variant 1, serine/threonine specific protein
      phosphatase, MAP kinase phosphatase 3 (MKP3)
      double-stranded small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 88

aacuguggug ucuuggaca utg                                               23
```

-continued

```
<210> SEQ ID NO 89
<211> LENGTH: 19
<212> TYPE: RNA
<213> ORGANISM: Artificial Sequence
<220> FEATURE:
<223> OTHER INFORMATION: Description of Artificial Sequence:STK10 siRNA
<220> FEATURE:
<223> OTHER INFORMATION: serine/threonine kinase 10 (STK10), STE20-like
      Ser/The kinase, lymphocyte-oriented kinase (LOK),
      PRO2729 double-stranded small interfering RNA
      (siRNA)

<400> SEQUENCE: 89

gagcacgaaa cccagaaac                                                19


<210> SEQ ID NO 90
<211> LENGTH: 23
<212> TYPE: DNA
<213> ORGANISM: Artificial Sequence
<220> FEATURE:
<223> OTHER INFORMATION: Description of Combined DNA/RNA Molecule:STK10
      siRNA
<220> FEATURE:
<223> OTHER INFORMATION: Description of Artificial Sequence:STK10 siRNA
<220> FEATURE:
<223> OTHER INFORMATION: serine/threonine kinase 10 (STK10), STE20-like
      Ser/The kinase, lymphocyte-oriented kinase (LOK),
      PRO2729 double-stranded small interfering RNA
      (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 90

tagagcacga aacccagaaa ctg                                           23


<210> SEQ ID NO 91
<211> LENGTH: 19
<212> TYPE: RNA
<213> ORGANISM: Artificial Sequence
<220> FEATURE:
<223> OTHER INFORMATION: Description of Artificial Sequence:LOC64174
      siRNA
<220> FEATURE:
<223> OTHER INFORMATION: putative dipeptidase (LOC64174), dipeptidase 2
      (DPEP2), metallopeptidase of family M19, renal
      dipeptidase, MBD2 double-stranded small
      interfering RNA (siRNA)

<400> SEQUENCE: 91

ucgggauugg uggagauua                                                19


<210> SEQ ID NO 92
<211> LENGTH: 23
<212> TYPE: DNA
<213> ORGANISM: Artificial Sequence
<220> FEATURE:
<223> OTHER INFORMATION: Description of Combined DNA/RNA Molecule:
      LOC64174
      siRNA
<220> FEATURE:
<223> OTHER INFORMATION: Description of Artificial Sequence:LOC64174
      siRNA
<220> FEATURE:
```

-continued

```
<223> OTHER INFORMATION: putative dipeptidase (LOC64174), dipeptidase 2
      (DPEP2), metallopeptidase of family M19, renal
      dipeptidase, MBD2 double-stranded small
      interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 92

caucgggauu gguggagauu atg                                          23


<210> SEQ ID NO 93
<211> LENGTH: 19
<212> TYPE: RNA
<213> ORGANISM: Artificial Sequence
<220> FEATURE:
<223> OTHER INFORMATION: Description of Artificial Sequence:PLA2G2D
      siRNA
<220> FEATURE:
<223> OTHER INFORMATION: phospholipase A2, group IID (PLA2G2D),
      secretory
      phospholipase A2s (SPLASH, sPLA2S), secretory
      phospholipase A2-IID (PLA2IID) double-stranded
      small interfering RNA (siRNA)

<400> SEQUENCE: 93

ccagaagcga cugcguuuc                                               19


<210> SEQ ID NO 94
<211> LENGTH: 23
<212> TYPE: DNA
<213> ORGANISM: Artificial Sequence
<220> FEATURE:
<223> OTHER INFORMATION: Description of Combined DNA/RNA Molecule:
      PLA2G2D
      siRNA
<220> FEATURE:
<223> OTHER INFORMATION: Description of Artificial Sequence:PLA2G2D
      siRNA
<220> FEATURE:
<223> OTHER INFORMATION: phospholipase A2, group IID (PLA2G2D),
      secretory
      phospholipase A2s (SPLASH, sPLA2S), secretory
      phospholipase A2-IID (PLA2IID) double-stranded
      small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 94

taccagaagc gacugcguuu cta                                          23


<210> SEQ ID NO 95
<211> LENGTH: 19
<212> TYPE: RNA
```

-continued

```
<213> ORGANISM: Artificial Sequence
<220> FEATURE:
<223> OTHER INFORMATION: Description of Artificial Sequence:CYP4Z1 siRNA
<220> FEATURE:
<223> OTHER INFORMATION: cytochrome P450, family 4, subfamily Z,
      polypeptide 1 (CYP4Z1), cytochrome P450 4Z1,
      CYP4A20 double-stranded small interfering RNA
      (siRNA)

<400> SEQUENCE: 95

ucccuaugcc uucauacca                                                19


<210> SEQ ID NO 96
<211> LENGTH: 23
<212> TYPE: DNA
<213> ORGANISM: Artificial Sequence
<220> FEATURE:
<223> OTHER INFORMATION: Description of Combined DNA/RNA Molecule:CYP4Z1
      siRNA
<220> FEATURE:
<223> OTHER INFORMATION: Description of Artificial Sequence:CYP4Z1 siRNA
<220> FEATURE:
<223> OTHER INFORMATION: cytochrome P450, family 4, subfamily Z,
      polypeptide 1 (CYP4Z1), cytochrome P450 4Z1,
      CYP4A20 double-stranded small interfering RNA
      (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 96

caucccuaug ccuucauacc att                                           23


<210> SEQ ID NO 97
<211> LENGTH: 19
<212> TYPE: RNA
<213> ORGANISM: Artificial Sequence
<220> FEATURE:
<223> OTHER INFORMATION: Description of Artificial Sequence:AKR1C2 siRNA
<220> FEATURE:
<223> OTHER INFORMATION: aldo-keto reductase family 1, member C2
      (AKR1C2), transcript
      variant 1, dihydrodiol dehydrogenase 2 (DD2), bile acid binding
      protein (BABP), type III 3-alpha hydroxysteroid dehydrogenase
      double-stranded small interfering RNA (siRNA)

<400> SEQUENCE: 97

agccagggcu caaguacaa                                                19


<210> SEQ ID NO 98
<211> LENGTH: 23
<212> TYPE: DNA
<213> ORGANISM: Artificial Sequence
<220> FEATURE:
<223> OTHER INFORMATION: Description of Combined DNA/RNA Molecule:AKR1C2
      siRNA
<220> FEATURE:
<223> OTHER INFORMATION: Description of Artificial Sequence:AKR1C2 siRNA
<220> FEATURE:
<223> OTHER INFORMATION: aldo-keto reductase family 1, member C2
      (AKR1C2), transcript
      variant 1, dihydrodiol dehydrogenase 2 (DD2), bile acid binding
      protein (BABP), type III 3-alpha hydroxysteroid dehydrogenase
      double-stranded small interfering RNA (siRNA)
```

-continued

<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 98
caagccaggg cucaaguaca agc 23

<210> SEQ ID NO 99
<211> LENGTH: 19
<212> TYPE: RNA
<213> ORGANISM: Artificial Sequence
<220> FEATURE:
<223> OTHER INFORMATION: Description of Artificial Sequence:MUT siRNA
<220> FEATURE:
<223> OTHER INFORMATION: methylmalonyl Coenzyme A mutase (MUT, MCM), nuclear gene encoding mitochondrial protein, methylmalonyl-CoA mutase double-stranded small interfering RNA (siRNA)

<400> SEQUENCE: 99
gcugagggaa uaccuaaac 19

<210> SEQ ID NO 100
<211> LENGTH: 23
<212> TYPE: DNA
<213> ORGANISM: Artificial Sequence
<220> FEATURE:
<223> OTHER INFORMATION: Description of Combined DNA/RNA Molecule:MUT siRNA
<220> FEATURE:
<223> OTHER INFORMATION: Description of Artificial Sequence:MUT siRNA
<220> FEATURE:
<223> OTHER INFORMATION: methylmalonyl Coenzyme A mutase (MUT, MCM), nuclear gene encoding mitochondrial protein, methylmalonyl-CoA mutase double-stranded small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 100
tagcugaggg aauaccuaaa ctt 23

<210> SEQ ID NO 101
<211> LENGTH: 19
<212> TYPE: RNA
<213> ORGANISM: Artificial Sequence
<220> FEATURE:
<223> OTHER INFORMATION: Description of Artificial Sequence:DBH siRNA
<220> FEATURE:
<223> OTHER INFORMATION: dopamine beta-hydroxylase (DBH), dopamine beta-monooxygenase (DBM) double-stranded small interfering RNA (siRNA)

<400> SEQUENCE: 101

-continued ccacguacug gugcuacau 19

<210> SEQ ID NO 102
<211> LENGTH: 23
<212> TYPE: DNA
<213> ORGANISM: Artificial Sequence
<220> FEATURE:
<223> OTHER INFORMATION: Description of Combined DNA/RNA Molecule:DBH siRNA
<220> FEATURE:
<223> OTHER INFORMATION: Description of Artificial Sequence:DBH siRNA
<220> FEATURE:
<223> OTHER INFORMATION: dopamine beta-hydroxylase (DBH), dopamine beta-monooxygenase (DBM) double-stranded small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 102
gaccacguac uggugcuaca uta 23

<210> SEQ ID NO 103
<211> LENGTH: 19
<212> TYPE: RNA
<213> ORGANISM: Artificial Sequence
<220> FEATURE:
<223> OTHER INFORMATION: Description of Artificial Sequence:TKTL1 siRNA
<220> FEATURE:
<223> OTHER INFORMATION: transketolase-like 1 (TKTL1), transketolase-2 (TKT2), TKR double-stranded small interfering RNA (siRNA)

<400> SEQUENCE: 103
uccgugucau cgaccuguu 19

<210> SEQ ID NO 104
<211> LENGTH: 23
<212> TYPE: DNA
<213> ORGANISM: Artificial Sequence
<220> FEATURE:
<223> OTHER INFORMATION: Description of Combined DNA/RNA Molecule:TKTL1 siRNA
<220> FEATURE:
<223> OTHER INFORMATION: Description of Artificial Sequence:TKTL1 siRNA
<220> FEATURE:
<223> OTHER INFORMATION: transketolase-like 1 (TKTL1), transketolase-2 (TKT2), TKR double-stranded small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 104

-continued

```
tauccguguc aucgaccugu uta                                          23


<210> SEQ ID NO 105
<211> LENGTH: 19
<212> TYPE: RNA
<213> ORGANISM: Artificial Sequence
<220> FEATURE:
<223> OTHER INFORMATION: Description of Artificial Sequence:FAH siRNA
<220> FEATURE:
<223> OTHER INFORMATION: fumarylacetoacetate hydrolase (FAH),
      fumarylacetoacetase, FAA hydrolase double-stranded
      small interfering RNA (siRNA)

<400> SEQUENCE: 105

cuucggaagu gugcauuca                                               19


<210> SEQ ID NO 106
<211> LENGTH: 23
<212> TYPE: DNA
<213> ORGANISM: Artificial Sequence
<220> FEATURE:
<223> OTHER INFORMATION: Description of Combined DNA/RNA Molecule:FAH
      siRNA
<220> FEATURE:
<223> OTHER INFORMATION: Description of Artificial Sequence:FAH siRNA
<220> FEATURE:
<223> OTHER INFORMATION: fumarylacetoacetate hydrolase (FAH),
      fumarylacetoacetase, FAA hydrolase double-stranded
      small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 106

aacuucggaa gugugcauuc atc                                          23


<210> SEQ ID NO 107
<211> LENGTH: 19
<212> TYPE: RNA
<213> ORGANISM: Artificial Sequence
<220> FEATURE:
<223> OTHER INFORMATION: Description of Artificial Sequence:POLH siRNA
<220> FEATURE:
<223> OTHER INFORMATION: polymerase (DNA directed), eta (POLH),
      xeroderma
      pigmentosum variant (XPV, XP-V), RAD30A
      double-stranded small interfering RNA (siRNA)

<400> SEQUENCE: 107

ugccagaaca cauggacua                                               19


<210> SEQ ID NO 108
<211> LENGTH: 23
<212> TYPE: DNA
<213> ORGANISM: Artificial Sequence
<220> FEATURE:
<223> OTHER INFORMATION: Description of Combined DNA/RNA Molecule:POLH
      siRNA
<220> FEATURE:
<223> OTHER INFORMATION: Description of Artificial Sequence:POLH siRNA
<220> FEATURE:
<223> OTHER INFORMATION: polymerase (DNA directed), eta (POLH),
      xeroderma
```

-continued

```
      pigmentosum variant (XPV, XP-V), RAD30A
      double-stranded small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 108

taugccagaa cacauggacu atc                                              23


<210> SEQ ID NO 109
<211> LENGTH: 19
<212> TYPE: RNA
<213> ORGANISM: Artificial Sequence
<220> FEATURE:
<223> OTHER INFORMATION: Description of Artificial Sequence:CDKN2B siRNA
<220> FEATURE:
<223> OTHER INFORMATION: cyclin-dependent kinase inhibitor 2B (CDKN2B),
      transcript
      variant 2, CDK4B inhibitor, p15 CDK inhibitor, cyclin-dependent
      kinases 4 and 6 binding protein, multiple tumor suppressor 2
      (MTS2), INK4B double-stranded small interfering RNA (siRNA)

<400> SEQUENCE: 109

ggugcgacag cuccuggaa                                                   19


<210> SEQ ID NO 110
<211> LENGTH: 23
<212> TYPE: DNA
<213> ORGANISM: Artificial Sequence
<220> FEATURE:
<223> OTHER INFORMATION: Description of Combined DNA/RNA Molecule:CDKN2B
      siRNA
<220> FEATURE:
<223> OTHER INFORMATION: Description of Artificial Sequence:CDKN2B siRNA
<220> FEATURE:
<223> OTHER INFORMATION: cyclin-dependent kinase inhibitor 2B (CDKN2B),
      transcript
      variant 2, CDK4B inhibitor, p15 CDK inhibitor, cyclin-dependent
      kinases 4 and 6 binding protein, multiple tumor suppressor 2
      (MTS2), INK4B double-stranded small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 110

aaggugcgac agcuccugga agc                                              23


<210> SEQ ID NO 111
<211> LENGTH: 19
<212> TYPE: RNA
<213> ORGANISM: Artificial Sequence
<220> FEATURE:
<223> OTHER INFORMATION: Description of Artificial Sequence:CDC14B siRNA
<220> FEATURE:
<223> OTHER INFORMATION: CDC14 cell division cycle 14 homolog B (S.
```

-continued cerevisiae) (CDC14B, CDC14B1, CDC14B2, CDC14B3),
transcript variant 1, S. cerevisiae CDC14 homolog,
gene B double-stranded small interfering RNA
(siRNA)

<400> SEQUENCE: 111
gagcagccuu cuccaaacu 19

<210> SEQ ID NO 112
<211> LENGTH: 23
<212> TYPE: DNA
<213> ORGANISM: Artificial Sequence
<220> FEATURE:
<223> OTHER INFORMATION: Description of Combined DNA/RNA Molecule:CDC14B
siRNA
<220> FEATURE:
<223> OTHER INFORMATION: Description of Artificial Sequence:CDC14B siRNA
<220> FEATURE:
<223> OTHER INFORMATION: CDC14 cell division cycle 14 homolog B (S.
cerevisiae) (CDC14B, CDC14B1, CDC14B2, CDC14B3),
transcript variant 1, S. cerevisiae CDC14 homolog,
gene B double-stranded small interfering RNA
(siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 112
cagagcagcc uucuccaaac utc 23

<210> SEQ ID NO 113
<211> LENGTH: 19
<212> TYPE: RNA
<213> ORGANISM: Artificial Sequence
<220> FEATURE:
<223> OTHER INFORMATION: Description of Artificial Sequence:MJD siRNA
<220> FEATURE:
<223> OTHER INFORMATION: Machado-Joseph disease (MJD, MJD1, josephin),
spinocerebellar ataxia 3 (SCA3), olivocerebellar
ataxia 3, autosomal dominant, ataxin 3 (ATXN3, AT3,
ATX3) double-stranded small interfering RNA (siRNA)

<400> SEQUENCE: 113
cagaugcauc gaccaaaac 19

<210> SEQ ID NO 114
<211> LENGTH: 23
<212> TYPE: DNA
<213> ORGANISM: Artificial Sequence
<220> FEATURE:
<223> OTHER INFORMATION: Description of Combined DNA/RNA Molecule:MJD
siRNA
<220> FEATURE:
<223> OTHER INFORMATION: Description of Artificial Sequence:MJD siRNA
<220> FEATURE:
<223> OTHER INFORMATION: Machado-Joseph disease (MJD, MJD1, josephin),
spinocerebellar ataxia 3 (SCA3), olivocerebellar
ataxia 3, autosomal dominant, ataxin 3 (ATXN3, AT3,
ATX3) double-stranded small interfering RNA (siRNA)
<220> FEATURE:
<221> NAME/KEY: misc_feature
<222> LOCATION: (1)..(2)
<223> OTHER INFORMATION: DNA
<220> FEATURE:

-continued

<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 114
aacagaugca ucgaccaaaa ctt 23

<210> SEQ ID NO 115
<211> LENGTH: 19
<212> TYPE: RNA
<213> ORGANISM: Artificial Sequence
<220> FEATURE:
<223> OTHER INFORMATION: Description of Artificial Sequence:BIRC4 siRNA
<220> FEATURE:
<223> OTHER INFORMATION: baculoviral IAP repeat-containing 4 (BIRC4),
X-linked inhibitor of apoptosis (XIAP, XLP2),
apoptosis inhibitor 3 (API3), ILP1, MIHA
double-stranded small interfering RNA (siRNA)

<400> SEQUENCE: 115
ugugcuacac agucauuac 19

<210> SEQ ID NO 116
<211> LENGTH: 23
<212> TYPE: DNA
<213> ORGANISM: Artificial Sequence
<220> FEATURE:
<223> OTHER INFORMATION: Description of Combined DNA/RNA Molecule:BIRC4
siRNA
<220> FEATURE:
<223> OTHER INFORMATION: Description of Artificial Sequence:BIRC4 siRNA
<220> FEATURE:
<223> OTHER INFORMATION: baculoviral IAP repeat-containing 4 (BIRC4),
X-linked inhibitor of apoptosis (XIAP, XLP2),
apoptosis inhibitor 3 (API3), ILP1, MIHA
double-stranded small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 116
caugugcuac acagucauua ctt 23

<210> SEQ ID NO 117
<211> LENGTH: 19
<212> TYPE: RNA
<213> ORGANISM: Artificial Sequence
<220> FEATURE:
<223> OTHER INFORMATION: Description of Artificial Sequence:DFNA5 siRNA
<220> FEATURE:
<223> OTHER INFORMATION: deafness, autosomal dominant 5 (DFNA5),
nonsyndromic hearing impairment protein, hearing
loss gene, ICERE-1 double-stranded small
interfering RNA (siRNA)

<400> SEQUENCE: 117
agucuuccca cugcuucuu 19

<210> SEQ ID NO 118
<211> LENGTH: 23
<212> TYPE: DNA
<213> ORGANISM: Artificial Sequence
<220> FEATURE:
<223> OTHER INFORMATION: Description of Combined DNA/RNA Molecule:DFNA5
siRNA
<220> FEATURE:
<223> OTHER INFORMATION: Description of Artificial Sequence:DFNA5 siRNA
<220> FEATURE:
<223> OTHER INFORMATION: deafness, autosomal dominant 5 (DFNA5),
nonsyndromic hearing impairment protein, hearing
loss gene, ICERE-1 double-stranded small
interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 118
aaagucuucc cacugcuucu utg 23

<210> SEQ ID NO 119
<211> LENGTH: 19
<212> TYPE: RNA
<213> ORGANISM: Artificial Sequence
<220> FEATURE:
<223> OTHER INFORMATION: Description of Artificial Sequence:PHF1 siRNA
<220> FEATURE:
<223> OTHER INFORMATION: plant homeodomain (PHD) finger protein 1 (
PHF1),
transcript variant 1, PHD finger 1, PHF2, similar
to Drosophila Polycomblike double-stranded small
interfering RNA (siRNA)

<400> SEQUENCE: 119
ugcuggguau gaagcuuuc 19

<210> SEQ ID NO 120
<211> LENGTH: 23
<212> TYPE: DNA
<213> ORGANISM: Artificial Sequence
<220> FEATURE:
<223> OTHER INFORMATION: Description of Combined DNA/RNA Molecule:PHF1
siRNA
<220> FEATURE:
<223> OTHER INFORMATION: Description of Artificial Sequence:PHF1 siRNA
<220> FEATURE:
<223> OTHER INFORMATION: plant homeodomain (PHD) finger protein 1
(PHF1),
transcript variant 1, PHD finger 1, PHF2, similar
to Drosophila Polycomblike double-stranded small
interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 120

-continued caugcugggu augaagcuuu ctc 23

<210> SEQ ID NO 121
<211> LENGTH: 19
<212> TYPE: RNA
<213> ORGANISM: Artificial Sequence
<220> FEATURE:
<223> OTHER INFORMATION: Description of Artificial Sequence:TBX3 siRNA
<220> FEATURE:
<223> OTHER INFORMATION: T-box transcription factor (ulnar mammary syndrome) (TBX3, UMS), transcript variant 1 (TBX3-ISO), bladder cancer related protein XHL double-stranded small interfering RNA (siRNA)

<400> SEQUENCE: 121
ugccaaagag gauguacau 19

<210> SEQ ID NO 122
<211> LENGTH: 23
<212> TYPE: DNA
<213> ORGANISM: Artificial Sequence
<220> FEATURE:
<223> OTHER INFORMATION: Description of Combined DNA/RNA Molecule:TBX3 siRNA
<220> FEATURE:
<223> OTHER INFORMATION: Description of Artificial Sequence:TBX3 siRNA
<220> FEATURE:
<223> OTHER INFORMATION: T-box transcription factor (ulnar mammary syndrome) (TBX3, UMS), transcript variant 1 (TBX3-ISO), bladder cancer related protein XHL double-stranded small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 122
aaugccaaag aggauguaca utc 23

<210> SEQ ID NO 123
<211> LENGTH: 19
<212> TYPE: RNA
<213> ORGANISM: Artificial Sequence
<220> FEATURE:
<223> OTHER INFORMATION: Description of Artificial Sequence:PJA2 siRNA
<220> FEATURE:
<223> OTHER INFORMATION: praja 2, RING-H2 motif containing (PJA2), ring finger protein 131 (RNF131), Neurodap1, KIAA0438 double-stranded small interfering RNA (siRNA)

<400> SEQUENCE: 123
cagguaguga ggccaaaag 19

<210> SEQ ID NO 124
<211> LENGTH: 23
<212> TYPE: DNA
<213> ORGANISM: Artificial Sequence
<220> FEATURE:
<223> OTHER INFORMATION: Description of Combined DNA/RNA Molecule:PJA2 siRNA
<220> FEATURE:
<223> OTHER INFORMATION: Description of Artificial Sequence:PJA2 siRNA
<220> FEATURE:

-continued

<223> OTHER INFORMATION: praja 2, RING-H2 motif containing (PJA2), ring
      finger protein 131 (RNF131), Neurodap1, KIAA0438
      double-stranded small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 124
aacagguagu gaggccaaaa gtt 23

<210> SEQ ID NO 125
<211> LENGTH: 19
<212> TYPE: RNA
<213> ORGANISM: Artificial Sequence
<220> FEATURE:
<223> OTHER INFORMATION: Description of Artificial Sequence:HLCDGP1
      siRNA
<220> FEATURE:
<223> OTHER INFORMATION: down-regulated in lung cancer, HLCDGP1,
      PRO2975,
      casein kinase 1, alpha 1 (CSNK1A1, CK1)
      double-stranded small interfering RNA (siRNA)

<400> SEQUENCE: 125
ugcuagcauc augcacauc 19

<210> SEQ ID NO 126
<211> LENGTH: 23
<212> TYPE: DNA
<213> ORGANISM: Artificial Sequence
<220> FEATURE:
<223> OTHER INFORMATION: Description of Combined DNA/RNA Molecule:
      HLCDGP1
      siRNA
<220> FEATURE:
<223> OTHER INFORMATION: Description of Artificial Sequence:HLCDGP1
      siRNA
<220> FEATURE:
<223> OTHER INFORMATION: down-regulated in lung cancer, HLCDGP1,
      PRO2975,
      casein kinase 1, alpha 1 (CSNK1A1, CK1)
      double-stranded small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 126
taugcuagca ucaugcacau ctt 23

<210> SEQ ID NO 127
<211> LENGTH: 19
<212> TYPE: RNA
<213> ORGANISM: Artificial Sequence
<220> FEATURE:
<223> OTHER INFORMATION: Description of Artificial Sequence:GBDR1 siRNA -continued
<220> FEATURE:
<223> OTHER INFORMATION: putative glialblastoma cell differentiation-
      related
      (GBDR1), ubiquitin associated domain containing 1
      (UBADC1), UBA domain containing 1 (UBAC1)
      double-stranded small interfering RNA (siRNA)

<400> SEQUENCE: 127
cccgaaaaca uugcuagca 19

<210> SEQ ID NO 128
<211> LENGTH: 23
<212> TYPE: DNA
<213> ORGANISM: Artificial Sequence
<220> FEATURE:
<223> OTHER INFORMATION: Description of Combined DNA/RNA Molecule:GBDR1
      siRNA
<220> FEATURE:
<223> OTHER INFORMATION: Description of Artificial Sequence:GBDR1 siRNA
<220> FEATURE:
<223> OTHER INFORMATION: putative glialblastoma cell differentiation-
      related
      (GBDR1), ubiquitin associated domain containing 1
      (UBADC1), UBA domain containing 1 (UBAC1)
      double-stranded small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 128
aacccgaaaa cauugcuagc att 23

<210> SEQ ID NO 129
<211> LENGTH: 19
<212> TYPE: RNA
<213> ORGANISM: Artificial Sequence
<220> FEATURE:
<223> OTHER INFORMATION: Description of Artificial Sequence:LOC341549
      siRNA
<220> FEATURE:
<223> OTHER INFORMATION: similar to semaphorin cytoplasmic
      domain-associated protein 3B, LOC341549
      double-stranded small interfering RNA (siRNA)

<400> SEQUENCE: 129
gagcagaugg ccuggagau 19

<210> SEQ ID NO 130
<211> LENGTH: 23
<212> TYPE: DNA
<213> ORGANISM: Artificial Sequence
<220> FEATURE:
<223> OTHER INFORMATION: Description of Combined DNA/RNA Molecule:
      LOC341549
      siRNA
<220> FEATURE:
<223> OTHER INFORMATION: Description of Artificial Sequence:LOC341549
      siRNA
<220> FEATURE:
<223> OTHER INFORMATION: similar to semaphorin cytoplasmic
      domain-associated protein 3B, LOC341549
      double-stranded small interfering RNA (siRNA)
<220> FEATURE:
<221> NAME/KEY: misc_feature -continued
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 130
cagagcagau ggccuggaga utc 23

<210> SEQ ID NO 131
<211> LENGTH: 19
<212> TYPE: RNA
<213> ORGANISM: Artificial Sequence
<220> FEATURE:
<223> OTHER INFORMATION: Description of Artificial Sequence:ASB11 siRNA
<220> FEATURE:
<223> OTHER INFORMATION: ankyrin repeat and SOCS box-containing 11
(ASB11),
transcript variant 1, ankyrin repeat
domain-containing SOCS box protein ASB11
double-stranded small interfering RNA (siRNA)

<400> SEQUENCE: 131
uggagauccu gcuggcaaa 19

<210> SEQ ID NO 132
<211> LENGTH: 23
<212> TYPE: DNA
<213> ORGANISM: Artificial Sequence
<220> FEATURE:
<223> OTHER INFORMATION: Description of Combined DNA/RNA Molecule:ASB11
siRNA
<220> FEATURE:
<223> OTHER INFORMATION: Description of Artificial Sequence:ASB11 siRNA
<220> FEATURE:
<223> OTHER INFORMATION: ankyrin repeat and SOCS box-containing 11
(ASB11),
transcript variant 1, ankyrin repeat
domain-containing SOCS box protein ASB11
double-stranded small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 132
cauggagauc cugcuggcaa ata 23

<210> SEQ ID NO 133
<211> LENGTH: 19
<212> TYPE: RNA
<213> ORGANISM: Artificial Sequence
<220> FEATURE:
<223> OTHER INFORMATION: Description of Artificial Sequence:IFIT-1 siRNA
<220> FEATURE:
<223> OTHER INFORMATION: similar to interferon-induced protein with
tetratricopeptide repeats 1 (IFIT-1), interferon-induced
56 kDa protein (IFI-56K), LOC441570 double-stranded small
interfering RNA (siRNA)

-continued

<400> SEQUENCE: 133
auccaaaaga ugcacacau 19

<210> SEQ ID NO 134
<211> LENGTH: 23
<212> TYPE: DNA
<213> ORGANISM: Artificial Sequence
<220> FEATURE:
<223> OTHER INFORMATION: Description of Combined DNA/RNA Molecule:IFIT-1 siRNA
<220> FEATURE:
<223> OTHER INFORMATION: Description of Artificial Sequence:IFIT-1 siRNA
<220> FEATURE:
<223> OTHER INFORMATION: similar to interferon-induced protein with tetratricopeptide repeats 1 (IFIT-1), interferon-induced 56 kDa protein (IFI-56K), LOC441570 double-stranded small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 134
aaauccaaaa gaugcacaca uta 23

<210> SEQ ID NO 135
<211> LENGTH: 19
<212> TYPE: RNA
<213> ORGANISM: Artificial Sequence
<220> FEATURE:
<223> OTHER INFORMATION: Description of Artificial Sequence:COMP siRNA
<220> FEATURE:
<223> OTHER INFORMATION: cartilage oligomeric matrix protein (COMP), pseudoachondroplasia (PSACH), epiphyseal dysplasia 1, multiple (EDM1, EPD1, MED), thrombospondin-5 (THBS5) double-stranded small interfering RNA (siRNA)

<400> SEQUENCE: 135
cggucacgga ugacgacua 19

<210> SEQ ID NO 136
<211> LENGTH: 23
<212> TYPE: DNA
<213> ORGANISM: Artificial Sequence
<220> FEATURE:
<223> OTHER INFORMATION: Description of Combined DNA/RNA Molecule:COMP siRNA
<220> FEATURE:
<223> OTHER INFORMATION: Description of Artificial Sequence:COMP siRNA
<220> FEATURE:
<223> OTHER INFORMATION: cartilage oligomeric matrix protein (COMP), pseudoachondroplasia (PSACH), epiphyseal dysplasia 1, multiple (EDM1, EPD1, MED), thrombospondin-5 (THBS5) double-stranded small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)

-continued

<223> OTHER INFORMATION: DNA

<400> SEQUENCE: 136
cacggucacg gaugacgacu atg 23

<210> SEQ ID NO 137
<211> LENGTH: 19
<212> TYPE: RNA
<213> ORGANISM: Artificial Sequence
<220> FEATURE:
<223> OTHER INFORMATION: Description of Artificial Sequence:LOC133308 siRNA
<220> FEATURE:
<223> OTHER INFORMATION: hypothetical protein BC009732, hypothetical protein LOC133308, Na+/H+ exchanger domain containing 2 (NHEDC2) double-stranded small interfering RNA (siRNA)

<400> SEQUENCE: 137
ccaacagaag gaaguauuc 19

<210> SEQ ID NO 138
<211> LENGTH: 23
<212> TYPE: DNA
<213> ORGANISM: Artificial Sequence
<220> FEATURE:
<223> OTHER INFORMATION: Description of Combined DNA/RNA Molecule: LOC133308 siRNA
<220> FEATURE:
<223> OTHER INFORMATION: Description of Artificial Sequence:LOC133308 siRNA
<220> FEATURE:
<223> OTHER INFORMATION: hypothetical protein BC009732, hypothetical protein LOC133308, Na+/H+ exchanger domain containing 2 (NHEDC2) double-stranded small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 138
aaccaacaga aggaaguauu ctt 23

<210> SEQ ID NO 139
<211> LENGTH: 19
<212> TYPE: RNA
<213> ORGANISM: Artificial Sequence
<220> FEATURE:
<223> OTHER INFORMATION: Description of Artificial Sequence:MGC42105 siRNA
<220> FEATURE:
<223> OTHER INFORMATION: hypothetical protein MGC42105, hypothetical protein LOC167359 double-stranded small interfering RNA (siRNA)

<400> SEQUENCE: 139
cggauaggcu ucuaccgaa 19

<210> SEQ ID NO 140
<211> LENGTH: 23
<212> TYPE: DNA

-continued

<213> ORGANISM: Artificial Sequence
<220> FEATURE:
<223> OTHER INFORMATION: Description of Combined DNA/RNA Molecule:
      MGC42105
      siRNA
<220> FEATURE:
<223> OTHER INFORMATION: Description of Artificial Sequence:MGC42105
      siRNA
<220> FEATURE:
<223> OTHER INFORMATION: hypothetical protein MGC42105, hypothetical
      protein LOC167359 double-stranded small
      interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 140
aacggauagg cuucuaccga att 23

<210> SEQ ID NO 141
<211> LENGTH: 19
<212> TYPE: RNA
<213> ORGANISM: Artificial Sequence
<220> FEATURE:
<223> OTHER INFORMATION: Description of Artificial Sequence:MGC15875
      siRNA
<220> FEATURE:
<223> OTHER INFORMATION: hypothetical protein MGC15875, hypothetical
      protein LOC85007,
      transcript variant 1, alanine-glyoxylate aminotransferase
      2-like 2 (AGXT2L2), transcript variant 1, MGC45484,
      MGC117348 double-stranded small interfering RNA (siRNA)

<400> SEQUENCE: 141
ugugcuucag ccuggacaa 19

<210> SEQ ID NO 142
<211> LENGTH: 23
<212> TYPE: DNA
<213> ORGANISM: Artificial Sequence
<220> FEATURE:
<223> OTHER INFORMATION: Description of Combined DNA/RNA Molecule:
      MGC15875
      siRNA
<220> FEATURE:
<223> OTHER INFORMATION: Description of Artificial Sequence:MGC15875
      siRNA
<220> FEATURE:
<223> OTHER INFORMATION: hypothetical protein MGC15875, hypothetical
      protein LOC85007,
      transcript variant 1, alanine-glyoxylate aminotransferase
      2-like 2 (AGXT2L2), transcript variant 1, MGC45484,
      MGC117348 double-stranded small interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA -continued

<400> SEQUENCE: 142
aaugugcuuc agccuggaca atg 23

<210> SEQ ID NO 143
<211> LENGTH: 19
<212> TYPE: RNA
<213> ORGANISM: Artificial Sequence
<220> FEATURE:
<223> OTHER INFORMATION: Description of Artificial Sequence:FLJ38628
siRNA
<220> FEATURE:
<223> OTHER INFORMATION: hypothetical protein FLJ38628, ring finger
protein
185 (RNF185) double-stranded small interfering RNA
(siRNA)

<400> SEQUENCE: 143
gcacuuucga gugcaacau 19

<210> SEQ ID NO 144
<211> LENGTH: 23
<212> TYPE: DNA
<213> ORGANISM: Artificial Sequence
<220> FEATURE:
<223> OTHER INFORMATION: Description of Combined DNA/RNA Molecule:
FLJ38628
siRNA
<220> FEATURE:
<223> OTHER INFORMATION: Description of Artificial Sequence:FLJ38628
siRNA
<220> FEATURE:
<223> OTHER INFORMATION: hypothetical protein FLJ38628, ring finger
protein
185 (RNF185) double-stranded small interfering RNA
(siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 144
cagcacuuuc gagugcaaca uct 23

<210> SEQ ID NO 145
<211> LENGTH: 19
<212> TYPE: RNA
<213> ORGANISM: Artificial Sequence
<220> FEATURE:
<223> OTHER INFORMATION: Description of Artificial Sequence:IMAGE:
3568335
siRNA
<220> FEATURE:
<223> OTHER INFORMATION: clone IMAGE:3568335 3', FLJ39181 fis, clone
OCBBF2004235, DA771261 EST double-stranded small
interfering RNA (siRNA)

<400> SEQUENCE: 145
ugggcucacu cugcaacca 19

<210> SEQ ID NO 146
<211> LENGTH: 23
<212> TYPE: DNA
<213> ORGANISM: Artificial Sequence -continued
<220> FEATURE:
<223> OTHER INFORMATION: Description of Combined DNA/RNA
      Molecule:IMAGE:3568335 siRNA
<220> FEATURE:
<223> OTHER INFORMATION: Description of Artificial Sequence:IMAGE:
      3568335
      siRNA
<220> FEATURE:
<223> OTHER INFORMATION: clone IMAGE:3568335 3', FLJ39181 fis, clone
      OCBBF2004235, DA771261 EST double-stranded small
      interfering RNA (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 146
caugggcuca cucugcaacc agg 23

<210> SEQ ID NO 147
<211> LENGTH: 19
<212> TYPE: RNA
<213> ORGANISM: Artificial Sequence
<220> FEATURE:
<223> OTHER INFORMATION: Description of Artificial Sequence:LOC114971
      siRNA
<220> FEATURE:
<223> OTHER INFORMATION: hypothetical protein LOC114971, similar to
      RIKEN 2810004N20,
      similar to IMAGE:3348134, similar to dual specificity protein
      phosphatase 1, similar to mitogen-activated protein kinase
      phosphatase 7 (MKP-7) double-stranded small interfering RNA
      (siRNA)

<400> SEQUENCE: 147
ccugauucag gugcacaaa 19

<210> SEQ ID NO 148
<211> LENGTH: 23
<212> TYPE: DNA
<213> ORGANISM: Artificial Sequence
<220> FEATURE:
<223> OTHER INFORMATION: Description of Combined DNA/RNA Molecule:
      LOC114971
      siRNA
<220> FEATURE:
<223> OTHER INFORMATION: Description of Artificial Sequence:LOC114971
      siRNA
<220> FEATURE:
<223> OTHER INFORMATION: hypothetical protein LOC114971, similar to
      RIKEN 2810004N20,
      similar to IMAGE:3348134, similar to dual specificity protein
      phosphatase 1, similar to mitogen-activated protein kinase
      phosphatase 7 (MKP-7) double-stranded small interfering RNA
      (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA -continued

```
<400> SEQUENCE: 148

taccugauuc aggugcacaa atg                                          23


<210> SEQ ID NO 149
<211> LENGTH: 19
<212> TYPE: RNA
<213> ORGANISM: Artificial Sequence
<220> FEATURE:
<223> OTHER INFORMATION: Description of Artificial Sequence:DKFZP727G051
      siRNA
<220> FEATURE:
<223> OTHER INFORMATION: DKFZP727G051 protein, plant homeodomain (PHD)
      finger protein 19 (PHF19), similar to RIKEN
      3321402G02 double-stranded small interfering RNA
      (siRNA)

<400> SEQUENCE: 149

ggcauugaca gccacacau                                               19


<210> SEQ ID NO 150
<211> LENGTH: 23
<212> TYPE: DNA
<213> ORGANISM: Artificial Sequence
<220> FEATURE:
<223> OTHER INFORMATION: Description of Combined DNA/RNA
      Molecule:DKFZP727G051 siRNA
<220> FEATURE:
<223> OTHER INFORMATION: Description of Artificial Sequence:DKFZP727G051
      siRNA
<220> FEATURE:
<223> OTHER INFORMATION: DKFZP727G051 protein, plant homeodomain (PHD)
      finger protein 19 (PHF19), similar to RIKEN
      3321402G02 double-stranded small interfering RNA
      (siRNA)
<220> FEATURE:
<221> NAME/KEY: misc_feature
<222> LOCATION: (1)..(2)
<223> OTHER INFORMATION: DNA
<220> FEATURE:
<221> NAME/KEY: misc_feature
<222> LOCATION: (3)..(21)
<223> OTHER INFORMATION: RNA
<220> FEATURE:
<221> NAME/KEY: misc_feature
<222> LOCATION: (22)..(23)
<223> OTHER INFORMATION: DNA

<400> SEQUENCE: 150

aaggcauuga cagccacaca utt                                          23
```